Figure 2:
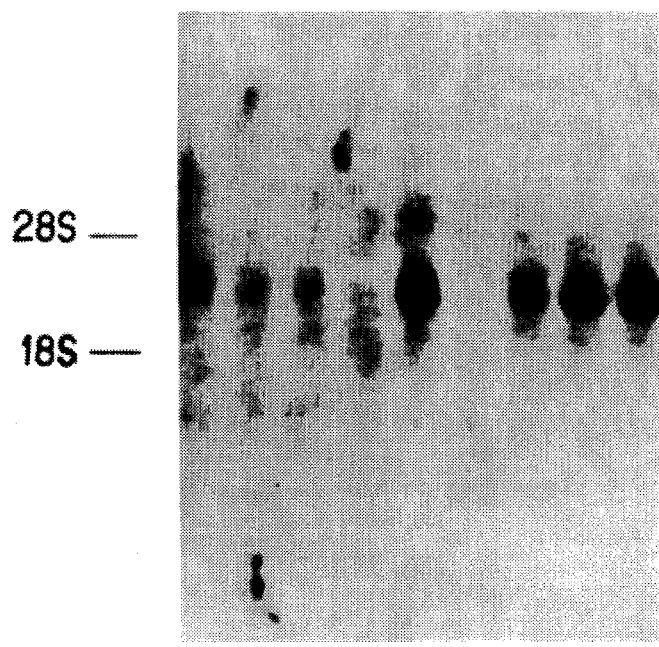

United States Patent [19]

Schlessinger et al.

[11] Patent Number: 5,538,886

[45] Date of Patent: Jul. 23, 1996

[54] RECEPTOR-TYPE PHOSPHOTYROSINE PHOSPHATASE-ALPHA

[75] Inventors: Joseph Schlessinger; Jan M. Sap, both of New York, N.Y.

[73] Assignee: New York University, New York, N.Y.

[21] Appl. No.: 15,985

[22] Filed: Feb. 10, 1993

Related U.S. Application Data

[63] Continuation-in-part of Ser. No. 654,188, Feb. 26, 1991, abandoned, which is a continuation-in-part of Ser. No. 551,276, Jul. 11, 1990, abandoned.

[51] Int. Cl.$^6$ .................. C12N 15/55; C12N 15/63; C12N 1/21; C12N 5/10

[52] U.S. Cl. .................. 435/240.2; 435/69.1; 435/69.8; 435/70.1; 435/71.2; 435/196; 435/252.3; 435/254.2; 435/172.3; 435/320.1; 435/6; 536/23.1; 536/23.2; 935/14; 935/27; 935/56; 935/69; 935/70; 935/72

[58] Field of Search .................. 435/69.1, 69.8, 435/70.1, 71.2, 196, 240.2, 252.3, 255, 172.3, 320.1, 6; 536/23.1, 23.2; 935/14, 27, 56, 69, 70, 72

[56] References Cited

FOREIGN PATENT DOCUMENTS

WO92/01050  1/1992  WIPO.

OTHER PUBLICATIONS

S. L. Berger et al. "Guide to Molecular Cloning Techniques" Meth. Enzymol. 152:393–399, 415–423, 432–447, 663–704 (1987).

Kaplan et al., Cloning of three human tyrosine phosphatases reveals a multigene family of receptor–linked protein–tyrosine–phosphatases expressed in brain, Proc. Natl. Acad. Sci. USA 87: 7000–7004 (1990).

Sap et al., Cloning and expression of a widely expressed receptor tyrosine phosphatase, Proc. Natl. Acad. Sci. USA 87: 6112–6116 (1990).

Daum et al., Characterization of a human recombinant receptor–linked protein tyrosine phosphatase, J. Biol. Chem., 266: 12211–12215 (1991).

Gebbink et al., Cloning, expression and chromosomal localization of a new putative receptor–like protein tyrosine phosphatase, FEBS Lett. 290: 123–130 (1991).

Tsai et al., Isolation and characterization of temperature–sensitive and thermostable mutants of the human receptor–like protein tyrosine phosphatase LAR, J. Biol. Chem. 266(16): 10534–10543 (1991).

George and Parker, Preliminary characterization of phosphotyrosine phosphatase activites in human peripheral blood lymphocytes: Identification of CD45 as a phosphotyrosine phosphatase, J. Cell Biochem. 42: 71–81 (1990).

Jirik et al., Cloning of a novel receptor–linked protein tyrosine phosphatase from a human hepatoblastoma cell line, FASEB J. 4A: 2082 (Abstr. 2253) (1990).

Jirik et al., Cloning and chromosomal assignment of a widely expressed human receptor–like protein–tyrosine phosphatase, FEBS Lett. 273: 239–242 (1990).

Krueger et al., Structural diversity and evolution of human receptor–like protein tyrosine phosphatases, EMBO J. 9: 3241–3252 (1990).

Matthews et al., Identification of an additional member of the protein–tyrosine–phosphatase family: Evidence for alternative splicing in the tyrosine phosphatase domain, Proc. Natl. Acad. Sci. USA 87: 4444–4448 (1990).

Ohagi et al., Sequence of a cDNA encoding human LRP (leukocyte common antigen–related peptide), Nucl. Acids Res. 18: 7159 (1990).

Streuli et al., Distinct functional roles of the two intracellular phosphatase like domains of the receptor–linked protein tyrosine phosphatases LCA and LAR, EMBO Journal 9: 2399–2407 (1990).

Kiener and Mittler, CD45–protein tyrosine phosphatase cross–linking inhibits T–cell receptor CD3–mediated activation in human T–cells, J. Immunol. 143: 23–28 (1989).

Mustelin et al., Rapid activation of the T–cell tyrosine protein kinase pp56lck by the CD45 phosphotyrosine phosphatase, Proc. Natl. Acad. Sci. USA 86: 6302–6306 (1989).

Ostergaard et al., Expression of CD45 alters phosphorylation of the lck–encoded tyrosine protein kinase in murine lymphoma T–cell lines, Proc. Natl. Acad. Sci. USA 86: 8959–8963 (1989).

Hall et al., Complete exon–intron organization of the human leukocyte common antigen (CD45) gene, J. Immunol. 141: 2781–2787 (1988).

Streuli et al., A new member of the immunoglobulin superfamily that has a cytoplasmic region homologous to the leukocyte common antigen, J. Exp. Med. 168: 1523–1530 (1988).

Charbonneau et al., The leukocyte common antigen (CD45): A putative receptor–linked protein tyrosine phosphatase, Proc. Natl. Acad. Sci. USA 85: 7182–7186 (1988).

Ralph et al., Structural variants of human T200 glycoprotein (leukocyte–common antigen), EMBO J. 6: 1251–1257 (1987).

Streuli et al., Differential usage of three exons generates at least five different mRNAs encoding human leukocyte common antigens, J. Exp. Med. 166: 1548–1566 (1987).

Hariharan et al., Cloning and characterization of a receptor–class phosphotyrosine phosphatase gene expressed on central nervous system axons in Drosphila melanogaster, Proc. Natl. Acad. Sci. USA 88: 11266–11270 (1991).

(List continued on next page.)

*Primary Examiner*—Robert A. Wax
*Assistant Examiner*—Rebecca Prouty
*Attorney, Agent, or Firm*—Pennie & Edmonds

[57] ABSTRACT

A novel receptor-type protein tyrosine phosphatase (RPTP) protein or glycoprotein and the DNA coding therefor is expressed in a wide variety of mammalian tissues. Included in this family of proteins are human RPTPα, human RPTPβ and human RPTPγ. The RPTP protein or glycoprotein may be produced by recombinant means. Antibodies to the proteins, methods for measuring the quantity of the proteins, methods for screening compounds, such as drugs, which can bind to the proteins and inhibit or stimulate their activity, are provided.

13 Claims, 16 Drawing Sheets

OTHER PUBLICATIONS

Streuli et al., A family of receptor–linked protein tyrosine phosphatases in humans and Drosophila, Proc. Natl. Acad. Sci. USA 86: 8698–8702) (1989).

Gu et al., Identification, cloning, and expression of a cytosolic megakaryocyte protein–tyrosine–phosphatase with sequence homology to cytoskeletal protein 4.1, Proc. Natl. Acad. Sci. USA 88: 5867–5871 (1991).

Lombroso et al., Molecular characterization of a protein–tyrosine–phosphatase enriched in striatum, Proc. Natl. Acad. Sci. USA 88: 7242–7246 (1991).

Yang and Tonks, Isolation of a cDNA clone encoding a human protein–tyrosine phosphatase with homology to the cytoskeletal–associated proteins band 4.1, ezrin, and talin, Proc. Natl. Acad. Sci. USA 88: 5949–5953 (1991).

Chernoff et al., Cloning of a cDNA for a major human protein–tyrosine–phosphatase, Proc. Natl. Acad. Sci. USA, 87: 2735–2739 (1990).

Cool et al., Overexpression of a T–cell protein tyrosine phosphatase (PTPase) in BHK Cells, FASEB J. 4: A2078 (abstr. 2230) (1990).

Guan et al., Cloning and expression of a protein–tyrosine––phosphatase, Proc. Natl. Acad. Sci. USA 87: 1501–1505 (1990).

Thomas, et al., ABA, A novel member of the tyrosine phosphatase family, FASEB J. 4: A2078 (Abstr. 3140) (1990).

Tonks et al., CD45, an integral membrane protein tyrosine phosphatase, J. Biol. Chem. 265: 10674–10680 (1990).

Charbonneau et al., Human placenta protein–tyrosine–phosphatase: Amino acid sequence and relationship to a family of recetor–like proteins, Proc. Natl. Acad. Sci. USA 86: 5252–5256 (1989).

Cool et al., cDNA isolated from a human T–cell library encodes a member of the protein–tyrosine–phosphatase family, Proc. Natl. Acad. Sci. USA 86: 5257–5261 (1989).

Tonks et al., Purification of the major protein–tyrosine––phosphatases of human placenta, J. Biol. Chem. 263: 6722–6730 (1988).

Tonks et al., Demonstration that the leukocyte common antigen CD45 is a protein tyrosine phosphatase, Biochemistry 27: 8695–8701 (1988).

Matthews et al., Characterization of hematopoietic intracellular protein tyrosine phosphatases: Description of a phosphatase containing an SH2 Domain and another enriched in proline–, glutamic acid–, serine–, and threonine–rich sequences, Molec. and Cell. Biol. 12: 2396–2405 (1992).

Plutzky et al., Isolation of a src homology 2–containing tyrosine phosphatase, Proc. Natl. Acad, Sci. USA 89: 1123–1127 (1992).

Yi et al., Protein tyrosine phosphatase containing SH2 domains: characterization, preferential expression in hemotopoietic cells, and localization to human chromosome 12p12–p13, Mol. and Cell. Biol. 12: 836–846 (1992).

Shen et al., A protein–tyrosine phosphatase with sequence similarity to the SH2 domain of the protein–tyrosine kinases, Nature 352: 736–739 (1991).

Klarlund, Transformation of cells by an inhibitor of phosphatases acting on phosphotyrosine in proteins, Cell 41: 707–717 (1985).

Pallen et al., Purification of a phosphotyrosine phosphatase that dephosphorylates the epidermal growth factor receptor autophosphorylation sites, Ann. N.Y. Acad. Sci. 551: 299–308 (1988).

Butler et al., Characterization of a membrane–associated phosphotyrosyl protein phosphatase from the A431 human epidermoid carcinoma cell line, Eur. J. Biochem. 185: 475–483 (1989).

Cyert and Thorner, Putting it on and taking it off: Phosphoprotein phosphatase involvement in cell cycle regulation, Cell 57: 891–893 (1989).

Jones et al., Phosphotyrosyl–protein phosphatases, J. Biol. Chem. 264: 7747–7753 (1989).

Pingel and Thomas, Evidence that the leukocyte–common antigen is required for antigen–induced T lymphocyte proliferation, Cell 58: 1055–1065 (1989).

Pot and Dixon, A thousand and two protein tyrosine phosphatases, Biochem. Biophys. Acta. 1136: 35–43 (1992).

Fischer et al., Protein tyrosine phosphatases: A diverse family intracellular and transmembrane enzymes, Science 253: 401–406 (1991).

Hunter, Protein–tyrosine phosphatases: The other side of the coin, Cell 58: 1013–1016 (1989).

Thomas, The leukocyte common antigen family, Ann. Rev. Immunol. 7: 339–369 (1989).

Tonks and Charbonneau, Protein tyrosine dephosphorylation and signal transduction, Trends in Biochem. Sci. 14: 497–500 (1989).

FIG. 1A

```
                    10                    30                    50                    70
gaattccggcgagtgaggcgctgacaggactcgcggggcatcttgcacagaccctggaccacgccgccatcgcagcctccag
                       90                   110                   130                   150                   170
cccagtcctctctctgccgcttctctcgccatggaggccgacccgtccgcgggcttcgagcagcggaccgggccgggct
                     190                   210                   230                   250
gacccatgggccgagagcccgtcctgaggcgagctgccgtgccgcgtgccgtcccccagcgccccagcgccgggctcggt
                     270                   290                   310                   330
cagcatggattcctggttcattcttgtcctgtttggcagtggtctaatacatgttagtgccaacaatgctactacagtttcacc
M  D  S  W  F  I  L  V  L  F  G  S  G  L  I  H  V  S  A  N  N  A  T  T  V  S  P
       350                   370                   390                   410
ttctttaggaacgacagattaattaaacatcaacaacagaattggctaaggaggaataaacctcaaattcaacctcttc
                     430                   450                   470                   490
 S  L  G  T  T  R  L  I  K  T  S  T  T  E  L  A  K  E  E  N  K  T  S  N  S  T  S  S
agtaattctcttctgtggcaccacattcagccaaactgactctggagccccactgtgactactgttaattcttcaca
                     510                   530                   550                   570                   590
 V  I  S  L  S  V  A  P  T  F  S  P  N  L  T  L  E  P  T  Y  V  T  T  V  N  S  S  H
ctctgacaatgggaccaggagggcagcagcacggaatctggaggcacacctaccattcccgacgaagctggcttattgagaa
                     610                   630                   650                   670
 S  D  N  G  T  R  R  A  A  S  T  E  S  G  G  T  T  I  S  P  N  G  S  W  L  I  E  N
ccagttccacgatgccataacagaaccctggagggggaactccgactgcagcaaccactccagaaacttcccccggcaga
                     690                   710                   730                   750
 Q  F  T  D  A  I  T  E  P  W  E  G  N  S  S  T  A  A  T  T  P  E  T  F  P  P  A  D
tgagcaccaattattgcgatgatgtggtggcctgtcctctctgtagtaatcgtgtttattatcatagttctgtacatgttaag
                     770                   790                   810                   830
 E  T  P  L  I  A  V  M  V  A  L  S  S  L  L  V  I  V  F  I  I  L  V  L  Y  M  L  R
gtttaagaaatacagcagctgggagtcattccaactctttccgcctgtcaaatgccgacggaggtgtggagcccaaag
 F  K  K  Y  K  Q  A  G  S  H  S  N  S  F  R  L  S  N  G  R  T  E  D  V  E  P  Q  S
```

```
                                       890                                910
     850              870
tgtaccacttctggccagtccccggcccaacaggagtaccaccactgcctgtggacaagctggaagaggagattaaccg
 V  P  L  L  A  R  S  P  S  T  N  R  K  Y  P  P  L  P  V  D  K  L  E  E  E  I  N  R
   930              950                970                990               1010 gggaatggctgatgacaataagctcttcagagaagaattcaacgctctccctgcttgtcctatccggccacctgtgaggctgc
 R  M  A  D  D  N  K  L  F  R  E  E  F  N  A  L  P  A  C  P  I  Q  A  T  C  E  A  A
              1030               1050               1070               1090 ctccaaggagaaacaaggaaaaaccgctatgtaaacatcctgcctatgaccactctagagtgcacctgacacctgttg
 S  K  E  E  N  K  E [K  N  R  Y  V  N  I  L  P  Y  D  H  S  R  V  H  L  T  P  V  E
          1110               1130               1150               1170 aagggtcccagattctgattactatcaacgcttcattcattaatggctaccaggaaagaacaaattcatcgctgcacaaggac
 G  V  P  D  S  D  Y  I  N  A  S  F  I  N  G  Y  Q  E  K  N  K  F  I  A  A  Q  G  P
         1190               1210               1230               1250 caaagagaagaacagtgaatgacttctggagaatgatatgggaaccaaaacagctactattgtcatggtgaccaacctgaagg
 K  E  E  T  V  N  D  F  W  R  M  I  W  E  Q  N  T  A  T  I  V  M  V  T  N  L  K  E
         1270               1290               1310               1330 agagaaggagtgtaaatgtgccaatactggccagaccaaggctgctggacctatgggaatgtccgtgtgtctgtcgaggatg
 R  K  E  C  K  C  A  Q  Y  W  P  D  Q  G  C  W  T  Y  G  N  V  R  V  S  V  E  D  V
         1350               1370               1390               1410               1430 tgactgttctggtggactacacagtacggaatttctgatccaggaaattctcgatccaggtgggcgacgatgtgaccaacagggaacaacacagcctcat
 T  V  L  V  D  Y  T  V  R  K  F  S  I  Q  Q  V  G  D  V  T  N  R  K  P  Q  R  L  I
         1450               1470               1490               1510 cactcagttccacttccacgctggccagactttgggtgccttcaccccaattggcatgctgaagttcctgaagaaggtgaag
 T  Q  F  H  F  T  S  W  P  D  F  G  V  P  F  T  P  I  G  M  L  K  F  L  K  K  V  K
         1530               1550               1570               1590 gcctgtaaccctcagtacgcaggggctatcgtggtccactgcagtgcgggtgaggcgcactggaggccactttgttgtcatcgatg
 A  C  N  P  Q  Y  A  G  A  I  V  V  H  C  S  A  G  V  G  R  T  G  T  F  V  V  I  D  A
```

FIG.1B

```
                           1630                         1650                         1670
ccatgctggacatgatgcattcggagcgcaaagtggatgtgtatatggggtttgtgagccggatccggagccagcgctgccagatggta
 M  L  D  M  M  H  S  E  R  K  V  D  V  Y  G  F  V  S  R  I  R  A  Q  R  C  Q  M  V
   1690                        1710                         1730                      1770
cagcagcagcagtacgtcttcatataccaggccctctgggcattatctgtatggggacacagaactggaagtgacttctc
 Q  T  D  M  Q  Y  V  F  I  Y] Q  A  L  L  E  H  Y  L  Y  G  D  T  E  L  E  V  T  S  L
                       1790                       1810                        1830                     1850
tagaaaccccactacaaaaattttataacagatcccggggactagcaacaacgggttaagagaggagtttaagaaattaacttc
 E  T  H  L  Q  K  I  Y  N  K  I  P  G  T  S  N  N  G  L  E  E  E  F  K  K  L  T  S
     1870                        1890                        1910                        1930
aatcaaaatccagaatgacaagatgcacagatgcgcacggagggaaaccttccagcaacatgaagaggaaccgggttttacagatcattccatat
 I  K  I  Q  N  D  K  M  R  T  G  N  L  P  A  N  M  K [K  N  R  V  L  Q  I  I  P  Y
         1950                        1970                         1990                        2010
gaatttaacagagtgatcattccagtcaaacagggcgaagagaataccatatgtgaacgactacttcattgatggataccggc
 E  F  N  R  V  I  I  P  V  K  R  G  E  E  N  T  D  Y  V  N  A  S  F  I  D  G  Y  R  Q
                         2030                        2050                        2070                     2110
agaaggactcctacacattgccagccagggccccctccttcctccacacgattgaggacttctggagaatgatctggggagtggaagtcctg
 K  D  S  Y  I  A  S  Q  G  P  L  L  H  T  I  E  D  F  W  R  M  I  W  E  W  K  S  C
                         2130                         2150                        2170                    2190
ttctatatcgtaatgctgacagaactggaagaggaagaggagagaggccagtgtgccaatctggcatctgatggcctggtgtcctac
 S  I  V  M  L  T  E  L  E  E  R  G  Q  E  K  C  A  Q  Y  W  P  S  D  G  L  V  S  Y
      2210                        2230                        2250                         2270
ggagacatcacagttgagctgaagaagaaggaggaggaatgtgaaagctgtgagcatacactgtccagacctcctggtcaccaaccaccagggga
 G  D  I  T  V  E  L  K  K  E  E  E  C  E  S  Y  T  V  R  D  L  L  V  T  N  T  R  E  N
```

FIG.1C

```
                                    2330
acaagagtcggcaaatccggcagttccacttccacggctggcctgaggtggcatcccagcgacggcaaggcatgatcaacat
  K S R Q I R Q F  H F H G W  P E V G I P S D G K G M I N I
2370                    2390                    2410                   2430                    2450
cattgcagcagtgcagaagcagcagcagcagtcggggaaccatccatcactgtgcactgtgcagtgccggggcaggacggacgga
  I A A V Q K Q Q Q S G N H P I T V H C S A G A G R T G
2470                    2490                    2510                    2530
accttctgtgccttggccacagtcctggaacgtgtgaagcagaaggaatttagatgtctccaaactgtcaagagctgcggc
  T F C A L S T V L E R V K A E G I L D V F Q T V K S L R L
                       2570                    2590                    2610
tgcagaggccacacatggtccagacactggaacagtatgaattctgtacaaggtggtacaggaatacattgacgcctttcaga
  Q R P H M V Q T L E Q Y E F C Y] K V V Q E Y I D A F S D
2630                    2650                   2670                   2690
ttatgccaacttcaagtgacaggtgacaaggcccacagacaggagaattgccttaatattttgtaatattctgttttgttaat
  Y A N F K -.
2710                   2730                   2750                    2770                    2790
ataccaaattgtatatcttataactgttttagaaatggcacatggcttctattacctgttagatggagattttgtatgta
                        2810                   2830                    2850                    2870
aatgtgttagcactgatagtcctttccagtgtttattgggaaattaatagtgtgatattgggttgatataatgaattc
```

FIG.1D

FIG.1E

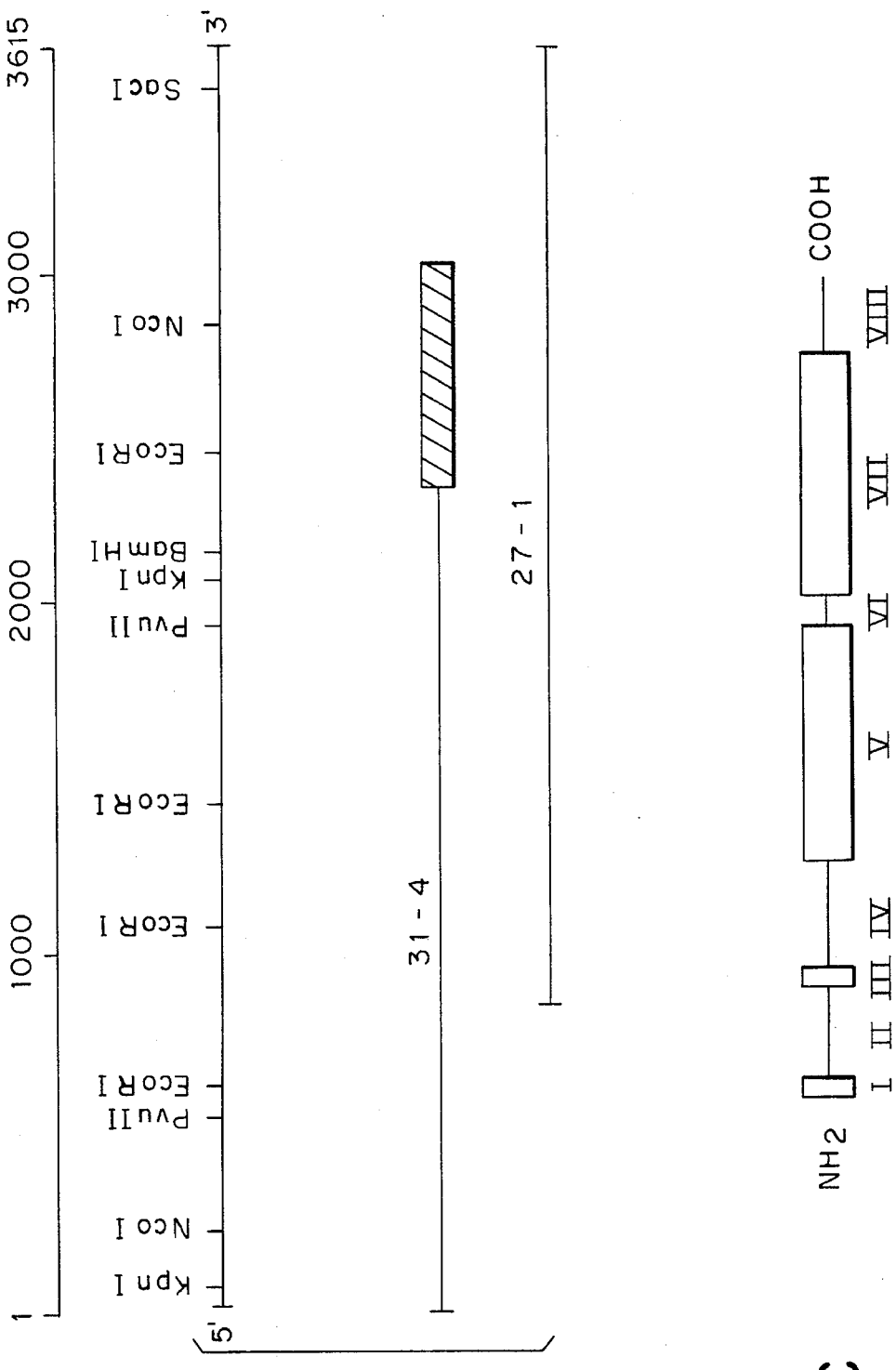

FIG.4D

```
1  ①                                                                                  68
   MDSWFILVLLCSGLICVS  ANNATTVAPSVGITRLINSSTAEPVKEEAKTSNPTSSLTSLSVAPTFSP
2                                                                                     68
       F    H         SLT    KT  TLA N  S   VI
1  NITLGPTYLTTVNSSDNGTTRTASTNSIGITISPNGTWLPDNQFTDARTEPWEGNSSTAATTPETFP               136
2                                                                                    136
   L  E V H       RA EGT   S  IE I
1  PSGNSDSKDRRDETPIIAVMVALSSLLVIVFIIIVLYML RFKKYKQAGSHSNSFRLSNGRTEDVEPQS              204
2  A——                                                                               195
                 ③
1  VPLLARSPSTNRKYPPLPVDKLEEEINRRMADDNKLFREEFNALPACPIQATCEAASKEE NKEKNRYV              272
2                                                                                    263
1  NILPYDHSRVHLTPVEGVPDSDYINASFINGYQEKNKFIAAQGPKEETVNDFWRMIWEQNTATIVMVT               340
2                                                                                    331
                   ⑤
1  NLKERKECKCAQYWPDQGCWTYGNIRVSVEDVTVLVDYTVRKFCIQQVGDMTNRKPQRLITQFHFTSW               408
2                                                                                    399
              V                          S  V       S
1  PDFGVPFTPIGMLKFLKKVKACNPQYAGAIVVHCSAGVGRTGTFVVIDAMLDMMHTERKVDVYGFVSR               476
2                                                                                    467
                                                                         S
1  IRAQRCQMVQTDMQYVFIYQALLE HYLYGDTELEVTSLETHLQKIYNKIPGTSNNGLEEEFKKLTSIK              544
2                                                                                    535
                         ⑦
1  IQNDKMRTGNLPA NMKKNRVLQIIPYEFNRVIIPVKRGEENTDYVNASFIDGYRQKDSYIASQGPLLH              612
2                                                                                    603
                                         N
1  TIEDFWRMIWEWKSCSIVMLTELEERGQEKCAQYWPSDGLVSYGDITVELKKEEECESYTVRDLLVTN               680
2                                                                                    671
1  TRENKSRQIRQFHFHGWPEVGIPSDGKGMISIIAAVQKQQQQSGNHPITVHCSAGAGRTGTFCALSTV               748
2                                                                                    739
1  LERVKAEGILDVFQTVKSLRLQRPHMVQTLEQYEFCYKVVQEY IDAFSDYANFK                            802
2                                                                                    793
```

```
              10          20          30          40
LCA       NqnKNRYVdILPYDynRVeL   sEinGdagSnYINASyIdGfkEprKyIAA
          | ||||| |||||  ||    | |    | ||||||  ||  |  | |||
RPTPase α NKeKNRYVNILPYDHSRVhLtpvE  GvpdSDYINASfInGYqEknKfIAA
          | |||| ||                       ||||||    ||
RPTPase β NKHKNRYINIvAYDHSRVKLaqLaeKDgKItDYINANYVDGYNrpKAYIAA
          ||||||||| |||||||||| |  | ||| ||||||||||||||  |||||
RPTPase γ NKHKNRYINIIAYDHSRVKLrpLpgKDsKhsDYINANYVDGYNkaKAYIAt CON       NkhKNRY-nII-YDhsRVkL—I—k—k-sdYINA-y-dGynepk-yIAa 50          60          70          80          90
LCA       QGPrdETVdDFWRMIWEQkatvIVMVTrceEgnrnKCAeYWPsMeegTra
          |||   ||| ||||||||||    ||||||| |     ||| |||   |
RPTPase α QGPkeETVnDFWRMIWEQNtatIVMVTNLkErkecKCAQYWPdqGewTYG
          |||      | |||||||||| |   ||| |  |   ||  ||||  |  ||
RPTPase β QGPLKSTaEDFWRMIWEhNvevIVMITNLVEKGRRKCDQYWPadGSEEYG
          ||||||| |||||||||| |  |||||||||||||||||||||||  |||||
RPTPase γ QGPLKSTfEDFWRMIWEqNtgiIVMITNLVEKGRRKCDQYWPtenSEEYG CON       QGPlk-TveDFWRMIWEqnt-vIVM-TnIvEkgrrKC-qYWP—gse-yg 100         110         120                 130
LCA       fgdVvVkinqhkrcpDYiiqKI        nIvn    kkekatgRevThiq
           |   |   ||     |   |          | |      |      |
RPTPase α NirVsVedVtVLv  DYTVRKFc       IqqvGd  mtnRkpqRIiTQfH
          |    |   | ||  ||||  |        |   |    |   | | || |
RPTPase β NfIVTqKSVqVLA  yYTVRnFtIRNTKIKK Gs    qKGRpsgRVVTQYH
          |  | || |  |   ||||| | |||| || |      |||  ||| |||||
RPTPase γ NiiVTIKStkihAc YTVRrFsiRNTKvKK Gqkgnp KGRqneRVViQYH CON       ni-Vtvk-v-vIa—dYtvrkf—rntki-k-g-k——kgr—gRvvtqyh
```

FIG.5A

```
              140       150       160       170       180       190
LCA        FTSWPDhGVPedPhlILKlrrrVnAfsnffsGpIVVHCSAGVGRTGTyigID
           ||||||  |||    |    ||      ||      |  |||||||||||||  ||
RPTPase α  FTSWPDfGVPftPigmLKFIkKVkAcnpqyaGaIVVHCSAGVGRTGTfvVID
           | |||  |||       |  |         |  |||||||||||||  | |
RPTPase β  YTQWPDMGVPEYsLPVLTFVRKaayAkrhavGPVVVHCSAGVGRTGTYIVID
           ||||||||||| ||||||||    |     | | ||||||||||||||| |
RPTPase γ  YTQWPDMGVPEYaLPVLTFVRrssaArmpetGPVIVHCSAGVGRTGTYIViD CON        -T-WPDmGVPeyplpvL-fvr-v-aa———Gp-vVHCSAGVGRTGTyiviD 200       210       220       230
LCA        AMLegleaEnKVDVYGyVvkIRrQRCIMVQveaQYillhQALvE
           |||      |  ||||||| |  ||| |||  ||  | ||| |
RPTPase α  AMLdmmhtErKVDVYGFVsrIRaQRCqMVQTdmQYVFIyQALIE
           ||         |   ||  ||  ||   ||||| |||| | |
RPTPase β  SMLQQIqhEgTVNifGFLKHIRsQRNYLVQTEEQYVFIHDtLvE
           ||||||     |||  |||||||| |||||||||||| ||| |
RPTPase γ  SMLQQIkdksTVNvIGFLKHIRtQRNYLVQTEEQYiFIHDaLIE CON        -MLqqi—e—V-vyGf-khiR-QR-y-VQteeQY-fIh-aL-E
```

FIG.5B

```
              10         20         30        40
LCA       NksKNRnsnvIPYdyNRVplkhelemskesehdsdessdddsdsEEpskY
           |  |||    |||  |||                          ||  |
RPTPase α  NmkKNRvlqIIPYEfNRVilpvkr                  GEEnTDY
           |  |||    ||||   |  ||                    ||  |||
RPTPase β  NrEKNRtSSIIPvERsRVGIssLs                  GE GTDY
           | ||||  ||  | ||  |||   |                 |  ||||
RPTPase γ  NkEKNRnSSvvPsERaRVGIapLp                  GmkGTDY CON        NkeKNRnss-iPyernRVg--l----------------geegtdY 50        60         70        80         90
LCA       iNASFImsYwkpevmIAaQGPLkeTIgDFWqMIfqrKvkvIVMLTELkhg
          |||||  |        ||  ||||  || ||| ||     |||||||||
RPTPase α vNASFIdGYrQkdsyIAsQGPLLHTIeDFWRMIWewKscsIVMLTELeer
          ||| | |||  |    |  ||||||  |||||||||       ||
RPTPase β INASYIMGYYQSNEFIITQHPLLHTIKDFWRMIWDHNAQIVVMiPDgQnm
          ||||||||||  ||||||||||| || ||||||||||||||  || || |
RPTPase γ INASYIMGYYrSNEFIITQHPLpHTtKDFWRMIWDHNAQiiVMIPDnQsl CON       iNAS-ImgYyqsnefI-tQ-PLlhTikDFWrMIwdh-naqiVMl----q--

100       110       120       130       140
LCA       dQEiCAQYW geGkqtYGDIeVdLKdtdksstYTI RvfelrhskrkdSRtv
          || ||||||  |    ||||   | ||        ||  |            ||
RPTPase α gQEkCAQYWPsdGIvsYGDItVeLKkeeeCESYTV RdllvtntreNkSRql
             |  |||                |||  |          |       |    |
RPTPase β A EDEFVYWPn    kDEpi    NCESFkVTLmaeehkCLSNEEkll
          | ||||||||      |        ||| | ||      ||||||  |
RPTPase γ A EDEFVYWPs    reEsm    NCEaFtVTLiskdrICLSNEEqil CON       aE-e-qYWps-g---ygd--v-lk---nces-tvt---e-r-clsne-r-i 150                 160        170       180
LCA       yQy            qY   tnWsveqIP aepKelISmIqvVkQKlpQk
           |              |    |   |  | | |||  |  || |
RPTPase α rQf            HF   hgWPevgiP SdgKgmISilaaV Qk  Qq
           |                  ||   |    ||     |||
RPTase  β IQDFILEATQDDYVLEVRHFQCPKWPNPDsPISkTFELISVI       K
          |||||||||||||||||||||||||||| || | ||||| ||       |
RPTase  γ IhDFILEATQDDYVLEVRHFQCPKWPNPDaPISsTFELInVI       K CON       iqdfileatqddyvlevrhfqcpkWpnpd-Pis-t-ellsvl-------qk
```

FIG.5C

```
              190       200       210       220       230
LCA      nsseGNkhhkstPlliHCrdGsqqTGiFCALlnILEsaetEevvDiFQvVKa
           ||        |   ||   |    ||  ||||    ||     |    |  || ||
RPTPase α  qqsGNh       PitVHCsaGagrTGTFCALsTvLErvkaEgilDVFQtVKs
            |           |  ||   |    ||||||| |      |      ||  |
RPTPase β  EEAaNR    DGPmIVHDEhGgVtAGTFCALTTLmhQLEkENsVDVyQVAKM
           ||| |     |||  ||||||  |  ||   ||||||    |||  ||  ||  |||||
RPTPase γ  EEAltR    DGPtIVHDEyGaVsAGmICALTTLsqQLEnENaVDVfQVAKM CON       -eea-nr----dgP-ivH-e-Gav--GtfCALttlleqle-En-vDvfQv-Km 240       250
LCA      LrkaRPgMVsTfEQYqFlYdVias
          |  || ||  |  |||  |   |  |
RPTPase α  LaLqRPhMVqTIEQYeFcYKVvqe
            |  ||         |||  |  |||
RPTPase β  INLMRPGVFaDIEQYQFIYKViLS
           |||||||||  |||||||  ||    ||
RPTPase γ  INLMRPGVFtDIEQYQFIYKarLS CON       -nlmRPg-----iEQYqFlYkvils
```

FIG.5D

```
  1 ATGGATTCCTGGTTCATTCTTGTTCTGCTCGGCAGTGGTCTGATATGTGTCAGTGCCAAC  60
  1 [M  D  S  W  F  I  L  V  L  L  G  S  G  L  I  C  V  S] A  N   20

61 AATGCTACCACAGTTGCACCTTCTGTAGGAATTACAAGATTAATTAACTCATCAACGGCA 120
 21  N  A  T  T  V  A  P  S  V  G  I  T  R  L  I  N  S  S  T  A   40

121 GAACCAGTTAAAGAAGAGGCCAAAACTTCAAATCCAACTTCTTCACTAACTTCTCTTTCT 180
 41  E  P  V  K  E  E  A  K  T  S  N  P  T  S  S  L  T  S  L  S   60

181 GTGGCACCAACATTCAGCCCAAATATAACTCTGGGACCCACCTATTTAACCACTGTCAAT 240
 61  V  A  P  T  F  S  P  N  I  T  L  G  P  T  Y  L  T  T  V  N   80

241 TCTTCAGACTCTGACAATGGGACCACAAGAACAGCAAGCACCAATTCTATAGGCATTACA 300
 81  S  S  D  S  D  N  G  T  T  R  T  A  S  T  N  S  I  G  I  T  100

301 ATTTCACCAAATGGAACGTGGCTTCCAGATAACCAGTTCACGGATGCCAGAACAGAACCC 360
101  I  S  P  N  G  T  W  L  P  D  N  Q  F  T  D  A  R  T  E  P  120

361 TGGGAGGGGAATTCCAGCACCGCAGCAACCACTCCAGAAACTTTCCCTCCTTCAGGTAAT 420
121  W  E  G  N  S  S  T  A  A  T  T  P  E  T  F  P  P  S  G  N  140

421 TCTGACTCGAAGGACAGAAGAGATGAGACACCAATTATTGCGGTGATGGTGGCCCTGTCC 480
141  S  D  S  K  D  R  R  D  E  T [P  I  I  A  V  M  V  A  L  S  160

481 TCTCTGCTAGTGATCGTGTTTATTATCATAGTTTTGTACATGTTAAGGTTTAAGAAATAC 540
161  S  L  L  V  I  V  F  I  I  I  V  L  Y  M  L] R  F  K  K  Y  180

541 AAGCAAGCTGGGAGCCATTCCAATTCTTTCCGCTTATCCAACGGCCGCACTGAGGATGTG 600
181  K  Q  A  G  S  H  S  N  S  F  R  L  S  N  G  R  T  E  D  V  200

601 GAGCCCCAGAGTGTGCCACTTCTGGCCAGATCCCCAAGCACCAACAGGAAATACCCACCC 660
201  E  P  Q  S  V  P  L  L  A  R  S  P  S  T  N  R  K  Y  P  P  220

661 CTGCCCGTGGACAAGCTGGAAGAGGAAATTAACCGGAGAATGGCAGACGACAATAAGCTC 720
221  L  P  V  D  K  L  E  E  E  I  N  R  R  M  A  D  D  N  K  L  240

721 TTCAGGGAGGAATTCAACGCTCTCCCTGCATGTCCTATCCAGGCCACCTGTGAGGCTGCT 780
241  F  R  E  E  F  N  A  L  P  A  C  P  I  Q  A  T  C  E  A  A  260

781 TCCAAGGAGGAAAACAAGGAAAAAAATCGATATGTAAACATCTTGCCTTATGACCACTCT 840
261  S  K  E  E [N  K  E  K  N  R  Y  V  N  I  L  P  Y  D  H  S  280
                PTPase DOMAIN I
```

FIG.8A

```
841  AGAGTCCACCTGACACCGGTTGAAGGGGTTCCAGATTCTGATTACATCAATGCTTCATTC  900
281  R  V  H  L  T  P  V  E  G  V  P  D  S  D  Y  I  N  A  S  F   300

901  ATCAACGGTTACCAAGAAAAGAACAAATTCATTGCTGCACAAGGACCAAAAGAAGAAACG  960
301  I  N  G  Y  Q  E  K  N  K  F  I  A  A  Q  G  P  K  E  E  T   320

961  GTGAATGATTTCTGGCGGATGATCTGGGAACAAAACACAGCCACCATCGTCATGGTTACC  1020
321  V  N  D  F  W  R  M  I  W  E  Q  N  T  A  T  I  V  M  V  T   340

1021 AACCTGAAGGAGAGAAAGGAGTGCAAGTGCGCCCAGTACTGGCCAGACCAAGGCTGCTGG  1080
341  N  L  K  E  R  K  E  C  K  C  A  Q  Y  W  P  D  Q  G  C  W   360

1081 ACCTATGGGAATATTCGGGTGTCTGTAGAGGATGTGACTGTCCTGGTGGACTACACAGTA  1140
361  T  Y  G  N  I  R  V  S  V  E  D  V  T  V  L  V  D  Y  T  V   380

1141 CGGAAGTTCTGCATCCAGCAGGTGGGCGACATGACCAACAGAAAGCCACAGCGCCTCATC  1200
381  R  K  F  C  I  Q  Q  V  G  D  M  T  N  R  K  P  Q  R  L  I   400

1201 ACTCAGTTCCACTTTACCAGCTGGCCAGACTTTGGGGTGCCTTTTACCCCGATCGGCATG  1260
401  T  Q  F  H  F  T  S  W  P  D  F  G  V  P  F  T  P  I  G  M   420

1261 CTCAAGTTCCTCAAGAAGGTGAAGGCCTGTAACCCTCAGTATGCAGGGGCCATCGTGGTC  1320
421  L  K  F  L  K  K  V  K  A  C  N  P  Q  Y  A  G  A  I  V  V   440

1321 CACTGCAGTGCAGGTGTAGGGCGTACAGGTACCTTTGTCGTCATTGATGCCATGCTGGAC  1380
441  H  C  S  A  G  V  G  R  T  G  T  F  V  V  I  D  A  M  L  D   460

1381 ATGATGCATACAGAACGGAAGGTGGACGTGTATGGCTTTGTGAGCCGGATCCGGGCACAG  1440
461  M  M  H  T  E  R  K  V  D  V  Y  G  F  V  S  R  I  R  A  Q   480

1441 CGCTGCCAGATGGTGCAAACCGATATGCAGTATGTCTTCATATACCAAGCCCTTCTGGAG  1500
481  R  C  Q  M  V  Q  T  D  M  Q  Y  V  F  I  Y  Q  A  L  L  E]  500

1501 CATTATCTCTATGGAGATACAGAACTGGAAGTGACCTCTCTAGAAACCCACCTGCAGAAA  1560
501  H  Y  L  Y  G  D  T  E  L  E  V  T  S  L  E  T  H  L  Q  K   520

1561 ATTTACAACAAAATCCCAGGGACCAGCAACAATGGATTAGAGGAGGAGTTTAAGAAGTTA  1620
521  I  Y  N  K  I  P  G  T  S  N  N  G  L  E  E  E  F  K  K  L   540
```

FIG. 8B

```
1621 ACATCAATCAAAATCCAGAATGACAAGATGCGGACTGGAAACCTTCCAGCCAACATGAAG 1680
 541  T  S  I  K  I  Q  N  D  K  M  R  T  G  N  L  P  A [N  M  K   560

1681 AAGAACCGTGTTTTACAGATCATTCCATATGAATTCAACAGAGTGATCATTCCAGTTAAG 1740
 561  K  N  R  V  L  Q  I  I  P  Y  E  F  N  R  V  I  I  P  V  K   580

1741 CGGGGCGAAGAGAATACAGACTATGTGAACGCATCCTTTATTGATGGCTACCGGCAGAAG 1800
 581  R  G  E  E  N  T  D  Y  V  N  A  S  F  I  D  G  Y  R  Q  K   600

1801 GACTCCTATATCGCCAGCCAGGGCCCTCTTCTCCACACAATTGAGGACTTCTGGCGAATG 1860
 601  D  S  Y  I  A  S  Q  G  P  L  L  H  T  I  E  D  F  W  R  M   620

1861 ATCTGGGAGTGGAAATCCTGCTCTATCGTGATGCTAACAGAACTGGAGGAGAGAGGCCAG 1920
 621  I  W  E  W  K  S  C  S  I  V  M  L  T  E  L  E  E  R  G  Q   640

1921 GAGAAGTGTGCCCAGTACTGGCCATCTGATGGACTGGTGTCCTATGGAGATATTACAGTG 1980
 641  E  K  C  A  Q  Y  W  P  S  D  G  L  V  S  Y  G  D  I  T  V   660

1981 GAACTGAAGAAGGAGGAGGAATGTGAGAGCTACACCGTCCGAGACCTCCTGGTCACCAAC 2040
 661  E  L  K  K  E  E  E  C  E  S  Y  T  V  R  D  L  L  V  T  N   680

2041 ACCAGGGAGAATAAGAGCCGGCAGATCCGGCAGTTCCACTTCCATGGCTGGCCTGAAGTG 2100
 681  T  R  E  N  K  S  R  Q  I  R  Q  F  H  F  H  G  W  P  E  V   700

2101 GGCATCCCCAGTGACGGAAAGGGCATGATCAGCATCATCGCCGCCGTGCAGAAGCAGCAG 2160
 701  G  I  P  S  D  G  K  G  M  I  S  I  I  A  A  V  Q  K  Q  Q   720

2161 CAGCAGTCAGGGAACCACCCCATCACCGTGCACTGCAGCGCCGGGGCAGGAAGGACGGGG 2220
 721  Q  Q  S  G  N  H  P  I  T  V  H  C  S  A  G  A  G  R  T  G   740

2221 ACCTTCTGTGCCCTGAGCACCGTCCTGGAGCGTGTGAAAGCAGAGGGGATTTTGGATGTC 2280
 741  T  F  C  A  L  S  T  V  L  E  R  V  K  A  E  G  I  L  D  V   760

2281 TTCCAGACTGTCAAGAGCCTGCGGCTACAGAGGCCACACATGGTCCAGACACTGGAACAG 2340
 761  F  Q  T  V  K  S  L  R  L  Q  R  P  H  M  V  Q  T  L  E  Q   780

2341 TATGAGTTCTGCTACAAGGTGGTGCAGGAGTATATTGATGCATTCTCAGATTATGCCAAC 2400
 781  Y  E  F  C  Y  K  V  V  Q  E] Y  I  D  A  F  S  D  Y  A  N   800

2401 TTCAAGTAA 2409
 801  F  K  *   803
```

FIG.8C

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
( A ) LENGTH: 802 amino acids
( B ) TYPE: amino acid
( D ) TOPOLOGY: linear ( i i ) MOLECULE TYPE: protein ( x i ) SEQUENCE DESCRIPTION: SEQ ID NO:1:

| Met | Asp | Ser | Trp | Phe | Ile | Leu | Val | Leu | Leu | Gly | Ser | Gly | Leu | Ile | Cys |
|---|---|---|---|---|---|---|---|---|---|---|---|---|---|---|---|
| 1 | | | | 5 | | | | | 10 | | | | | 15 | |
| Val | Ser | Ala | Asn | Asn | Ala | Thr | Thr | Val | Ala | Pro | Ser | Val | Gly | Ile | Thr |
| | | | 20 | | | | | 25 | | | | | 30 | | |
| Arg | Leu | Ile | Asn | Ser | Ser | Thr | Ala | Glu | Pro | Val | Lys | Glu | Glu | Ala | Lys |
| | | | 35 | | | | 40 | | | | | 45 | | | |
| Thr | Ser | Asn | Pro | Thr | Ser | Ser | Leu | Thr | Ser | Leu | Ser | Val | Ala | Pro | Thr |
| | 50 | | | | | 55 | | | | | 60 | | | | |
| Phe | Ser | Pro | Asn | Ile | Thr | Leu | Gly | Pro | Thr | Tyr | Leu | Thr | Thr | Val | Asn |
| 65 | | | | | 70 | | | | | 75 | | | | | 80 |
| Ser | Ser | Asp | Ser | Asp | Asn | Gly | Thr | Thr | Arg | Thr | Ala | Ser | Thr | Asn | Ser |
| | | | | 85 | | | | | 90 | | | | | 95 | |
| Ile | Gly | Ile | Thr | Ile | Ser | Pro | Asn | Gly | Thr | Trp | Leu | Pro | Asp | Asn | Gln |
| | | | 100 | | | | | 105 | | | | | 110 | | |
| Phe | Thr | Asp | Ala | Arg | Thr | Glu | Pro | Trp | Glu | Gly | Asn | Ser | Ser | Thr | Ala |
| | | | 115 | | | | 120 | | | | | 125 | | | |
| Ala | Thr | Thr | Pro | Glu | Thr | Phe | Pro | Pro | Ser | Gly | Asn | Ser | Asp | Ser | Lys |
| | | 130 | | | | | 135 | | | | | 140 | | | |
| Asp | Arg | Arg | Asp | Glu | Thr | Pro | Ile | Ile | Ala | Val | Met | Val | Ala | Leu | Ser |
| 145 | | | | | 150 | | | | | 155 | | | | | 160 |
| Ser | Leu | Leu | Val | Ile | Val | Phe | Ile | Ile | Ile | Val | Leu | Tyr | Met | Leu | Arg |
| | | | | 165 | | | | | 170 | | | | | 175 | |
| Phe | Lys | Lys | Tyr | Lys | Gln | Ala | Gly | Ser | His | Ser | Asn | Ser | Phe | Arg | Leu |
| | | | 180 | | | | | 185 | | | | | 190 | | |
| Ser | Asn | Gly | Arg | Thr | Glu | Asp | Val | Glu | Pro | Gln | Ser | Val | Pro | Leu | Leu |
| | | | 195 | | | | 200 | | | | | 205 | | | |
| Ala | Arg | Ser | Pro | Ser | Thr | Asn | Arg | Lys | Tyr | Pro | Pro | Leu | Pro | Val | Asp |
| | 210 | | | | | 215 | | | | | 220 | | | | |
| Lys | Leu | Glu | Glu | Glu | Ile | Asn | Arg | Arg | Met | Ala | Asp | Asp | Asn | Lys | Leu |
| 225 | | | | | 230 | | | | | 235 | | | | | 240 |
| Phe | Arg | Glu | Glu | Phe | Asn | Ala | Leu | Pro | Ala | Cys | Pro | Ile | Gln | Ala | Thr |
| | | | | 245 | | | | | 250 | | | | | 255 | |
| Cys | Glu | Ala | Ala | Ser | Lys | Glu | Glu | Asn | Lys | Glu | Lys | Asn | Arg | Tyr | Val |
| | | | 260 | | | | | 265 | | | | | 270 | | |
| Asn | Ile | Leu | Pro | Tyr | Asp | His | Ser | Arg | Val | His | Leu | Thr | Pro | Val | Glu |
| | | | 275 | | | | 280 | | | | | 285 | | | |
| Gly | Val | Pro | Asp | Ser | Asp | Tyr | Ile | Asn | Ala | Ser | Phe | Ile | Asn | Gly | Tyr |
| | | 290 | | | | | 295 | | | | | 300 | | | |
| Gln | Glu | Lys | Asn | Lys | Phe | Ile | Ala | Ala | Gln | Gly | Pro | Lys | Glu | Glu | Thr |
| 305 | | | | | 310 | | | | | 315 | | | | | 320 |
| Val | Asn | Asp | Phe | Trp | Arg | Met | Ile | Trp | Glu | Gln | Asn | Thr | Ala | Thr | Ile |

-continued

|     |     |     |     |     | 325 |     |     |     |     | 330 |     |     |     |     | 335 |     |
|-----|-----|-----|-----|-----|-----|-----|-----|-----|-----|-----|-----|-----|-----|-----|-----|-----|

Val Met Val Thr Asn Leu Lys Glu Arg Lys Glu Cys Lys Cys Ala Gln
                340                         345                350

Tyr Trp Pro Asp Gln Gly Cys Trp Thr Tyr Gly Asn Ile Arg Val Ser
            355                 360                 365

Val Glu Asp Val Thr Val Leu Val Asp Tyr Thr Val Arg Lys Phe Cys
        370                 375                 380

Ile Gln Gln Val Gly Asp Met Thr Asn Arg Lys Pro Gln Arg Leu Ile
385                     390                 395                     400

Thr Gln Phe His Phe Thr Ser Trp Pro Asp Phe Gly Val Pro Phe Thr
                405                 410                 415

Pro Ile Gly Met Leu Lys Phe Leu Lys Lys Val Lys Ala Cys Asn Pro
            420                 425                 430

Gln Tyr Ala Gly Ala Ile Val Val His Cys Ser Ala Gly Val Gly Arg
        435                 440                 445

Thr Gly Thr Phe Val Val Ile Asp Ala Met Leu Asp Met Met His Thr
    450                 455                 460

Glu Arg Lys Val Asp Val Tyr Gly Phe Val Ser Arg Ile Arg Ala Gln
465                 470                 475                 480

Arg Cys Gln Met Val Gln Thr Asp Met Gln Tyr Val Phe Ile Tyr Gln
                485                 490                 495

Ala Leu Leu Glu His Tyr Leu Tyr Gly Asp Thr Glu Leu Glu Val Thr
            500                 505                 510

Ser Leu Glu Thr His Leu Gln Lys Ile Tyr Asn Lys Ile Pro Gly Thr
            515                 520                 525

Ser Asn Asn Gly Leu Glu Glu Phe Lys Lys Leu Thr Ser Ile Lys
    530                 535                 540

Ile Gln Asn Asp Lys Met Arg Thr Gly Asn Leu Pro Ala Asn Met Lys
545                 550                 555                     560

Lys Asn Arg Val Leu Gln Ile Ile Pro Tyr Glu Phe Asn Arg Val Ile
                565                 570                 575

Ile Pro Val Lys Arg Gly Glu Glu Asn Thr Asp Tyr Val Asn Ala Ser
            580                 585                 590

Phe Ile Asp Gly Tyr Arg Gln Lys Asp Ser Tyr Ile Ala Ser Gln Gly
        595                 600                 605

Pro Leu Leu His Thr Ile Glu Asp Phe Trp Arg Met Ile Trp Glu Trp
    610                 615                 620

Lys Ser Cys Ser Ile Val Met Leu Thr Glu Leu Glu Glu Arg Gly Gln
625                 630                 635                     640

Glu Lys Cys Ala Gln Tyr Trp Pro Ser Asp Gly Leu Val Ser Tyr Gly
            645                 650                 655

Asp Ile Thr Val Glu Leu Lys Lys Glu Glu Cys Glu Ser Tyr Thr
            660                 665                 670

Val Arg Asp Leu Leu Val Thr Asn Thr Arg Glu Asn Lys Ser Arg Gln
        675                 680                 685

Ile Arg Gln Phe His Phe His Gly Trp Pro Glu Val Gly Ile Pro Ser
    690                 695                 700

Asp Gly Lys Gly Met Ile Ser Ile Ile Ala Ala Val Gln Lys Gln Gln
705                 710                 715                     720

Gln Gln Ser Gly Asn His Pro Ile Thr Val His Cys Ser Ala Gly Ala
                725                 730                 735

Gly Arg Thr Gly Thr Phe Cys Ala Leu Ser Thr Val Leu Glu Arg Val
            740                 745                 750

-continued

| Lys | Ala | Glu | Gly | Ile | Leu | Asp | Val | Phe | Gln | Thr | Val | Lys | Ser | Leu | Arg |
|---|---|---|---|---|---|---|---|---|---|---|---|---|---|---|---|
|   |   | 755 |   |   |   | 760 |   |   |   |   |   | 765 |   |   |   |

| Leu | Gln | Arg | Pro | His | Met | Val | Gln | Thr | Leu | Glu | Gln | Tyr | Glu | Phe | Cys |
|---|---|---|---|---|---|---|---|---|---|---|---|---|---|---|---|
|   |   | 770 |   |   |   | 775 |   |   |   |   |   | 780 |   |   |   |

| Tyr | Lys | Val | Val | Gln | Glu | Tyr | Ile | Asp | Ala | Phe | Ser | Asp | Tyr | Ala | Asn |
|---|---|---|---|---|---|---|---|---|---|---|---|---|---|---|---|
| 785 |   |   |   |   | 790 |   |   |   |   | 795 |   |   |   |   | 800 |

Phe Lys ( 2 ) INFORMATION FOR SEQ ID NO:2:

( i ) SEQUENCE CHARACTERISTICS:
        ( A ) LENGTH: 2409 base pairs
        ( B ) TYPE: nucleic acid
        ( C ) STRANDEDNESS: double
        ( D ) TOPOLOGY: unknown ( i i ) MOLECULE TYPE: cDNA ( x i ) SEQUENCE DESCRIPTION: SEQ ID NO:2:

```
ATGGATTCCT GGTTCATTCT TGTTCTGCTC GGCAGTGGTC TGATATGTGT CAGTGCCAAC    60
AATGCTACCA CAGTTGCACC TTCTGTAGGA ATTACAAGAT TAATTAACTC ATCAACGGCA   120
GAACCAGTTA AGAAGAGGC CAAAACTTCA AATCCAACTT CTTCACTAAC TTCTCTTTCT   180
GTGGCACCAA CATTCAGCCC AAATATAACT CTGGGACCCA CCTATTTAAC CACTGTCAAT   240
TCTTCAGACT CTGACAATGG GACCACAAGA ACAGCAAGCA CCAATTCTAT AGGCATTACA   300
ATTTCACCAA ATGGAACGTG GCTTCCAGAT AACCAGTTCA CGGATGCCAG AACAGAACCC   360
TGGGAGGGGA ATTCCAGCAC CGCAGCAACC ACTCCAGAAA CTTTCCCTCC TTCAGGTAAT   420
TCTGACTCGA AGGACAGAAG AGATGAGACA CCAATTATTG CGGTGATGGT GGCCCTGTCC   480
TCTCTGCTAG TGATCGTGTT TATTATCATA GTTTTGTACA TGTTAAGGTT TAAGAAATAC   540
AAGCAAGCTG GGAGCCATTC CAATTCTTTC CGCTTATCCA ACGGCCGCAC TGAGGATGTG   600
GAGCCCCAGA GTGTGCCACT TCTGGCCAGA TCCCCAAGCA CCAACAGGAA ATACCCACCC   660
CTGCCCGTGG ACAAGCTGGA AGAGGAAATT AACCGGAGAA TGGCAGACGA CAATAAGCTC   720
TTCAGGGAGG AATTCAACGC TCTCCCTGCA TGTCCTATCC AGGCCACCTG TGAGGCTGCT   780
TCCAAGGAGG AAAACAAGGA AAAAAATCGA TATGTAAACA TCTTGCCTTA TGACCACTCT   840
AGAGTCCACC TGACACCGGT TGAAGGGGTT CCAGATTCTG ATTACATCAA TGCTTCATTC   900
ATCAACGGTT ACCAAGAAAA GAACAAATTC ATTGCTGCAC AAGGACCAAA AGAAGAAACG   960
GTGAATGATT TCTGGCGGAT GATCTGGGAA CAAAACACAG CCACCATCGT CATGGTTACC  1020
AACCTGAAGG AGAGAAAGGA GTGCAAGTGC GCCCAGTACT GGCCAGACCA AGGCTGCTGG  1080
ACCTATGGGA ATATTCGGGT GTCTGTAGAG GATGTGACTG TCCTGGTGGA CTACACAGTA  1140
CGGAAGTTCT GCATCCAGCA GGTGGGCGAC ATGACCAACA GAAAGCCACA GCGCCTCATC  1200
ACTCAGTTCC ACTTTACCAG CTGGCCAGAC TTTGGGGTGC CTTTTACCCC GATCGGCATG  1260
CTCAAGTTCC TCAAGAAGGT GAAGGCCTGT AACCCTCAGT ATGCAGGGGC CATCGTGGTC  1320
CACTGCAGTG CAGGTGTAGG GCGTACAGGT ACCTTTGTCG TCATTGATGC CATGCTGGAC  1380
ATGATGCATA CAGAACGGAA GGTGGACGTG TATGGCTTTG TGAGCCGGAT CCGGGCACAG  1440
CGCTGCCAGA TGGTGCAAAC CGATATGCAG TATGTCTTCA TATACCAAGC CCTTCTGGAG  1500
CATTATCTCT ATGGAGATAC AGAACTGGAA GTGACCTCTC TAGAAACCCA CCTGCAGAAA  1560
ATTTACAACA AAATCCCAGG GACCAGCAAC AATGGATTAG AGGAGGAGTT TAAGAAGTTA  1620
ACATCAATCA AATCCAGAA TGACAAGATG CGGACTGGAA ACCTTCCAGC CAACATGAAG  1680
```

| | | | | | | |
|---|---|---|---|---|---|---|
| AAGAACCGTG | TTTTACAGAT | CATTCCATAT | GAATTCAACA | GAGTGATCAT | TCCAGTTAAG | 1740 |
| CGGGGCGAAG | AGAATACAGA | CTATGTGAAC | GCATCCTTTA | TTGATGGCTA | CCGGCAGAAG | 1800 |
| GACTCCTATA | TCGCCAGCCA | GGGCCCTCTT | CTCCACACAA | TTGAGGACTT | CTGGCGAATG | 1860 |
| ATCTGGGAGT | GGAAATCCTG | CTCTATCGTG | ATGCTAACAG | AACTGGAGGA | GAGAGGCCAG | 1920 |
| GAGAAGTGTG | CCCAGTACTG | GCCATCTGAT | GGACTGGTGT | CCTATGGAGA | TATTACAGTG | 1980 |
| GAACTGAAGA | AGGAGGAGGA | ATGTGAGAGC | TACACCGTCC | GAGACCTCCT | GGTCACCAAC | 2040 |
| ACCAGGGAGA | ATAAGAGCCG | GCAGATCCGG | CAGTTCCACT | CCATGGCTG | CCTGAAGTG | 2100 |
| GGCATCCCCA | GTGACGGAAA | GGGCATGATC | AGCATCATCG | CCGCCGTGCA | GAAGCAGCAG | 2160 |
| CAGCAGTCAG | GAACCACCC | CATCACCGTG | CACTGCAGCG | CCGGGGCAGG | AAGGACGGGG | 2220 |
| ACCTTCTGTG | CCCTGAGCAC | CGTCCTGGAG | CGTGTGAAAG | CAGAGGGGAT | TTTGGATGTC | 2280 |
| TTCCAGACTG | TCAAGAGCCT | GCGGCTACAG | AGGCCACACA | TGGTCCAGAC | ACTGGAACAG | 2340 |
| TATGAGTTCT | GCTACAAGGT | GGTGCAGGAG | TATATTGATG | CATTCTCAGA | TTATGCCAAC | 2400 |
| TTCAAGTAA | | | | | | 2409 |

( 2 ) INFORMATION FOR SEQ ID NO:3:

( i ) SEQUENCE CHARACTERISTICS:
( A ) LENGTH: 793 amino acids
( B ) TYPE: amino acid
( D ) TOPOLOGY: linear ( i i ) MOLECULE TYPE: protein ( x i ) SEQUENCE DESCRIPTION: SEQ ID NO:3:

```
Met Asp Ser Trp Phe Ile Leu Val Leu Phe Gly Ser Gly Leu Ile His
 1               5                  10                  15
Val Ser Ala Asn Asn Ala Thr Thr Val Ser Pro Ser Leu Gly Thr Thr
                20                  25                  30
Arg Leu Ile Lys Thr Ser Thr Glu Leu Ala Lys Glu Asn Lys
            35                  40                  45
Thr Ser Asn Ser Thr Ser Ser Val Ile Ser Leu Ser Val Ala Pro Thr
        50                  55                  60
Phe Ser Pro Asn Leu Thr Leu Glu Pro Thr Tyr Val Thr Thr Val Asn
 65                  70                  75                  80
Ser Ser His Ser Asp Asn Gly Thr Arg Arg Ala Ala Ser Thr Glu Ser
                85                  90                  95
Gly Gly Thr Thr Ile Ser Pro Asn Gly Ser Trp Leu Ile Glu Asn Gln
            100                 105                 110
Phe Thr Asp Ala Ile Thr Glu Pro Trp Glu Gly Asn Ser Ser Thr Ala
        115                 120                 125
Ala Thr Thr Pro Glu Thr Phe Pro Pro Ala Asp Glu Thr Pro Ile Ile
130                 135                 140
Ala Val Met Val Ala Leu Ser Ser Leu Leu Val Ile Val Phe Ile Ile
145                 150                 155                 160
Ile Val Leu Tyr Met Leu Arg Phe Lys Lys Tyr Lys Gln Ala Gly Ser
                165                 170                 175
His Ser Asn Ser Phe Arg Leu Ser Asn Gly Arg Thr Glu Asp Val Glu
            180                 185                 190
Pro Gln Ser Val Pro Leu Leu Ala Arg Ser Pro Ser Thr Asn Arg Lys
        195                 200                 205
Tyr Pro Pro Leu Pro Val Asp Lys Leu Glu Glu Glu Ile Asn Arg Arg
210                 215                 220
```

| | | | | | | | | | | | | | | |
|---|---|---|---|---|---|---|---|---|---|---|---|---|---|---|
| Met 225 | Ala | Asp | Asp | Asn | Lys 230 | Leu | Phe | Arg | Glu 235 | Glu | Phe | Asn | Ala | Leu Pro 240 |
| Ala | Cys | Pro | Ile | Gln 245 | Ala | Thr | Cys | Glu | Ala 250 | Ala | Ser | Lys | Glu | Glu Asn 255 |
| Lys | Glu | Lys | Asn 260 | Arg | Tyr | Val | Asn | Ile 265 | Leu | Pro | Tyr | Asp 270 | His | Ser Arg |
| Val | His | Leu 275 | Thr | Pro | Val | Glu | Gly 280 | Val | Pro | Asp | Ser 285 | Asp | Tyr | Ile Asn |
| Ala | Ser 290 | Phe | Ile | Asn | Gly | Tyr 295 | Gln | Glu | Lys | Asn 300 | Lys | Phe | Ile | Ala Ala |
| Gln 305 | Gly | Pro | Lys | Glu | Glu 310 | Thr | Val | Asn | Asp 315 | Phe | Trp | Arg | Met | Ile Trp 320 |
| Glu | Gln | Asn | Thr | Ala 325 | Thr | Ile | Val | Met | Val 330 | Thr | Asn | Leu | Lys | Glu Arg 335 |
| Lys | Glu | Cys | Lys 340 | Cys | Ala | Gln | Tyr | Trp 345 | Pro | Asp | Gln | Gly 350 | Cys | Trp Thr |
| Tyr | Gly | Asn 355 | Val | Arg | Val | Ser | Val 360 | Glu | Asp | Val | Thr 365 | Val | Leu | Val Asp |
| Tyr | Thr 370 | Val | Arg | Lys | Phe | Ser 375 | Ile | Gln | Gln | Val 380 | Gly | Asp | Val | Thr Asn |
| Arg 385 | Lys | Pro | Gln | Arg | Leu 390 | Ile | Thr | Gln | Phe 395 | His | Phe | Thr | Ser | Trp Pro 400 |
| Asp | Phe | Gly | Val | Pro 405 | Phe | Thr | Pro | Ile | Gly 410 | Met | Leu | Lys | Phe | Leu Lys 415 |
| Lys | Val | Lys | Ala 420 | Cys | Asn | Pro | Gln | Tyr 425 | Ala | Gly | Ala | Ile | Val 430 | Val His |
| Cys | Ser | Ala 435 | Gly | Val | Gly | Arg | Thr 440 | Gly | Thr | Phe | Val | Val 445 | Ile | Asp Ala |
| Met 450 | Leu | Asp | Met | Met | His 455 | Ser | Glu | Arg | Lys 460 | Val | Asp | Val | Tyr | Gly Phe |
| Val 465 | Ser | Arg | Ile | Arg | Ala 470 | Gln | Arg | Cys | Gln 475 | Met | Val | Gln | Thr | Asp Met 480 |
| Gln | Tyr | Val | Phe | Ile 485 | Tyr | Gln | Ala | Leu | Leu 490 | Glu | His | Tyr | Leu | Tyr Gly 495 |
| Asp | Thr | Glu | Leu 500 | Glu | Val | Thr | Ser | Leu 505 | Glu | Thr | His | Leu | Gln 510 | Lys Ile |
| Tyr | Asn | Lys 515 | Ile | Pro | Gly | Thr | Ser 520 | Asn | Asn | Gly | Leu | Glu 525 | Glu | Glu Phe |
| Lys 530 | Lys | Leu | Thr | Ser | Ile 535 | Lys | Ile | Gln | Asn | Asp 540 | Lys | Met | Arg | Thr Gly |
| Asn 545 | Leu | Pro | Ala | Asn | Met 550 | Lys | Lys | Asn | Arg | Val 555 | Leu | Gln | Ile | Ile Pro 560 |
| Tyr | Glu | Phe | Asn | Arg 565 | Val | Ile | Ile | Pro | Val 570 | Lys | Arg | Gly | Glu | Glu Asn 575 |
| Thr | Asp | Tyr | Val 580 | Asn | Ala | Ser | Phe | Ile 585 | Asp | Gly | Tyr | Arg | Gln 590 | Lys Asp |
| Ser | Tyr | Ile 595 | Ala | Ser | Gln | Gly | Pro 600 | Leu | Leu | His | Thr | Ile 605 | Glu | Asp Phe |
| Trp | Arg 610 | Met | Ile | Trp | Glu | Trp 615 | Lys | Ser | Cys | Ser | Ile 620 | Val | Met | Leu Thr |
| Glu 625 | Leu | Glu | Glu | Arg | Gly 630 | Gln | Glu | Lys | Cys 635 | Ala | Gln | Tyr | Trp | Pro Ser 640 |
| Asp | Gly | Leu | Val | Ser 645 | Tyr | Gly | Asp | Ile | Thr 650 | Val | Glu | Leu | Lys | Lys Glu 655 |

| | | | | | | | | | | | | | | |
|---|---|---|---|---|---|---|---|---|---|---|---|---|---|---|
| Glu | Glu | Cys | Glu | Ser | Tyr | Thr | Val | Arg | Asp | Leu | Leu | Val | Thr | Asn | Thr |
| | | | 660 | | | | | 665 | | | | 670 | | |
| Arg | Glu | Asn | Lys | Ser | Arg | Gln | Ile | Arg | Gln | Phe | His | Phe | His | Gly | Trp |
| | | 675 | | | | | 680 | | | | 685 | | | | |
| Pro | Glu | Val | Gly | Ile | Pro | Ser | Asp | Gly | Lys | Gly | Met | Ile | Asn | Ile | Ile |
| | 690 | | | | | 695 | | | | 700 | | | | | |
| Ala | Ala | Val | Gln | Lys | Gln | Gln | Gln | Ser | Gly | Asn | His | Pro | Ile | Thr |
| 705 | | | | | 710 | | | | 715 | | | | | 720 |
| Val | His | Cys | Ser | Ala | Gly | Ala | Gly | Arg | Thr | Gly | Thr | Phe | Cys | Ala | Leu |
| | | | | 725 | | | | | 730 | | | | | 735 | |
| Ser | Thr | Val | Leu | Glu | Arg | Val | Lys | Ala | Glu | Gly | Ile | Leu | Asp | Val | Phe |
| | | | 740 | | | | | 745 | | | | | 750 | | |
| Gln | Thr | Val | Lys | Ser | Leu | Arg | Leu | Gln | Arg | Pro | His | Met | Val | Gln | Thr |
| | | 755 | | | | | 760 | | | | 765 | | | | |
| Leu | Glu | Gln | Tyr | Glu | Phe | Cys | Tyr | Lys | Val | Val | Gln | Glu | Tyr | Ile | Asp |
| | 770 | | | | | 775 | | | | 780 | | | | | |
| Ala | Phe | Ser | Asp | Tyr | Ala | Asn | Phe | Lys |
| 785 | | | | 790 | | | | |

( 2 ) INFORMATION FOR SEQ ID NO:4:

( i ) SEQUENCE CHARACTERISTICS:
        ( A ) LENGTH: 2872 base pairs
        ( B ) TYPE: nucleic acid
        ( C ) STRANDEDNESS: double
        ( D ) TOPOLOGY: unknown ( i i ) MOLECULE TYPE: cDNA ( x i ) SEQUENCE DESCRIPTION: SEQ ID NO:4:

```
GAATTCCGGC GAGTGAGGCG CTGACAGGGA CTCGCGGGGG CATCTTGCAC AGACCCCTGG      60
ACCACGCCGC CATCGCAGCC TCCAGCCCAG TCCTCTCTCT GCCGCTTCTC CTCGCCATGG     120
AGGCCGCCGA CCGCCGTCCG CGGGCTTCGA GCAGCGGACC GGGCCGGGCT GACCCCATGT     180
GGGCCGAGAG CCCGGTCCTG AGGCGGAGCT GCCGTGCGCG TCCCCGCGG  TCCCGCCCCA     240
GCGCCGGGCT CGGTCAGCAT GGATTCCTGG TTCATTCTTG TCCTGTTTGG CAGTGGTCTA     300
ATACATGTTA GTGCCAACAA TGCTACTACA GTTTCACCTT CTTTAGGAAC GACAAGATTA     360
ATTAAAACAT CAACAACAGA ATTGGCTAAG GAAGAGAATA AACCTCAAA  TTCAACCTCT     420
TCAGTAATTT CTCTTTCTGT GGCACCAACA TTCAGCCCAA ACCTGACTCT GGAGCCCACC     480
TATGTGACTA CTGTTAATTC TTCACACTCT GACAATGGGA CCAGGAGGGC AGCCAGCACG     540
GAATCTGGAG GCACTACCAT TTCCCCGAAC GGAAGCTGGC TTATTGAGAA CCAGTTCACG     600
GATGCCATAA CAGAACCCTG GAGGGGAAC  TCCAGCACTG CAGCAACCAC TCCAGAAACC     660
TTCCCCCCGG CAGATGAGAC ACCAATTATT GCGGTGATGG TGGCCCTGTC CTCTCTGCTA     720
GTAATCGTGT TTATTATCAT AGTTCTGTAC ATGTTAAGGT TTAAGAAATA CAAGCAAGCT     780
GGGAGTCATT CCAACTCTTT CCGCCTGTCA AATGGCCGCA CGGAGGATGT GGAGCCCCAA     840
AGTGTACCAC TTCTGGCCAG GTCCCCGAGC ACCAACAGGA AGTACCCACC ACTGCCTGTG     900
GACAAGCTGG AAGAGGAGAT TAACCGGAGA ATGGCTGATG ACAATAAGCT CTTCAGAGAA     960
GAATTCAACG CTCTCCCTGC TTGTCCTATC CAGGCCACCT GTGAGGCTGC CTCCAAGGAA    1020
GAAAACAAGG AAAAAAACCG CTATGTAAAC ATCCTGCCCT ATGACCACTC TAGAGTGCAC    1080
CTGACACCTG TTGAAGGGGT CCCAGATTCT GATTACATCA ACGCTTCATT CATTAATGGC    1140
TACCAGGAAA AGAACAAATT CATCGCTGCA CAAGGACCAA AAGAAGAAAC AGTGAATGAC    1200
```

-continued

| | | | | | |
|---|---|---|---|---|---|
| TTCTGGAGAA | TGATATGGGA | ACAAAACACA | GCTACTATTG | TCATGGTGAC | CAACCTGAAG | 1260 |
| GAGAGAAAGG | AGTGTAAATG | TGCCCAATAC | TGGCCAGACC | AAGGCTGCTG | GACCTATGGG | 1320 |
| AATGTCCGTG | TGTCTGTCGA | GGATGTGACT | GTTCTGGTGG | ACTACACAGT | ACGGAAATTC | 1380 |
| TCGATCCAGC | AGGTGGGCGA | CGTGACCAAC | AGGAAACCAC | AGCGCCTCAT | CACTCAGTTC | 1440 |
| CACTTCACCA | GCTGGCCAGA | CTTTGGGGTG | CCTTTCACCC | CAATTGGCAT | GCTCAAGTTC | 1500 |
| CTCAAGAAGG | TGAAGGCCTG | TAACCCTCAG | TACGCAGGGG | CTATCGTGGT | CCACTGCAGT | 1560 |
| GCAGGTGTAG | GGCGCACTGG | CACCTTTGTT | GTCATCGATG | CCATGCTGGA | CATGATGCAT | 1620 |
| TCGGAGCGCA | AAGTGGATGT | ATATGGGTTT | GTGAGCCGGA | TCCGGGCCCA | GCGCTGCCAG | 1680 |
| ATGGTACAGA | CAGACATGCA | GTACGTCTTC | ATATACCAGG | CCCTTCTGGA | GCATTATCTG | 1740 |
| TATGGGGACA | CAGAACTGGA | AGTGACTTCT | CTAGAAACCC | ACCTACAAAA | AATTTATAAC | 1800 |
| AAGATCCCAG | GGACTAGCAA | CAACGGGTTA | GAGGAGGAGT | TTAAGAAATT | AACTTCAATC | 1860 |
| AAAATCCAGA | ATGACAAGAT | GCGCACGGGA | AACCTTCCAG | CCAACATGAA | GAAGAACCGG | 1920 |
| GTTTTACAGA | TCATTCCATA | TGAATTTAAC | AGAGTGATCA | TTCCAGTCAA | ACGAGGCGAA | 1980 |
| GAGAACACAG | ACTATGTGAA | CGCATCCTTC | ATTGATGGAT | ACCGGCAGAA | AGACTCCTAC | 2040 |
| ATTGCCAGCC | AGGGCCCTCT | TCTCCACACG | ATTGAGGACT | CTGGCGAAT | GATCTGGGAG | 2100 |
| TGGAAGTCCT | GTTCTATCGT | AATGCTGACA | GAACTGGAAG | AGAGAGGCCA | GGAGAAGTGT | 2160 |
| GCCCAGTACT | GGCCATCTGA | TGGCCTGGTG | TCCTACGGAG | ACATCACAGT | TGAGCTGAAG | 2220 |
| AAGGAGGAGG | AATGTGAAAG | CTACACTGTC | CGAGACCTCC | TGGTCACCAA | CACCAGGGAG | 2280 |
| AACAAGAGTC | GGCAAATCCG | GCAGTTCCAC | TTCCACGGCT | GGCCTGAGGT | GGGCATCCCC | 2340 |
| AGCGACGGCA | AGGGCATGAT | CAACATCATT | GCAGCAGTGC | AGAAGCAGCA | GCAGCAGTCG | 2400 |
| GGGAACCATC | CCATCACTGT | GCACTGCAGT | GCCGGGGCAG | GACGGACAGG | AACCTTCTGT | 2460 |
| GCCTTGAGCA | CAGTCCTGGA | ACGTGTGAAA | GCAGAAGGAA | TTTTAGATGT | CTTCCAAACT | 2520 |
| GTCAAGAGCC | TGCGGCTGCA | GAGGCCACAC | ATGGTCCAGA | CACTGGAACA | GTATGAATTC | 2580 |
| TGCTACAAGG | TGGTACAGGA | ATACATTGAC | GCCTTTTCAG | ATTATGCCAA | CTTCAAGTGA | 2640 |
| CAGGTGACAA | GGCCCACAGA | CAGGAGAATT | GCCTTTAATA | TTTTGTAATA | TTCTGTTTTT | 2700 |
| GTTAATATAC | CCAAAATTGT | ATATATCTTA | TAACTGTTTT | AGAAATGGCA | CATAGGCTTC | 2760 |
| TATTACCTGT | TAGATGGAGA | TTTTGTATGT | AAATGTGTTA | GCACTGATAG | TCCTTTTCCA | 2820 |
| GTGTTTTATT | GGGAAATTAA | TAGTGTGATA | TTTGGGTTGA | TATAATGAAT | TC | 2872 |

( 2 ) INFORMATION FOR SEQ ID NO:5:

( i ) SEQUENCE CHARACTERISTICS:
        ( A ) LENGTH: 235 amino acids
        ( B ) TYPE: amino acid
        ( C ) STRANDEDNESS: single
        ( D ) TOPOLOGY: unknown ( i i ) MOLECULE TYPE: protein ( x i ) SEQUENCE DESCRIPTION: SEQ ID NO:5:

```
Asn Gln Asn Lys Asn Arg Tyr Val Asp Ile Leu Pro Tyr Asp Tyr Asn
 1               5                  10                  15

Arg Val Glu Leu Ser Glu Ile Asn Gly Asp Ala Gly Ser Asn Tyr Ile
            20                  25                  30

Asn Ala Ser Tyr Ile Asp Gly Phe Lys Glu Pro Arg Lys Tyr Ile Ala
        35                  40                  45

Ala Gln Gly Pro Arg Asp Glu Thr Val Asp Asp Phe Trp Arg Met Ile
```

```
              50                      55                      60
Trp  Glu  Gln  Lys  Ala  Thr  Val  Ile  Val  Met  Val  Thr  Arg  Cys  Glu  Glu
65                      70                      75                       80

Gly  Asn  Arg  Asn  Lys  Cys  Ala  Glu  Tyr  Trp  Pro  Ser  Met  Glu  Glu  Gly
                85                      90                      95

Thr  Arg  Ala  Phe  Gly  Asp  Val  Val  Val  Lys  Ile  Asn  Gln  His  Lys  Arg
               100                     105                    110

Cys  Pro  Asp  Tyr  Ile  Ile  Gln  Lys  Leu  Asn  Ile  Val  Asn  Lys  Lys  Glu
               115                     120                    125

Lys  Ala  Thr  Gly  Arg  Glu  Val  Thr  His  Ile  Gln  Phe  Thr  Ser  Trp  Pro
130                     135                    140

Asp  His  Gly  Val  Pro  Glu  Asp  Pro  His  Leu  Leu  Leu  Lys  Leu  Arg  Arg
145                     150                    155                         160

Arg  Val  Asn  Ala  Phe  Ser  Asn  Phe  Phe  Ser  Gly  Pro  Ile  Val  Val  His
               165                     170                    175

Cys  Ser  Ala  Gly  Val  Gly  Arg  Thr  Gly  Thr  Tyr  Ile  Gly  Ile  Asp  Ala
               180                     185                    190

Met  Leu  Glu  Gly  Leu  Glu  Ala  Glu  Asn  Lys  Val  Asp  Val  Tyr  Gly  Tyr
               195                     200                    205

Val  Val  Lys  Leu  Arg  Arg  Gln  Arg  Cys  Leu  Met  Val  Gln  Val  Glu  Ala
          210                     215                    220

Gln  Tyr  Ile  Leu  Ile  His  Gln  Ala  Leu  Val  Glu
225                     230                    235
```

(2) INFORMATION FOR SEQ ID NO:6:

(i) SEQUENCE CHARACTERISTICS:
(A) LENGTH: 236 amino acids
(B) TYPE: amino acid
(C) STRANDEDNESS: single
(D) TOPOLOGY: unknown (ii) MOLECULE TYPE: protein (xi) SEQUENCE DESCRIPTION: SEQ ID NO:6:

```
Asn  Lys  Glu  Lys  Asn  Arg  Tyr  Val  Asn  Ile  Leu  Pro  Tyr  Asp  His  Ser
1                5                       10                     15

Arg  Val  His  Leu  Thr  Pro  Val  Glu  Gly  Val  Pro  Asp  Ser  Asp  Tyr  Ile
                20                      25                     30

Asn  Ala  Ser  Phe  Ile  Asn  Gly  Tyr  Gln  Glu  Lys  Asn  Lys  Phe  Ile  Ala
                35                      40                     45

Ala  Gln  Gly  Pro  Lys  Glu  Glu  Thr  Val  Asn  Asp  Phe  Trp  Arg  Met  Ile
     50                      55                      60

Trp  Glu  Gln  Asn  Thr  Ala  Thr  Ile  Val  Met  Val  Thr  Asn  Leu  Lys  Glu
65                      70                      75                      80

Arg  Lys  Glu  Cys  Lys  Cys  Ala  Gln  Tyr  Trp  Pro  Asp  Gln  Gly  Glu  Trp
                85                      90                     95

Thr  Tyr  Gly  Asn  Ile  Arg  Val  Ser  Val  Glu  Asp  Val  Thr  Val  Leu  Val
               100                     105                    110

Asp  Tyr  Thr  Val  Arg  Lys  Phe  Cys  Ile  Gln  Gln  Val  Gly  Asp  Met  Thr
               115                     120                    125

Asn  Arg  Lys  Pro  Gln  Arg  Leu  Ile  Thr  Gln  Phe  His  Phe  Thr  Ser  Trp
130                     135                    140

Pro  Asp  Phe  Gly  Val  Pro  Phe  Thr  Pro  Ile  Gly  Met  Leu  Lys  Phe  Leu
145                     150                    155                         160

Lys  Lys  Val  Lys  Ala  Cys  Asn  Pro  Gln  Tyr  Ala  Gly  Ala  Ile  Val  Val
               165                     170                    175
```

```
    His  Cys  Ser  Ala  Gly  Val  Gly  Arg  Thr  Gly  Thr  Phe  Val  Val  Ile  Asp
              180                      185                      190

Ala  Met  Leu  Asp  Met  Met  His  Thr  Glu  Arg  Lys  Val  Asp  Val  Tyr  Gly
         195                      200                      205

Phe  Val  Ser  Arg  Ile  Arg  Ala  Gln  Arg  Cys  Gln  Met  Val  Gln  Thr  Asp
    210                      215                      220

Met  Gln  Tyr  Val  Phe  Ile  Tyr  Gln  Ala  Leu  Leu  Glu
    225                      230                      235
```

( 2 ) INFORMATION FOR SEQ ID NO:7:

( i ) SEQUENCE CHARACTERISTICS:
        ( A ) LENGTH: 242 amino acids
        ( B ) TYPE: amino acid
        ( C ) STRANDEDNESS: single
        ( D ) TOPOLOGY: unknown ( i i ) MOLECULE TYPE: protein ( x i ) SEQUENCE DESCRIPTION: SEQ ID NO:7:

```
    Asn  Lys  His  Lys  Asn  Arg  Tyr  Ile  Asn  Ile  Val  Ala  Tyr  Asp  His  Ser
    1              5                        10                       15

Arg  Val  Lys  Leu  Ala  Gln  Leu  Ala  Glu  Lys  Asp  Gly  Lys  Leu  Thr  Asp
              20                       25                       30

Tyr  Ile  Asn  Ala  Asn  Tyr  Val  Asp  Gly  Tyr  Asn  Arg  Pro  Lys  Ala  Tyr
              35                       40                       45

Ile  Ala  Ala  Gln  Gly  Pro  Leu  Lys  Ser  Thr  Ala  Glu  Asp  Phe  Trp  Arg
         50                       55                       60

Met  Ile  Trp  Glu  His  Asn  Val  Glu  Val  Ile  Val  Met  Ile  Thr  Asn  Leu
    65                       70                       75                       80

Val  Glu  Lys  Gly  Arg  Arg  Lys  Cys  Asp  Gln  Tyr  Trp  Pro  Ala  Asp  Gly
                   85                       90                       95

Ser  Glu  Glu  Tyr  Gly  Asn  Phe  Leu  Val  Thr  Gln  Lys  Ser  Val  Gln  Val
                  100                      105                      110

Leu  Ala  Tyr  Tyr  Thr  Val  Arg  Asn  Phe  Thr  Leu  Arg  Asn  Thr  Lys  Ile
              115                      120                      125

Lys  Lys  Gly  Ser  Gln  Lys  Gly  Arg  Pro  Ser  Gly  Arg  Val  Val  Thr  Gln
    130                      135                      140

Tyr  His  Tyr  Thr  Gln  Trp  Pro  Asp  Met  Gly  Val  Pro  Glu  Tyr  Ser  Leu
    145                      150                      155                      160

Pro  Val  Leu  Thr  Phe  Val  Arg  Lys  Ala  Ala  Tyr  Ala  Lys  Arg  His  Ala
                   165                      170                      175

Val  Gly  Pro  Val  Val  His  Cys  Ser  Ala  Gly  Val  Gly  Arg  Thr  Gly
                   180                      185                      190

Thr  Tyr  Ile  Val  Leu  Asp  Ser  Met  Leu  Gln  Gln  Ile  Gln  His  Glu  Gly
              195                      200                      205

Thr  Val  Asn  Ile  Phe  Gly  Phe  Leu  Lys  His  Ile  Arg  Ser  Gln  Arg  Asn
    210                      215                      220

Tyr  Leu  Val  Gln  Thr  Glu  Glu  Gln  Tyr  Val  Phe  Ile  His  Asp  Thr  Leu
    225                      230                      235                      240

Val  Glu
```

( 2 ) INFORMATION FOR SEQ ID NO:8:

( i ) SEQUENCE CHARACTERISTICS:
        ( A ) LENGTH: 245 amino acids
        ( B ) TYPE: amino acid
        ( C ) STRANDEDNESS: single (D) TOPOLOGY: unknown (ii) MOLECULE TYPE: protein (xi) SEQUENCE DESCRIPTION: SEQ ID NO:8:

| Asn | Lys | His | Lys | Asn | Arg | Tyr | Ile | Asn | Ile | Leu | Ala | Tyr | Asp | His | Ser |
|---|---|---|---|---|---|---|---|---|---|---|---|---|---|---|---|
| 1 | | | | 5 | | | | | 10 | | | | | 15 | |
| Arg | Val | Lys | Leu | Arg | Pro | Leu | Pro | Gly | Lys | Asp | Ser | Lys | His | Ser | Asp |
| | | | 20 | | | | | 25 | | | | | 30 | | |
| Tyr | Ile | Asn | Ala | Asn | Tyr | Val | Asp | Gly | Tyr | Asn | Lys | Ala | Lys | Ala | Tyr |
| | | 35 | | | | | 40 | | | | | 45 | | | |
| Ile | Ala | Thr | Gln | Gly | Pro | Leu | Lys | Ser | Thr | Phe | Glu | Asp | Phe | Trp | Arg |
| | | 50 | | | | | 55 | | | | | 60 | | | |
| Met | Ile | Trp | Glu | Gln | Asn | Thr | Gly | Ile | Ile | Val | Met | Ile | Thr | Asn | Leu |
| 65 | | | | | 70 | | | | | 75 | | | | | 80 |
| Val | Glu | Lys | Gly | Arg | Arg | Lys | Cys | Asp | Gln | Tyr | Trp | Pro | Thr | Glu | Asn |
| | | | | 85 | | | | | 90 | | | | | 95 | |
| Ser | Glu | Glu | Tyr | Gly | Asn | Ile | Ile | Val | Thr | Leu | Lys | Ser | Thr | Lys | Ile |
| | | | 100 | | | | | 105 | | | | | 110 | | |
| His | Ala | Cys | Tyr | Thr | Val | Arg | Arg | Phe | Ser | Ile | Arg | Asn | Thr | Lys | Val |
| | | 115 | | | | | 120 | | | | | 125 | | | |
| Lys | Lys | Gly | Gln | Lys | Gly | Asn | Pro | Lys | Gly | Arg | Gln | Asn | Glu | Arg | Val |
| | 130 | | | | | 135 | | | | | 140 | | | | |
| Val | Ile | Gln | Tyr | His | Tyr | Thr | Gln | Trp | Pro | Asp | Met | Gly | Val | Pro | Glu |
| 145 | | | | | 150 | | | | | 155 | | | | | 160 |
| Tyr | Ala | Leu | Pro | Val | Leu | Thr | Phe | Val | Arg | Arg | Ser | Ser | Ala | Ala | Arg |
| | | | | 165 | | | | | 170 | | | | | 175 | |
| Met | Pro | Glu | Thr | Gly | Pro | Val | Leu | Val | His | Cys | Ser | Ala | Gly | Val | Gly |
| | | | 180 | | | | | 185 | | | | | 190 | | |
| Arg | Thr | Gly | Thr | Tyr | Ile | Val | Ile | Asp | Ser | Met | Leu | Gln | Gln | Ile | Lys |
| | | 195 | | | | | 200 | | | | | 205 | | | |
| Asp | Lys | Ser | Thr | Val | Asn | Val | Leu | Gly | Phe | Leu | Lys | His | Ile | Arg | Thr |
| | 210 | | | | | 215 | | | | | 220 | | | | |
| Gln | Arg | Asn | Tyr | Leu | Val | Gln | Thr | Glu | Glu | Gln | Tyr | Ile | Phe | Ile | His |
| 225 | | | | | 230 | | | | | 235 | | | | | 240 |
| Asp | Ala | Leu | Leu | Glu | | | | | | | | | | | |
| | | | | 245 | | | | | | | | | | | |

(2) INFORMATION FOR SEQ ID NO:9:

(i) SEQUENCE CHARACTERISTICS:
        (A) LENGTH: 248 amino acids
        (B) TYPE: amino acid
        (C) STRANDEDNESS: single
        (D) TOPOLOGY: unknown (ii) MOLECULE TYPE: protein (ix) FEATURE:
        (A) NAME/KEY: Modified-sites
        (B) LOCATION: 1..248
        (D) OTHER INFORMATION: /label=Xaa
        / note="For the Consensus Sequence, Xaa =Lack of Consensus"

(xi) SEQUENCE DESCRIPTION: SEQ ID NO:9:

| Asn | Lys | His | Lys | Asn | Arg | Tyr | Xaa | Asn | Ile | Leu | Xaa | Tyr | Asp | His | Ser |
|---|---|---|---|---|---|---|---|---|---|---|---|---|---|---|---|
| 1 | | | | 5 | | | | | 10 | | | | | 15 | |
| Arg | Val | Lys | Leu | Xaa | Xaa | Leu | Xaa | Xaa | Lys | Xaa | Xaa | Lys | Xaa | Ser | Asp |
| | | | 20 | | | | | 25 | | | | | 30 | | |

|  |  |  |  |  |  |  |  |  |  |  |  |  |  |  |
|---|---|---|---|---|---|---|---|---|---|---|---|---|---|---|
| Tyr | Ile | Asn 35 | Ala | Xaa | Tyr | Xaa 40 | Asp | Gly | Tyr | Asn | Glu 45 | Pro | Lys | Xaa | Tyr |
| Ile | Ala 50 | Ala | Gln | Gly | Pro | Leu 55 | Lys | Xaa | Thr | Val | Glu 60 | Asp | Phe | Trp | Arg |
| Met 65 | Ile | Trp | Glu | Gln | Asn 70 | Thr | Xaa | Val | Ile | Val 75 | Met | Xaa | Thr | Asn | Leu 80 |
| Val | Glu | Lys | Gly | Arg 85 | Arg | Lys | Cys | Xaa | Gln 90 | Tyr | Trp | Pro | Xaa | Xaa 95 | Gly |
| Ser | Glu | Xaa | Tyr 100 | Gly | Asn | Ile | Xaa | Val 105 | Thr | Val | Lys | Xaa | Val 110 | Xaa | Val |
| Leu | Ala | Xaa 115 | Xaa | Asp | Tyr | Thr | Val 120 | Arg | Lys | Phe | Xaa | Xaa 125 | Arg | Asn | Thr |
| Lys | Ile 130 | Xaa | Lys | Xaa | Gly | Xaa 135 | Lys | Xaa | Xaa | Xaa | Lys 140 | Gly | Arg | Xaa | Xaa |
| Gly 145 | Arg | Val | Val | Thr | Gln 150 | Tyr | His | Xaa | Thr | Xaa 155 | Trp | Pro | Asp | Met | Gly 160 |
| Val | Pro | Glu | Tyr | Pro 165 | Leu | Pro | Val | Leu | Xaa 170 | Phe | Val | Arg | Xaa | Val 175 | Xaa |
| Ala | Ala | Xaa | Xaa 180 | Xaa | Xaa | Xaa | Gly | Pro 185 | Xaa | Val | Val | His | Cys 190 | Ser | Ala |
| Gly | Val | Gly 195 | Arg | Thr | Gly | Thr | Tyr 200 | Ile | Val | Ile | Asp | Xaa 205 | Met | Leu | Gln |
| Gln | Ile 210 | Xaa | Xaa | Glu | Xaa | Xaa 215 | Val | Xaa | Val | Tyr | Gly 220 | Phe | Xaa | Lys | His |
| Ile 225 | Arg | Xaa | Gln | Arg | Xaa 230 | Tyr | Xaa | Val | Gln | Thr 235 | Glu | Glu | Gln | Tyr | Xaa 240 |
| Phe | Ile | His | Xaa | Ala 245 | Leu | Xaa | Glu |  |  |  |  |  |  |  |  |

( 2 ) INFORMATION FOR SEQ ID NO:10:

( i ) SEQUENCE CHARACTERISTICS:
( A ) LENGTH: 260 amino acids
( B ) TYPE: amino acid
( C ) STRANDEDNESS: single
( D ) TOPOLOGY: unknown ( i i ) MOLECULE TYPE: protein ( x i ) SEQUENCE DESCRIPTION: SEQ ID NO:10:

|  |  |  |  |  |  |  |  |  |  |  |  |  |  |  |  |
|---|---|---|---|---|---|---|---|---|---|---|---|---|---|---|---|
| Asn 1 | Lys | Ser | Lys | Asn 5 | Arg | Asn | Ser | Asn | Val 10 | Ile | Pro | Tyr | Asp | Tyr 15 | Asn |
| Arg | Val | Pro | Leu 20 | Lys | His | Glu | Leu | Glu 25 | Met | Ser | Lys | Glu | Ser 30 | Glu | His |
| Asp | Ser | Asp 35 | Glu | Ser | Ser | Asp | Asp 40 | Ser | Asp | Ser | Glu | Glu 45 | Pro | Ser |
| Lys | Tyr 50 | Ile | Asn | Ala | Ser | Phe 55 | Ile | Met | Ser | Tyr | Trp 60 | Lys | Pro | Glu | Val |
| Met 65 | Ile | Ala | Ala | Gln | Gly 70 | Pro | Leu | Lys | Glu | Thr 75 | Ile | Gly | Asp | Phe | Trp 80 |
| Gln | Met | Ile | Phe | Gln 85 | Arg | Lys | Val | Lys | Val 90 | Ile | Val | Met | Leu | Thr 95 | Glu |
| Leu | Lys | His | Gly 100 | Asp | Gln | Glu | Ile | Cys 105 | Ala | Gln | Tyr | Trp | Gly 110 | Glu | Gly |
| Lys | Gln | Thr 115 | Tyr | Gly | Asp | Ile | Glu 120 | Val | Asp | Leu | Lys | Asp 125 | Thr | Asp | Lys |
| Ser | Ser | Thr | Tyr | Thr | Leu | Arg | Val | Phe | Glu | Leu | Arg | His | Ser | Lys | Arg |

|   |     |     |     | 130 |     |     |     |     | 135 |     |     |     |     | 140 |     |
|---|-----|-----|-----|-----|-----|-----|-----|-----|-----|-----|-----|-----|-----|-----|-----|

Lys Asp Ser Arg Thr Val Tyr Gln Tyr Gln Tyr Thr Asn Trp Ser Val
145                     150                 155                 160

Glu Gln Leu Pro Ala Glu Pro Lys Glu Leu Ile Ser Met Ile Gln Val
                165             170                 175

Val Lys Gln Lys Leu Pro Gln Lys Asn Ser Ser Glu Gly Asn Lys His
            180             185             190

His Lys Ser Thr Pro Leu Leu Ile His Cys Arg Asp Gly Ser Gln Gln
        195             200             205

Thr Gly Ile Phe Cys Ala Leu Leu Asn Leu Leu Glu Ser Ala Glu Thr
    210             215             220

Glu Glu Val Val Asp Ile Phe Gln Val Val Lys Ala Leu Arg Lys Ala
225             230             235             240

Arg Pro Gly Met Val Ser Thr Phe Glu Gln Tyr Gln Phe Leu Tyr Asp
                245             250             255

Val Ile Ala Ser
            260

( 2 ) INFORMATION FOR SEQ ID NO:11:

( i ) SEQUENCE CHARACTERISTICS:
            ( A ) LENGTH: 233 amino acids
            ( B ) TYPE: amino acid
            ( C ) STRANDEDNESS: single
            ( D ) TOPOLOGY: unknown ( i i ) MOLECULE TYPE: protein ( x i ) SEQUENCE DESCRIPTION: SEQ ID NO:11:

Asn Met Lys Lys Asn Arg Val Leu Gln Ile Ile Pro Tyr Glu Phe Asn
1               5                   10                  15

Arg Val Ile Ile Pro Val Lys Arg Gly Glu Glu Asn Thr Asp Tyr Val
                20              25                  30

Asn Ala Ser Phe Ile Asp Gly Tyr Arg Gln Lys Asp Ser Tyr Ile Ala
            35              40              45

Ser Gln Gly Pro Leu Leu His Thr Ile Glu Asp Phe Trp Arg Met Ile
    50              55                  60

Trp Glu Trp Lys Ser Cys Ser Ile Val Met Leu Thr Glu Leu Glu Glu
65              70                  75                      80

Arg Gly Gln Glu Lys Cys Ala Gln Tyr Trp Pro Ser Asp Gly Leu Val
                85                  90              95

Ser Tyr Gly Asp Ile Thr Val Glu Leu Lys Lys Glu Glu Glu Cys Glu
            100             105             110

Ser Tyr Thr Val Arg Asp Leu Leu Val Thr Asn Thr Arg Glu Asn Lys
        115             120             125

Ser Arg Gln Ile Arg Gln Phe His Phe His Gly Trp Pro Glu Val Gly
    130             135             140

Ile Pro Ser Asp Gly Lys Gly Met Ile Ser Ile Ile Ala Ala Val Gln
145             150             155             160

Lys Gln Gln Gln Gln Ser Gly Asn His Pro Ile Thr Val His Cys Ser
                165             170             175

Ala Gly Ala Gly Arg Thr Gly Thr Phe Cys Ala Leu Ser Thr Val Leu
            180             185             190

Glu Arg Val Lys Ala Glu Gly Ile Leu Asp Val Phe Gln Thr Val Lys
        195             200             205

Ser Leu Ala Leu Gln Arg Pro His Met Val Gln Thr Leu Glu Gln Tyr
    210             215             220

```
        Glu  Phe  Cys  Tyr  Lys  Val  Val  Gln  Glu
        225                 230
```

( 2 ) INFORMATION FOR SEQ ID NO:12:

( i ) SEQUENCE CHARACTERISTICS:
        ( A ) LENGTH: 234 amino acids
        ( B ) TYPE: amino acid
        ( C ) STRANDEDNESS: single
        ( D ) TOPOLOGY: unknown ( i i ) MOLECULE TYPE: protein ( x i ) SEQUENCE DESCRIPTION: SEQ ID NO:12:

```
Asn  Arg  Glu  Lys  Asn  Arg  Thr  Ser  Ser  Ile  Ile  Pro  Val  Glu  Arg  Ser
1                   5                        10                       15
Arg  Val  Gly  Ile  Ser  Ser  Leu  Ser  Gly  Glu  Gly  Thr  Asp  Tyr  Ile  Asn
               20                       25                       30
Ala  Ser  Tyr  Ile  Met  Gly  Tyr  Tyr  Gln  Ser  Asn  Glu  Phe  Ile  Ile  Thr
               35                       40                       45
Gln  His  Pro  Leu  Leu  His  Thr  Ile  Lys  Asp  Phe  Trp  Arg  Met  Ile  Trp
          50                       55                       60
Asp  His  Asn  Ala  Gln  Leu  Val  Val  Met  Ile  Pro  Asp  Gly  Gln  Asn  Met
65                       70                       75                       80
Ala  Glu  Asp  Glu  Phe  Val  Tyr  Trp  Pro  Asn  Lys  Asp  Glu  Pro  Ile  Asn
                    85                       90                       95
Cys  Glu  Ser  Phe  Lys  Val  Thr  Leu  Met  Ala  Glu  Glu  His  Lys  Cys  Leu
               100                      105                      110
Ser  Asn  Glu  Glu  Lys  Leu  Ile  Ile  Gln  Asp  Phe  Ile  Leu  Glu  Ala  Thr
          115                      120                      125
Gln  Asp  Tyr  Val  Leu  Glu  Val  Arg  His  Phe  Gln  Cys  Pro  Lys  Trp
     130                      135                      140
Pro  Asn  Pro  Asp  Ser  Pro  Ile  Ser  Lys  Thr  Phe  Glu  Leu  Ile  Ser  Val
145                      150                      155                      160
Ile  Lys  Glu  Glu  Ala  Ala  Asn  Arg  Asp  Gly  Pro  Met  Ile  Val  His  Asp
                    165                      170                      175
Glu  His  Gly  Gly  Val  Thr  Ala  Gly  Thr  Phe  Cys  Ala  Leu  Thr  Thr  Leu
               180                      185                      190
Met  His  Gln  Leu  Glu  Lys  Glu  Asn  Ser  Val  Asp  Val  Tyr  Gln  Val  Ala
          195                      200                      205
Lys  Met  Ile  Asn  Leu  Met  Arg  Pro  Gly  Val  Phe  Ala  Asp  Ile  Glu  Gln
     210                      215                      220
Tyr  Gln  Phe  Leu  Tyr  Lys  Val  Ile  Leu  Ser
225                      230
```

( 2 ) INFORMATION FOR SEQ ID NO:13:

( i ) SEQUENCE CHARACTERISTICS:
        ( A ) LENGTH: 235 amino acids
        ( B ) TYPE: amino acid
        ( C ) STRANDEDNESS: single
        ( D ) TOPOLOGY: unknown ( i i ) MOLECULE TYPE: protein ( x i ) SEQUENCE DESCRIPTION: SEQ ID NO:13:

```
Asn  Lys  Glu  Lys  Asn  Arg  Asn  Ser  Ser  Val  Val  Pro  Ser  Glu  Arg  Ala
1                   5                        10                       15
Arg  Val  Gly  Leu  Ala  Pro  Leu  Pro  Gly  Met  Lys  Gly  Thr  Asp  Tyr  Ile
               20                       25                       30
```

```
Asn Ala Ser Tyr Ile Met Gly Tyr Tyr Arg Ser Asn Glu Phe Ile Ile
        35                      40                  45

Thr Gln His Pro Leu Pro His Thr Thr Lys Asp Phe Trp Arg Met Ile
        50                  55                  60

Trp Asp His Asn Ala Gln Ile Ile Val Met Leu Pro Asp Asn Gln Ser
65                      70                  75                  80

Leu Ala Glu Asp Glu Phe Val Tyr Trp Pro Ser Arg Glu Glu Ser Met
                85                  90                  95

Asn Cys Glu Ala Phe Thr Val Thr Leu Ile Ser Lys Asp Arg Leu Cys
            100                 105                 110

Leu Ser Asn Glu Glu Gln Ile Ile Ile His Asp Phe Ile Leu Glu Ala
            115                 120                 125

Thr Gln Asp Asp Tyr Val Leu Glu Val Arg His Phe Gln Cys Pro Lys
        130                 135                 140

Trp Pro Asn Pro Asp Ala Pro Ile Ser Ser Thr Phe Glu Leu Ile Asn
145                 150                 155                 160

Val Ile Lys Glu Glu Ala Leu Thr Arg Asp Gly Pro Thr Ile Val His
                165                 170                 175

Asp Glu Tyr Gly Ala Val Ser Ala Gly Met Leu Cys Ala Leu Thr Thr
            180                 185                 190

Leu Ser Gln Gln Leu Glu Asn Glu Asn Ala Val Asp Val Phe Gln Val
        195                 200                 205

Ala Lys Met Ile Asn Leu Met Arg Pro Gly Val Phe Thr Asp Ile Glu
    210                 215                 220

Gln Tyr Gln Phe Ile Tyr Lys Ala Arg Leu Ser
225                 230                 235
```

(2) INFORMATION FOR SEQ ID NO:14:

( i ) SEQUENCE CHARACTERISTICS:
        ( A ) LENGTH: 280 amino acids
        ( B ) TYPE: amino acid
        ( C ) STRANDEDNESS: single
        ( D ) TOPOLOGY: unknown ( i i ) MOLECULE TYPE: protein ( i x ) FEATURE:
        ( A ) NAME/KEY: Modified-sites
        ( B ) LOCATION: 1..280
        ( D ) OTHER INFORMATION: /label=Xaa
            / note="For the Consensus Sequence, Xaa =Lack of
            Consensus"

( x i ) SEQUENCE DESCRIPTION: SEQ ID NO:14:

```
Asn Lys Glu Lys Asn Arg Asn Ser Ser Xaa Ile Pro Tyr Glu Arg Asn
1               5                   10                  15

Arg Val Gly Xaa Xaa Xaa Leu Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Gly Glu Glu Gly Thr
            35                  40                  45

Asp Tyr Ile Asn Ala Ser Xaa Ile Met Gly Tyr Tyr Gln Ser Asn Glu
        50                  55                  60

Phe Ile Xaa Thr Gln Xaa Pro Leu Leu His Thr Ile Lys Asp Phe Trp
65                  70                  75                  80

Arg Met Ile Trp Asp His Xaa Asn Ala Gln Ile Val Met Leu Xaa Xaa
                85                  90                  95

Xaa Gln Xaa Xaa Ala Glu Xaa Glu Xaa Xaa Gln Tyr Trp Pro Ser Xaa
            100                 105                 110
```

| | | | | | | | | | | | | | | |
|---|---|---|---|---|---|---|---|---|---|---|---|---|---|---|
| Gly | Xaa | Xaa 115 | Xaa | Tyr | Gly | Asp | Xaa 120 | Xaa | Val | Xaa | Leu | Lys 125 | Xaa | Xaa | Xaa |
| Asn | Cys 130 | Glu | Ser | Xaa | Thr | Val 135 | Thr | Xaa | Xaa | Xaa | Glu 140 | Xaa | Arg | Xaa | Cys |
| Leu 145 | Ser | Asn | Glu | Xaa | Arg 150 | Xaa | Ile | Ile | Gln | Asp 155 | Phe | Ile | Leu | Glu | Ala 160 |
| Thr | Gln | Asp | Asp | Tyr 165 | Val | Leu | Glu | Val | Arg 170 | His | Phe | Gln | Cys | Pro 175 | Lys |
| Trp | Pro | Asn | Pro 180 | Asp | Xaa | Pro | Ile | Ser 185 | Xaa | Thr | Xaa | Glu | Leu 190 | Ile | Ser |
| Val | Ile | Xaa 195 | Xaa | Xaa | Xaa | Xaa | Xaa 200 | Xaa | Xaa | Gln | Lys | Xaa 205 | Glu | Glu | Ala |
| Xaa | Asn 210 | Arg | Xaa | Xaa | Xaa | Asp 215 | Gly | Pro | Xaa | Ile | Val 220 | His | Xaa | Glu | Xaa |
| Gly 225 | Ala | Val | Xaa | Xaa | Gly 230 | Thr | Phe | Cys | Ala | Leu 235 | Thr | Thr | Leu | Leu | Glu 240 |
| Gln | Leu | Glu | Xaa | Glu 245 | Asn | Xaa | Val | Asp | Val 250 | Phe | Gln | Val | Xaa | Lys 255 | Met |
| Xaa | Asn | Leu | Met 260 | Arg | Pro | Gly | Xaa | Xaa 265 | Xaa | Xaa | Ile | Glu | Gln 270 | Tyr | Gln |
| Phe | Leu | Tyr 275 | Lys | Val | Ile | Leu | Ser 280 | | | | | | | | |

RECEPTOR-TYPE PHOSPHOTYROSINE PHOSPHATASE-ALPHA

The present application is a continuation-in-part of U.S application Ser. No. 07/654,188, filed Feb. 26, 1991, now abandoned which was a continuation-in-part of U.S. application Ser. No. 07/551,270, filed Jul. 11, 1990, now abandoned. The entire contents of both of the above applications are hereby incorporated by reference.

TABLE OF CONTENTS
1. INTRODUCTION
2. BACKGROUND OF THE INVENTION
   2.1. PTKases
   2.2. PTPases
3. SUMMARY OF THE INVENTION
4. DESCRIPTION OF THE FIGURES
5. DETAILED DESCRIPTION OF THE INVENTION
6. EXAMPLE: ISOLATION AND ANALYSIS OF MURINE RPTPα cDNA CLONES
   6.1. LIBRARY SCREENING
   6.2. RESULTS
7. EXAMPLE: CHROMOSOMAL LOCALIZATION OF THE MOUSE RPTPα GENE
8. EXAMPLE: EXPRESSION OF MURINE RPTPα RNA
   8.1. Northern Analysis
   8.2. EXPRESSION OF THE MURINE RPTPα PROTEIN
   8.3. Results
9. EXAMPLE: TRANSIENT EXPRESSION OF THE MURINE RPTPα PROTEIN
   9.1. ANTIBODY PREPARATION AND IMMUNOPRECIPITATION
   9.2. Results
   9.3. GENERAL DISCUSSION FOR SECTIONS 6–9
10. EXAMPLE: ISOLATION AND CHARACTERIZATION OF HUMAN RPTP cDNA
    10.1. Materials
    10.2. Methods
    10.3. Results
    10.4. Discussion
11. EXAMPLE: EXPRESSION OF HUMAN RPTPα BY NORTHERN BLOT ANALYSIS
12. EXAMPLE: CHROMOSOME LOCALIZATION OF THE HUMAN RPTPα GENE

1. INTRODUCTION

The invention in the field of biochemistry and cell and molecular biology relates to novel receptor-type protein tyrosine phosphatase proteins or glycoproteins, termed RPTPα, RPTPβ and RPTPγ (also designated R-PTPase-α, β and γ), DNA coding therefor, methods for production and identification of the proteins, and methods for screening compounds capable of binding to and inhibiting or stimulating PTPase enzymatic activity.

2. BACKGROUND OF THE INVENTION

The identification of several growth factor receptors and retroviral oncogenes as tyrosine-specific protein kinases indicated that protein phosphorylation on tyrosine residues plays a key role in cellular growth control. This notion has recently received support by the observation that the level of tyrosine phosphorylation of enzymes thought to play an important role in signal transduction (such as phospholipase C) correlates with their increased activity upon growth factor stimulation, thus establishing a functional role for tyrosine phosphorylation (Ullrich, A., et al., *Cell* 61:203–212 (1990)).

The degree and pattern of phosphorylation of tyrosine residues on cellular proteins are regulated by the opposing activities of protein-tyrosine kinases (PTKases; ATP:protein-tyrosine O-phosphotransferase, EC 2.7.1.112) and protein-tyrosine-phosphatases (PTPases; protein-tyrosine-phosphate phosphohydrolase, EC 3.1.3.48). The structural characteristics and evolution of PTKases as well as their role in the regulation of cell growth have been reviewed (Hunter, T., et al., *Annu. Rev. Biochem.* 54:897–930 (1985); Ullrich, A., et al., supra).

2.1. PTKases

Tyrosine kinases comprise a discrete family of enzymes having common ancestry with, but major differences from, serine/threonine-specific protein kinases (Hanks, S. K. et al., (1988) *Science* 241, 42–52). The mechanisms leading to changes in activity of tyrosine kinases are best understood for receptor-type tyrosine kinases which have a transmembrane topology (Ullrich, A. et al., supra). With such kinases, the binding of specific ligands to the extracellular domain of these enzymes is thought to induce their oligomerization leading to an increase in tyrosine kinase activity and activation of the signal transduction pathways (Ullrich, A. et al., supra). The importance of this activity is supported by the knowledge that dysregulation of kinase activity through mutation or over-expression is a mechanism for oncogenic transformation (Hunter, T et al., supra; Ullrich, A. et al., 1990, supra).

2.2. PTPases

The protein phosphatases are composed of at least two separate and distinct families (Hunter, T. *Cell,* 58:1013–1016 (1989)), the protein serine/threonine phosphatases and the protein tyrosine phosphatases. This is in contrast to protein kinases, which show clear sequence similarity between serine/threonine-specific and tyrosine-specific enzymes.

There appear to be two varieties of PTPase molecules. The first group is comprised of small, soluble enzymes that contain a single conserved phosphatase catalytic domain, and include (1) placental PTPase 1B (Charbonneau, H. et al., *Proc. Natl. Acad. Sci.* 86:5252–5256 (1989); Chernoff, J. et al., *Proc. Natl. Acad. Sci. USA* 87:2735–2789 (1990)), (2) T-cell PTPase (Cool, D. E. et al., *Proc. Natl. Acad. Sci. USA* 86:5257–5261 (1989)), and (3) rat brain PTPase (Guan, K., et al., *Proc. Natl. Acad. Sci. USA,* 87:1501–1505 (1990).

The second group is made up of the more complex, receptor-linked PTPases, termed R-PTPases (or RPTPs), which are of high molecular weight and contain two tandemly repeated conserved domains separated by 56–57 amino acids. One example of RPTPs are the leukocyte common antigens (LCA) (Ralph, S. J., *EMBO J.,* 6:1251–1257 (1987); Charbonneau, H., et. al., *Proc. Natl. Acad. Sci. USA,* 85:7182–7186 (1988)). LCA, also known as CD45, T200 and Ly-5 (reviewed in Thomas, M. L., *Ann. Rev. Immunol.* 7:339–369 (1989)) comprises a group of membrane glycoproteins expressed exclusively in hemopoietic (except late erythroid) cells, derived from a common gene by alternative splicing events involving the amino terminus of the proteins. Whereas the precise function of CD45 is unknown, many studies have implicated these antigens in a number of processes, including the activity of cytotoxic T lymphocytes and natural killer cells, IL-2 receptor expression, B-cell differentiation, and T lymphocyte proliferation (Pingel, J. T. et al., *Cell* 58:1055–1065 (1989)).

Other examples of RPTPs are the LCA-related protein, LAR (Streuli, M., et al., *J. Exp. Med.,* 168:1523–1530

(1988)), and the LAR-related Drosophila proteins DLAR and DPTP (Streuli, M., et al., *Proc. Natl. Acad. Sci. USA*, 86:8698–8702 (1989)). Jirik et al. screened a cDNA library derived from the human hepatoblastoma cell line, HepG2, with a probe encoding the two PTPase domains of LCA (*FASEB J.* 4:A2082 (1990), abstr. 2253) and discovered a cDNA clone encoding a new RPTP, named He-PTP. The HePTP gene appeared to be expressed in a variety of human and murine cell lines and tissues.

While we are beginning to understand more about the structure and diversity of the PTPases, much remains to be learned about their cellular functions. It has been suggested (Tonks, N. K., et al., *Biochemistry*, 27:8695–8701 (1988)) that the small, soluble PTPase enzymes may have a "housekeeping" function. On the other hand, the RPTPs would be expected to be more restricted in their activities because of their location in the cell membrane and their potential regulation by extracellular ligands. Regarding the role of LCA (CD45) in T cells, it was found that T cell clones deficient in the expression of LCA failed to proliferate when stimulated by a specific antigen or by cross-linking of CD3 (Pingel, J. T., et al., supra). PTPase cross-linking inhibits T cell receptor CD3-mediated activation in human T cells (Kiener, P. A. et al., *J. Immunol.* 143:23–28 (1989)). The PTPase activity of LCA plays a role in the activation of pp56$^{lck}$, a lymphocyte-specific PTKase (Mustelin, T., et al., *Proc. Natl. Acad. Sci. USA*, 86:6302–6306 (1989); Ostergaard, H. L., et al., *Proc. Natl. Acad. Sci. USA*, 86:8959–8963 (1989)). These authors hypothesized that the phosphatase activity of LCA activates pp56$^{lck}$ by dephosphorylation of a C-terminal tyrosine residue, which may, in turn, be related to T-cell activation.

Using site-directed mutagenesis to determine which of four conserved cysteines in LCA (two per phosphatase domain) was required for enzyme activity toward artificial substrates, Streuli et al. (1989, supra) found that only one cysteine residue (residue 177 of LCA phosphatase domain-1) of LCA was essential for activity, indicating that, most likely, only the first phosphatase domain has enzymatic activity. However, the possibility that the second domain can dephosphorylate a different substrate was not excluded. More recently, Streuli et. al. (*EMBO J.*, 9:2399–2407 (1990)) determined that the second conserved domain of LCA (and of LAR) lacked detectable phosphatase activity but sequences within the domain could influence substrate specificity.

In order to better understand and to be able to control phosphotyrosine metabolism, one must comprehend not only the role of kinase activity, but also the action of phosphatase enzymes as well. Elevation of cellular phosphotyrosine may occur through mechanisms not involving the activation of a tyrosine kinase itself. For instance, expression of the v-crk oncogene, though not a tyrosine kinase itself, induces the phosphorylation of tyrosine residues through a poorly understood mechanism (Mayer, B. J. et al. (1988) *Nature* 332, 272–275). Potentially, such an outcome could result from either mutation of the substrate or through a general decrease in cellular phosphatase activity, especially in view of the normally high turnover rate of cellular tyrosine-phosphate (Sefton, B. M. et al. (1980) *Cell* 20, 807–816). The latter possibility is suggested by the demonstration that tyrosine phosphatase inhibitors can "reversibly transform" cells (Klarlund, J. K. *Cell* 41:707–717 (1985)). PTPases could therefore be viewed as potential recessive oncogenes.

It is becoming clear that dephosphorylation of tyrosine can by itself function as an important regulatory mechanism. Dephosphorylation of a C-terminal tyrosine residue stimulates tyrosine kinase activity in the src-family of tyrosine kinases (Hunter, T. (1987) *Cell* 49, 1–4). Tyrosine dephosphorylation has been suggested to be an obligatory step in the mitotic activation of the MPF (maturation promoting factor) kinase (Morla, A. O. al. (1989) *Cell* 58, 193–203). Lastly, mutant analysis of primitive eukaryotes has established crucial roles for serine phosphatase in cellular physiology (Cyert, M. S. et al. (1989) *Cell* 57, 891–893). These observations point out the need in the art for increasing our understanding of the mechanisms that regulate tyrosine phosphatase activity.

It is clear in the art that further analysis of structure-function relationships among these membrane receptors are needed to gain important understanding of the mechanisms of cell growth, differentiation, and oncogenesis.

3. SUMMARY OF THE INVENTION

The inventors have conceived of a role for RPTPs in cellular control mechanisms, both as potential anti-oncogenes, and as effectors in a newly discovered mechanism of transmembrane signalling. They therefore undertook a search for an RPTP potentially involved in such processes, and describe herein the identification of a novel, widely expressed member of the RPTP family, which has a transmembrane topology. Importantly, its extracellular domain is unrelated to any other RPTP heretofore described. The novel RPTPs, in a manner analogous to receptor tyrosine kinases, are subject to direct regulation by a variety of different extracellular ligands.

The present invention thus provides a human receptor-type protein tyrosine phosphatase (RPTP) protein or glycoprotein molecule other than leucocyte common antigen (LCA or CD45) and leucocyte common antigen-related protein (LAR), a functional derivative of the human RPTP or a homolog of the human RPTP in another mammalian species. When the molecule is of natural origin, it is substantially free of other proteins or glycoproteins with which it is natively associated. This naturally-occurring molecule is normally present in mammalian liver, kidney and brain. Alternatively, the RPTP molecule may not be of natural origin, such as one prepared by chemical or recombinant means.

The substantially pure RPTP protein or glycoprotein of the invention may be produced by biochemical purification of the glycoprotein of natural origin; alternatively, the RPTP may be produced by recombinant means in prokaryotic or eukaryotic hosts.

In particular, the invention is directed to the molecule RPTPα, preferably human RPTPα having the amino acid sequence (SEQ ID NO:1) shown in FIGS. 4D and 8, or a functional derivative thereof. In another embodiment, the invention is directed to human RPTPβ. In yet another embodiment, the invention is directed to human RPTPγ.

The invention is further directed to a nucleic acid molecule consisting essentially of a nucleotide sequence encoding RPTPα of mouse or human origin, or RPTPβ or RPTPγ, both of human origin, or a functional derivative thereof. The nucleic acid molecule may be in the form of cDNA or genomic DNA. Preferably, the nucleic acid molecule has the nucleotide sequence of human RPTPα-encoding DNA, SEQ ID NO:2, also shown in FIGS. 8A–8C. The invention is further directed to the nucleic acid molecule in the form of an expression vehicle, as well as prokaryotic and eukaryotic hosts transformed with the nucleic acid molecule.

Also included in the present invention is a process for preparing an RPTP protein or glycoprotein of this invention, or a functional derivative thereof, comprising:

(a) culturing a host capable of expressing the protein, glycoprotein or functioanl derivative under culturing conditions;

(b) expressing the protein, glycprotein or functional derivative; and (c) recovering the protein, glycoprotein or functional derivative from the culture.

The invention is directed to an antibody, polyclonal, monoclonal, or chimeric, specific for the RPTPα protein or glycoprotein.

The invention is also directed to a method for detecting the presence of nucleic acid encoding a normal or mutant RPTP in a subject comprising:

(a) contacting a cell or an extract thereof from the subject with an oligonucleotide probe encoding at least a portion of the normal or mutant RPTP under hybridizing conditions; and (b) measuring the hybridization of the probe to the nucleic acid of the cell, thereby detecting the presence of the nucleic acid.

The DNA can be selectively amplified, using the polymerase chain reaction, prior to assay.

The invention is further directed to a method for detecting the presence, or measuring the quantity of an RPTP in cell or in a subject comprising:

(a) contacting said cell or an extract thereof with an antibody specific for an epitope of the RPTP; and (b) detecting the binding of the antibody to the cell or extract thereof, or measuring the quantity of antibody bound, thereby detecting the presence or measuring the quantity of the RPTP.

The present invention is also directed to methods for identifying and isolating a compound capable of binding to an RPTP from a chemical or biological preparation comprising:

(a) attaching the RPTP or the ligand-binding portion thereof to a solid phase matrix;

(b) contacting the chemical or biological preparation with the solid phase matrix allowing the compound to bind, and washing away any unbound material;

(c) detecting the presence of the compound bound to the solid phase; and, for purposes of isolation, (d) eluting the bound compound, thereby isolating the compound.

Finally, the invention includes a method for identifying a compound capable of stimulating or inhibiting the enzymatic activity of a RPTP, comprising:

(a) contacting the compound with the RPTP in pure form, in a membrane preparation, or in a whole live or fixed cell;

(b) incubating the mixture in step (a) for a sufficient interval;

(c) measuring the enzymatic activity of the RPTP;

(d) comparing the enzymatic activity to that of the RPTP incubated without the compound, thereby determining whether the compound stimulates or inhibits the activity.

In all the above methods, the RPTP is preferably RPTPα, most preferably, human RPTPα.

4. DESCRIPTION OF THE FIGURES

FIGS. 1A–1D show the nucleotide sequence (SEQ ID NO:4) and predicted amino acid sequence (SEQ ID NO:3) of murine RPTPα. FIGS. 1A–1D show the sequence of the phage λ-109 cDNA insert (numbering refers to nucleotide positions) and predicted RPTPα protein sequence (using the standard one-letter amino acid code). The putative transmembrane domain (amino acids 143 to 166) is underlined as well as the potential N-linked glycosylation sites in the extracellular domain. The borders of homology between the tandemly repeated PTPase domains (I and II) are indicated by square brackets. Cysteine (C) residues conserved in the catalytic domain of all known RPTPs are also underlined. FIG. 1E shows a schematic structure of a λ-109 cDNA clone containing the RPTPα coding sequence. RPTP domains I and II are indicated as black boxes, the transmembrane domain is shaded. The start of the N-terminally truncated PTP-ΔC protein (see FIG. 3, below) is indicated by an arrow (at amino acid 214). The positions of restriction sites used for generating nested deletions for sequencing are indicated. Abbreviations: TM, transmembrane domain; B, BamHI site; Bs, BstEII site; N, NcoI site; Nd, NdeI site; P, PstI site; R, EcoRI site; S: SacII site; St, StuI site.

FIG. 2 is a Northern blot showing expression of the murine RPTPα mRNA. 5 μg of Poly A$^+$ RNA from mouse tissues and cell lines was fractionated on formaldehyde-containing agarose gels and subjected to Northern analysis using as a probe the entire RPTPα cDNA. The positions of the 28S and 18S ribosomal RNA are indicated. Lanes: 1, kidney; 2, lung; 3, heart; 4, stomach; 5, brain; 6, spleen; 7, liver; 8, NIH-3T3 fibroblast cell line (Honegger, A. M. et al. (1987) Cell 51, 199–209); 9, BAF prepro-B lymphoid cell line (Palacios, R. et al. (1985) Cell 41, 727–734).

Figure 3:
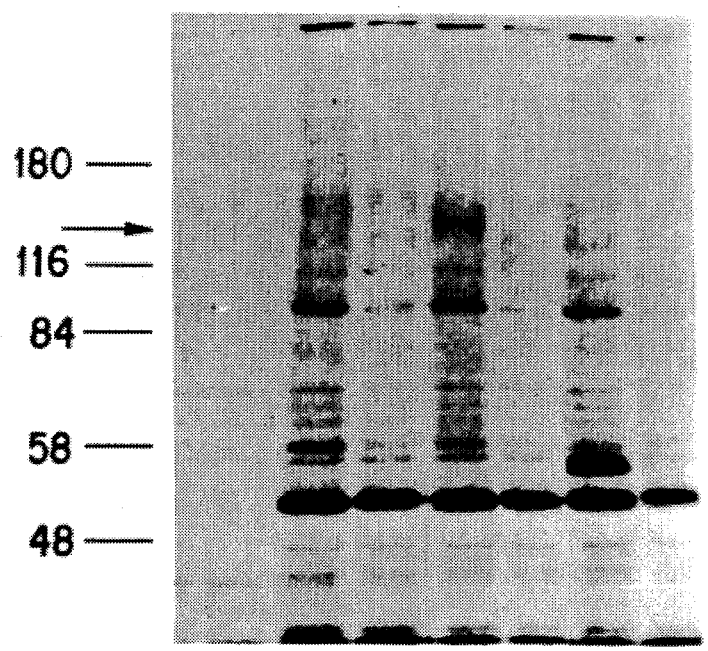

FIG. 3 is a gel pattern showing results of PAGE of immunoprecipitates of the murine RPTPα protein. COS cells were transiently transfected using the DEAE-dextran method with a negative control plasmid (expression vector pLSV without insert), with either pLSV-PTP-α (the same expression vector containing the RPTPα cDNA), or with the expression vector pLSVΔC, designed to express a truncated RPTPα protein (PTP-ΔC, amino-acids 214–794, from which the transmembrane and extracellular domains have been removed). After metabolic labelling with [$^{35}$S]-methionine, immunoprecipitation was performed using either pre-immune serum (lanes 1 and 2) or with an antiserum designated "2A" (lanes 3–8), raised against a synthetic peptide corresponding to the C-terminus of the RPTPα protein in the absence or presence of 100 μg of the immunizing peptide. Sizes of molecular weight markers are shown in kDa at the left margin. The arrow marks the position of the 130 kDa RPTPα protein (lane 5). Lane 1: pLSV, pre-immune serum; lane 2: pLSV-PTP-α, pre-immune serum; lane 3: pLSV, antiserum 2A; lane 4: pLSV, antiserum 2A in the presence of synthetic peptide; lane 5: pLSV-PTP-α, antiserum 2A; lane 6: pLSV-PTP-α, antiserum 2A in the presence of synthetic peptide; lane 7: pLSVΔC, antiserum 2A; lane 8: pLSVΔC, antiserum 2A in the presence of synthetic peptide.

FIGS. 4A, 4B, 4C and 4D show the structure of human RPTPα deduced from the sequence of cDNA clones. FIG. 4A is a composite restriction map [3615 base pairs (bp)] of overlapping clones 31-4 and 27-1, which together contain the entire coding region of human RPTPα. FIG. 4B shows the relative positions of clones 31-4 and 27-1. Both strands of each clone were sequenced in their entirety by using a series of oligonucleotide primers. The hatched region in clone 31-4 corresponds to the fragment used as probe for the Northern blot (see FIG. 6, below) as well as for the chromosome assignment. FIG. 4C shows the different domains of RPTPα. FIG. 4D provides a comparison of the amino acid sequences of human (line 1) [SEQ ID NO:1] and mouse (line 2) [SEQ ID NO:3] RPTPα. The single-letter amino acid code is used. Only the differences are shown. The dashed line indicates a stretch of amino acids not present in the mouse sequence. The coding portion of human RPTPα, and its position relative to clones 31-4 and 27-1 (FIG. 4B), is shown at the top. The following regions are designated in encircled Roman numerals: signal peptide (I), extracellular domain with potential N-glycosylation sites for the human protein underlined (II), transmembrane (III), juxtamembrane (IV), first phosphatase domain (V), interdomain (VI), second phosphatase domain (VII), C terminus (VIII).

FIGS. 5A–5D; SEQ ID NO's 5–9 show a comparison of the amino acid sequences of the first (FIGS. 5A and 5B) and second (FIGS. 5C and 5D SEQ ID NO's: 10–14) conserved phosphatase domains of human RPTPs LCA, a, β and γ. CON is the consensus sequence: a capital letter indicates complete agreement, while a small letter indicates agreement among two or three of the four sequences. A dash indicates lack of consensus.

Figure 6:
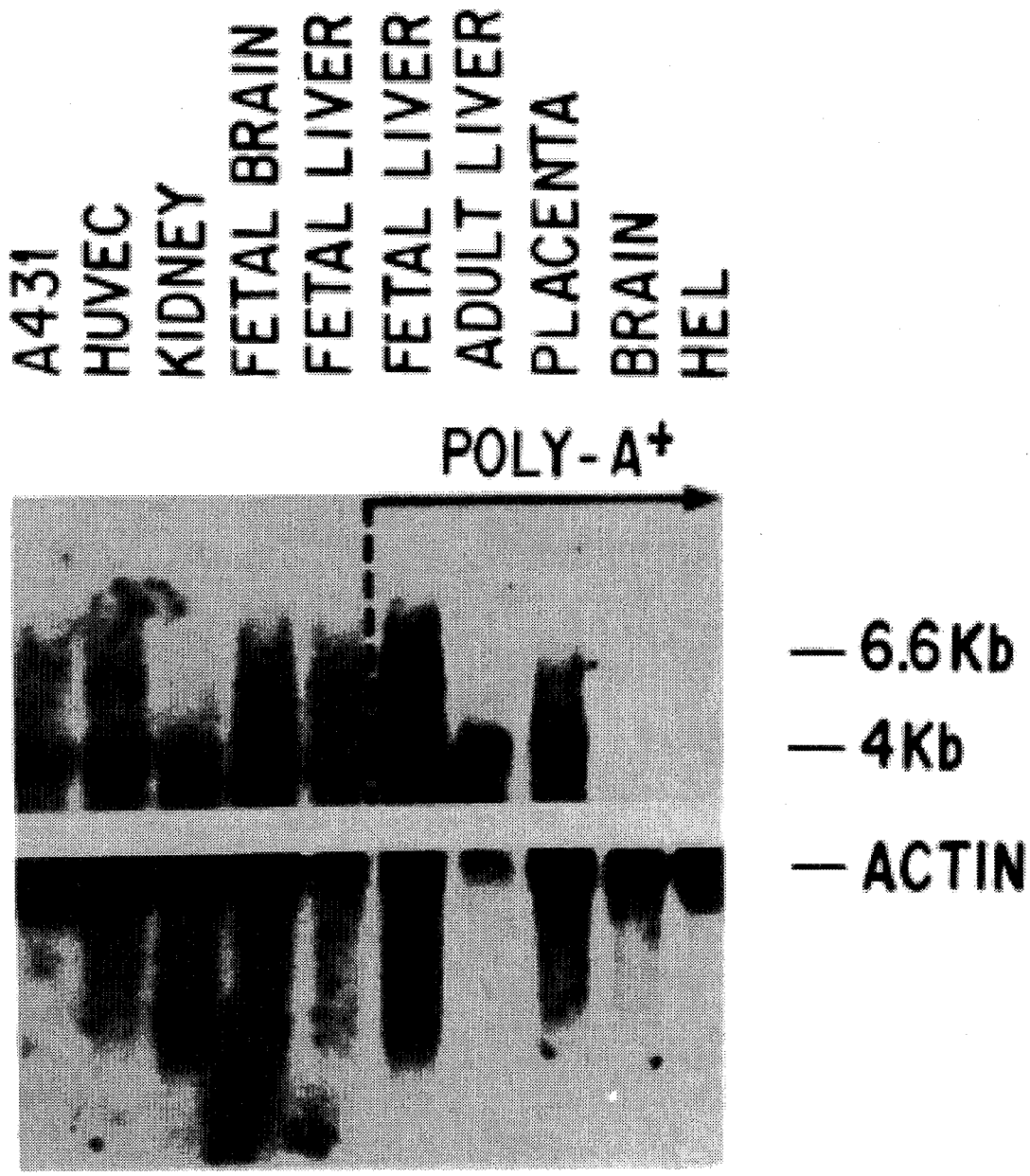

FIG. 6 shows a Northern blot pattern indicating relative expression of human RPTPα in various tissues and cell lines, as determined by hybridization with RPTPα probe (Upper) and β-actin probe (Lower). Total RNA (five left lanes) or poly (A)$^+$ RNA (five right lanes) samples from the indicated human cell lines or tissues were analyzed. A431 is a human epidermoid carcinoma cell line; HEL is an erythroleukemia cell line; all other lanes represent flash-frozen tissues samples (HUVEC—human umbilical vein endothelial cells).

Figure 7:
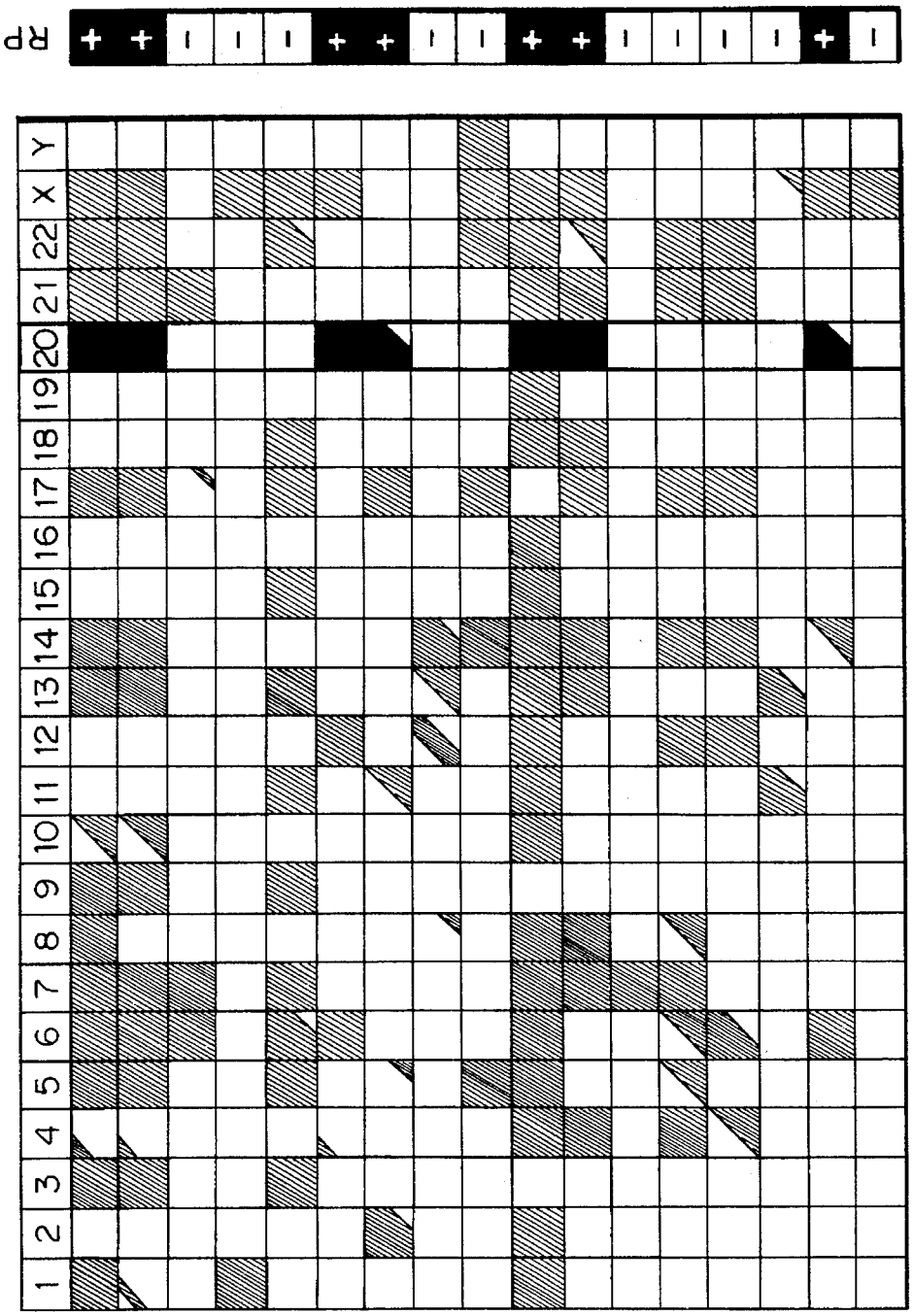

FIG. 7 is a matrix diagram which shows the chromosomal localization of human RPTPα based on analysis of a panel of 17 rodent-human somatic cell hybrids. A completely stippled box indicates that the hybrid contained the human chromosome indicated in the upper row; lower-right stippling indicates presence of the long arm of (or part of the long arm, indicated by a smaller fraction of stippling) of the chromosome; upper-left stippling indicates presence of the short arm (or partial short arm) of the chromosome; an open box indicates absence of the chromosome. The boxes in the column for chromosome 20 are blackened to highlight correlation of presence of this chromosome (or chromosome region) with the presence of the RPTPα gene. The pattern of retention of the human RPTPα sequences in the hybrids is shown at right (RPTPα): presence of the gene is indicated by a "+" in a black box; absence of the gene is indicated by a "–" in an open box.

FIGS. 8A–8C show the complete nucleotide sequence (SEQ ID NO:2) and deduced amino acid sequence (SEQ ID NO:1) of human RPTPα.

5. DETAILED DESCRIPTION OF THE INVENTION

Through the use of recombinant DNA methods, the present inventors have identified novel mammalian receptor-type (transmembrane) protein tyrosine phosphatases (PTPase; EC 3.1.3.48). The murine RPTPα has 794 amino acids, whereas the human RPTPα has 802 amino acids. In view of its receptor-like structure, and the likelihood that it is part of a family, the inventors have termed this protein, RPTPα (receptor protein tyrosine phosphatase alpha). The family is designated herein as "RPTP."

RPTPα has an intracellular domain homologous to the catalytic domains of other tyrosine phosphatases. The inventors have further characterized the 142 amino acid extracellular domain (including signal peptide) as having a high serine and threonine content (32%) and 8 potential N-glycosylation sites. The inventors have produced cDNA clones coding for the novel protein, and expressed the protein from eukaryotic hosts. Northern analysis has been used to identify the natural expression of the protein in various cells and tissues. They have further produced a polyclonal antibody to the protein by immunization with a synthetic peptide of RPTPα, which identifies a 130 kDa protein in cells transfected with a cDNA clone encoding a portion of RPTPα.

Remarkably, in addition to being composed of intracellular domains having enzymatic activity, the receptor family to which RPTPs belong includes transmembrane proteins having and N-terminal extracellular domains; this is analogous to the tyrosine kinase enzyme family (Tonks, N. K. et al. (1988) *Biochemistry* 27, 8695–8701; Charbonneau, H. et al. (1988) *Proc. Natl. Acad. Sci. USA* 85, 7182–7186; Streuli, M. et al., (1988) *J. Exp. Med.* 168, 1523–2530; Streuli, M. et al., (1989) *Proc. Natl. Acad. Sci. USA* 86, 8698–8702). The present inventors have therefore concluded that ligands in the extracellular environment can control the activity of this membrane-associated subclass of PTPases.

RPTPα and the other RPTPs of the present invention are useful in methods for screening drugs and other agents which are capable of activating or inhibiting the RPTP activity, and thereby affecting major pathways of cellular metabolism. By attaching an intact RPTP, or the ligand-binding portion thereof, to a solid phase matrix, an affinity probe is created which can be used to screen biological products or chemical agents for their capacity to interact with the receptor on the basis of their binding activity. Bound material can then be eluted from the affinity probe in purified form.

Methods for coupling proteins and peptides to the solid phase, the solid phase substances useful in these methods, and means for elution, are well known to those of skill in the art.

The RPTP protein or derivatives thereof having enzymatic activity can be used for testing of compounds capable of enhancing or inhibiting the phosphatase activity. The ability of a compound under test to modify phosphatase activity can be tested in an in vitro system wherein the test compound is added to purified RPTP protein or enzymatically active derivatives thereof, and the affects on enzyme activity measured using standard enzymological procedures well known to those of skill in the art.

Alternatively, the action of a compound on RPTP activity can be measured in a whole cell preparation using live or fixed cells, or a membrane fraction derived from live or fixed cells. This method is useful for screening compounds acting via the extracellular receptor portion of the protein, as well as compounds acting directly on the enzymatic portion of the protein. A test compound is incubated with cells, or with a membrane preparation derived therefrom, which express high amounts of the RPTP of this invention, such as transfected COS or NIH-3T3 cells. The amount of cellular phosphotyrosine is then measured, using methods well-known in the art (Honegger, A. M. et al., *Cell* 51:199–209 (1987); Margolis, B. et al., *Cell* 57:1101–1107 (1989)). The results are compared to results obtained in the absence of the test compound, or in the absence or presence of a known activator of RPTP enzymatic activity. In such studies, the action of the test compound in the presence of an activator of tyrosine kinase can also be measured.

A compound which stimulates RPTP activity will result in a net decrease in the amount of phosphotyrosine, whereas a compound which inhibits RPTP activity will result in a net increase in the amount of phosphotyrosine.

In the case of growth factor receptors which are tyrosine kinases, such as the receptors for epidermal growth factor (EGF) and for platelet-derived growth factor (PDGF), tyrosine phosphorylation is linked to cell growth and to oncogenic transformation. Activation of a PTPase, leading to dephosphorylation, would serve as a counterregulatory mechanism to prevent or inhibit growth, and might serve as an endogenous regulatory mechanism against cancer. Thus, mutation or dysregulation of this receptor/enzyme system may promote susceptibility to cancer.

The insulin receptor is also a tyrosine kinase, and phosphorylation of tyrosine in cells bearing insulin receptors would be associated with normal physiological function. In contrast to the case of cell growth and cancer, activation of an RPTP would counteract insulin effects. Subnormal RPTP levels or enzymatic activity would act to remove a normal counterregulatory mechanisms. Perhaps more important, though, over-activity, or inappropriate activation, of a RPTP would be expected to inhibit or totally prevent the action of insulin on cells, leading to diabetes (of an insulin-resistant variety). Thus, susceptibility to diabetes may be associated with RPTP dysregulation.

Therefore, the methods of the present invention for identifying normal or mutant RPTP genes, or for measuring the amount or activity of RPTP associated with a cell or tissue, can serve as methods for identifying susceptibility to cancer, diabetes, or other diseases associated with alterations in cellular phosphotyrosine metabolism.

The present invention provides methods for evaluating the presence and the level of normal or mutant RPTP in a subject. Absence, or more typically, low expression of the RPTP, or presence of a mutant RPTP, in an individual may serve as an important predictor of susceptibility to oncogenic transformation and the development of cancer. Alternatively, over-expression of RPTP, possibly due to a mutant receptor/enzyme system insensitive to negative regulation, or due to overabundance of a stimulatory ligand in the body, may serve as an important predictor of susceptibility to diabetes.

Oligonucleotide probes encoding various portions of the RPTP (see below) are used to test cells from a subject for the presence DNA or RNA sequences encoding the RPTP. A preferred probe would be one directed to the nucleic acid sequence encoding at least 4 amino acid residues, and preferably at least 5 amino acid residues, of the RPTPα or other RPTP protein of the present invention. Qualitative or quantitative assays can be performed using such probes. For example, Northern analysis (see Examples III and VI, below) is used to measure expression of an RPTP mRNA in a cell or tissue preparation.

Such methods can be used even with very small amounts of DNA obtained from an individual, following use of selective amplification techniques. Recombinant DNA methodologies capable of amplifying purified nucleic acid fragments have long been recognized. Typically, such methodologies involve the introduction of the nucleic acid fragment into a DNA or RNA vector, the clonal amplification of the vector, and the recovery of the amplified nucleic acid fragment. Examples of such methodologies are provided by Cohen et al. (U.S. Pat. No. 4,237,224), Sambrook et al. *Molecular Cloning: A Laboratory Manual,* Second Edition, Cold Spring Harbor Press, Cold Spring Harbor, N.Y. (1989), which references are herein incorporated by reference).

Recently, an in vitro, enzymatic method has been described which is capable of increasing the concentration of such desired nucleic acid molecules. This method has been referred to as the "polymerase chain reaction or "PCR" (Mullis, K. et al., *Cold Spring Harbor Symp. Quant. Biol.* 51:263–273 (1986); Erlich, H. et al., EP 50,424; EP 84,796, EP 258,017, EP 237,362; Mullis, K., EP 201,184; Mullis, K. et al., U.S. Pat. No. 4,683,202; Erlich, H., U.S. Pat. No. 4,582,788; and Saiki, R. et al., U.S. Pat. No. 4,683,194).

The polymerase chain reaction provides a method for selectively increasing the concentration of a particular nucleic acid sequence even when that sequence has not been previously purified and is present only in a single copy in a particular sample. The method can be used to amplify either single- or double-stranded DNA. The essence of the method involves the use of two oligonucleotide probes to serve as primers for the template-dependent, polymerase mediated replication of a desired nucleic acid molecule.

The precise nature of the two oligonucleotide probes of the PCR method is critical to the success of the method. As is well known, a molecule of DNA or RNA possesses directionality, which is conferred through the 5'-3' linkage of the phosphate groups of the molecule. Sequences of DNA or RNA are linked together through the formation of a phosphodiester bond between the terminal 5' phosphate group of one sequence and the terminal 3' hydroxyl group of a second sequence. Polymerase dependent amplification of a nucleic acid molecule proceeds by the addition of a 5' nucleotide triphosphate to the 3' hydroxyl end of a nucleic acid molecule. Thus, the action of a polymerase extends the 3' end of a nucleic acid molecule. These inherent properties are exploited in the selection of the oligonucleotide probes of the PCR. The oligonucleotide sequences of the probes of the PCR method are selected such that they contain sequences identical to, or complementary to, sequences which flank the particular nucleic acid sequence whose amplification is desired.

More specifically, the oligonucleotide sequences of the "first" probe is selected such that it is capable of hybridizing to an oligonucleotide sequence located 3' to the desired sequence, whereas the oligonucleotide sequence of the "second" probe is selected such that it contains an oligonucleotide sequence identical to one present 5' to the desired region. Both probes possess 3' hydroxy groups, and therefore can serve as primers for nucleic acid synthesis.

In the PCR, the reaction conditions are cycled between those conducive to hybridization and nucleic acid polymerization, and those which result in the denaturation of duplex molecules. In the first step of the reaction, the nucleic acids of the sample are transiently heated, and then cooled, in order to denature any double-stranded molecules which may be present. The "first" and "second" probes are then added to the sample at a concentration which greatly exceeds that of the desired nucleic acid molecule. When the sample is incubated under conditions conducive to hybridization and polymerization, the "first" probe will hybridize to the nucleic acid molecule of the sample at a position 3' to the sequence to be amplified. If the nucleic acid molecule of the sample was initially double-stranded, the "second" probe will hybridize to the complementary strand of the nucleic acid molecule at a position 3' to the sequence which is the complement of the sequence whose amplification is desired. Upon addition of a polymerase, the 3' ends of the "first" and (if the nucleic acid molecule was double-stranded) "second" probes will be extended. The extension of the "first" probe will result in the synthesis of an oligonucleotide having the exact sequence of the desired nucleic acid. Extension of the "second" probe will result in the synthesis of an oligonucleotide having the exact sequence of the complement of the desired nucleic acid.

The PCR reaction is capable of exponential amplification of specific nucleic acid sequences because the extension product of the "first" probe, of necessity, contains a sequence which is complementary to a sequence of the "second" probe, and thus can serve as a template for the production of an extension product of the "second" probe. Similarly, the extension product of the "second" probe, of necessity, contains a sequence which is complementary to a sequence of the "first" probe, and thus can serve as a template for the production of an extension product of the "first" probe. Thus, by permitting cycles of polymerization, and denaturation, a geometric increase in the concentration of the desired nucleic acid molecule can be achieved. Reviews of the PCR are provided by Mullis, K. B. (*Cold Spring Harbor Symp. Quant. Biol.* 51:263–273 (1986)); Saiki, R. K., et al. (*Bio/Technology* 3:1008–1012 (1985)); and Mullis, K. B., et al. (*Meth. Enzymol.* 155:335–350 (1987)).

In one embodiment, the invention is directed to a naturally occurring mammalian RPTPα. In another embodiment, the invention is directed to a recombinant mammalian RPTPα. The preferred RPTPs of the present invention are of human origin. The invention provides the naturally occurring molecule substantially free of other proteins with which it is natively associated. "Substantially free of other proteins or glycoproteins" indicates that the protein has been purified away from at least 90 per cent (on a weight basis), and from even at least 99 per cent if desired, of other proteins and glycoproteins with which it is natively associated, and is therefore substantially free of them. That can be achieved by subjecting the cells, tissue or fluids containing the RPTP to standard protein purification techniques such as immunoadsorbent columns bearing monoclonal antibodies reactive against the protein. Other forms of affinity purification can utilize solid-phase substrates which can bind the PTPase domain, or a ligand that will bind to the receptor domain. Alternatively, the purification can be achieved by a combination of standard methods, such as ammonium sulfate precipitation, molecular sieve chromatography, and ion exchange chromatography.

It will be understood that the mammalian RPTP of the present invention can be biochemically purified from a variety of cell or tissue sources. For preparation of naturally occurring RPTP, tissues such as mammalian placenta or brain, especially of human origin, are preferred.

Alternatively, because the gene for the RPTP can be isolated or synthesized, the polypeptide can be synthesized substantially free of other proteins or glycoproteins of mammalian origin in a prokaryotic organism or in a non-mammalian eukaryotic organism, if desired. As intended by the present invention, a recombinant RPTPα molecule produced in mammalian cells, such as transfected COS, NIH-3T3, or CHO cells, for example, is either a naturally occurring protein sequence or a functional derivative thereof. Where a naturally occurring protein or glycoprotein is produced by recombinant means, it is provided substantially free of the other proteins and glycoproteins with which it is natively associated.

Alternatively, methods are well known for the synthesis of polypeptides of desired sequence on solid phase supports and their subsequent separation from the support.

In a further embodiment, the invention provides "functional derivatives" of the RPTP. By "functional derivative" is meant a "fragment," "variant," "analog," or "chemical derivative" of the RPTP, which terms are defined below. A function al derivative retains at least a portion of the function of the RPTP, such as binding to a specific antibody, phosphatase enzymatic activity or binding of the extracellular domain to a ligand, which permits its utility in accordance with the present invention.

A "fragment" of the RPTP refers to any subset of the molecule, that is, a shorter peptide.

A "variant" of the RPTP refers to a molecule substantially similar to either the entire peptide or a fragment thereof. Variant peptides may be conveniently prepared by direct chemical synthesis of the variant peptide, using methods well-known in the art.

Alternatively, amino acid sequence variants of the peptide can be prepared by mutations in the DNA which encodes the synthesized peptide. Such variants include, for example, deletions from, or insertions or substitutions of, residues within the amino acid sequence. Any combination of deletion, insertion, and substitution may also be made to arrive at the final construct, provided that the final construct possesses the desired activity. Obviously, the mutations that will be made in the DNA encoding the variant peptide must not alter the reading frame and preferably will not create complementary regions that could produce secondary mRNA structure (see European Patent Publication No. EP 75,444).

At the genetic level, these variants ordinarily are prepared by site-directed mutagenesis (as exemplified by Adelman et al., *DNA* 2:183 (1983)) of nucleotides in the DNA encoding the peptide molecule, thereby producing DNA encoding the variant, and thereafter expressing the DNA in recombinant cell culture (see below). The variants typically exhibit the same qualitative biological activity as the nonvariant peptide.

An "analog" of the RPTP refers to a non-natural molecule substantially similar to either the entire molecule or a fragment thereof.

A "chemical derivative" of the RPTP contains additional chemical moieties not normally a part of the peptide. Covalent modifications of the peptide are included within the scope of this invention. Such modifications may be introduced into the molecule by reacting targeted amino acid residues of the peptide with an organic derivatizing agent that is capable of reacting with selected side chains or terminal residues.

Cysteinyl residues most commonly are reacted with alpha-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, alpha-bromo-beta-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri- 4-nitrophenol, or chloro-7-nitrobenzo-2-oxa-1,3-diazole.

Histidyl residues are derivatized by reaction with diethylprocarbonate at pH 5.5–7.0 because this agent is relatively specific for the histidyl side chain. Para-bromophenacyl bromide also is useful; the reaction is preferably performed in 0.1M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing alpha-amino-containing residues include imidoesters such as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine epsilon-amino group.

The specific modification of tyrosyl residues per se has been studied extensively, with particular interest in introducing spectral labels into tyrosyl residues by reaction with aromatic diazonium compounds or tetranitromethane. Most commonly, N-acetylimidizol and tetranitromethane are used to form O-acetyl tyrosyl species and 3-nitro derivatives, respectively.

Carboxyl side groups (aspartyl or glutamyl) are selectively modified by reaction with carbodiimides (R'-N-C-N-R') such as 1-cyclohexyl-3-(2-morpholinyl( 4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Glutaminyl and asparaginyl residues are frequently deamidated to the corresponding glutamyl and aspartyl residues. Alternatively, these residues are deamidated under mildly acidic conditions. Either form of these residues falls within the scope of this invention.

Derivatization with bifunctional agents is useful for cross-linking the peptide to a water-insoluble support matrix or to other macromolecular carriers. Commonly used cross-linking agents include, e.g., 1,1-bis(diazoacetyl)- 2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidyl-propionate), and bifunctional maleimides such as bis-N-maleimido-1,8-octane. Derivatizing agents such as methyl-3-[(p-azidophenyl)dithio]epropioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Other modifications include hydroxylation of proline and lysine, phosphorylation of hydroxyl groups of seryl or threonyl residues, methylation of the alpha-amino groups of lysine, arginine, and histidine side chains (T. E. Creighton, *Proteins: Structure and Molecule Properties,* W. H. Freeman & Co., San Francisco, pp. 79–86 (1983)), acetylation of the N-terminal amine, and, in some instances, amidation of the C-terminal carboxyl groups.

Such derivatized moieties may improve the solubility, absorption, biological half life, and the like. The moieties may alternatively eliminate or attenuate any undesirable side effect of the protein and the like. Moieties capable of mediating such effects are disclosed, for example, in *Remington's Pharmaceutical Sciences,* 16th ed., Mack Publishing Co., Easton, Pa. (1980)

This invention is also directed to an antibody specific for an epitope of RPTP, preferably, of RPTPα, most preferably of human RPTPα, and the use of such antibody to detect the presence of, or measure the quantity or concentration of, the RPTP in a cell, a cell or tissue extract, or a biological fluid.

The term "antibody" is meant to include polyclonal antibodies, monoclonal antibodies (mAbs), chimeric antibodies, and anti-idiotypic (anti-Id) antibodies.

Polyclonal antibodies are heterogeneous populations of antibody molecules derived from the sera of animals immunized with an antigen.

Monoclonal antibodies are a substantially homogeneous population of antibodies to specific antigens. MAbs may be obtained by methods known to those skilled in the art. See, for example Kohler and Milstein, *Nature* 256:495–497 (1975) and U.S. Pat. No. 4,376,110. Such antibodies may be of any immunoglobulin class including IgG, IgM, IgE, IgA, GILD and any subclass thereof. The hybridoma producing the mAbs of this invention may be cultivated in vitro or in vivo. Production of high titers of mAbs in vivo production makes this the presently preferred method of production. Briefly, cells from the individual hybridomas are injected intraperitoneally into pristane-primed BALB/c mice to produce ascites fluid containing high concentrations of the desired mAbs. MAbs of isotype IgM or IgG may be purified from such ascites fluids, or from culture supernatants, using column chromatography methods well known to those of skill in the art.

Chimeric antibodies are molecules different portions of which are derived from different animal species, such as those having variable region derived from a murine mAb and a human immunoglobulin constant region. Chimeric antibodies and methods for their production are known in the art (Cabilly et al, *Proc. Natl. Acad. Sci. USA* 81:3273–3277 (1984); Morrison et al., *Proc. Natl. Acad. Sci. USA* 81:6851–6855 (1984); Boulianne et al., *Nature* 312:643–646 (1984); Cabilly et al., European Patent Application 125023 (published Nov. 14, 1984); Neuberger et al., *Nature* 314:268–270 (1985); Taniguchi et al., European Patent Application 171496 (published Feb. 19, 1985); Morrison et al., European Patent Application 173494 (published Mar. 5, 1986); Neuberger et al., PCT Application WO 86/01533 (published Mar. 13, 1986); Kudo et al., European Patent Application 184187 (published June 11, 1986); Morrison et al., European Patent Application 173494 (published Mar. 5, 1986); Sahagan et al., *J. Immunol.* 137:1066–1074 (1986); Robinson et al., International Patent Publication #PCT/US86/02269 (published 7 May 1987); Liu et al., *Proc. Natl. Acad. Sci. USA* 84:3439–3443 (1987); Sun et al., *Proc. Natl. Acad. Sci. USA* 84:214–218 (1987); Better et al., *Science* 240:1041–1043 (1988)). These references are hereby incorporated by reference.

An anti-idiotypic (anti-Id) antibody is an antibody which recognizes unique determinants generally associated with the antigen-binding site of an antibody. An anti-Id antibody can be prepared by immunizing an animal of the same species and genetic type (e.g. mouse strain) as the source of the mAb with the mAb to which an anti-Id is being prepared. The immunized animal will recognize and respond to the idiotypic determinants of the immunizing antibody by producing an antibody to these idiotypic determinants (the anti-Id antibody).

The anti-Id antibody may also be used as an "immunogen" to induce an immune response in yet another animal, producing a so-called anti-anti-Id antibody. The anti-anti-Id may be epitopically identical to the original mAb which induced the anti-Id. Thus, by using antibodies to the idiotypic determinants of a mAb, it is possible to identify other clones expressing antibodies of identical specificity.

Accordingly, mAbs generated against the RPTP of the present invention may be used to induce anti-Id antibodies in suitable animals, such as BALB/c mice. Spleen cells from such immunized mice are used to produce anti-Id hybridomas secreting anti-Id mAbs. Further, the anti-Id mAbs can be coupled to a carrier such as keyhole limpet hemocyanin (KLH) and used to immunize additional BALB/c mice. Sera from these mice will contain anti-anti-Id antibodies that have the binding properties of the original mAb specific for a RPTP epitope.

The anti-Id mAbs thus have their own idiotypic epitopes, or "idiotopes" structurally similar to the epitope being evaluated, such as RPTPα.

The term "antibody" is also meant to include both intact molecules as well as fragments thereof, such as, for example, Fab and F(ab')$_2$, which are capable of binding antigen. Fab and F(ab')$_2$ fragments lack the Fc fragment of intact antibody, clear more rapidly from the circulation, and may have less non-specific tissue binding than an intact antibody (Wahl et al., *J. Nucl. Med.* 24:316–325 (1983)).

It will be appreciated that Fab and F(ab')$_2$ and other fragments of the antibodies useful in the present invention may be used for the detection and quantitation of RPTP according to the methods disclosed herein for intact antibody molecules. Such fragments are typically produced by proteolytic cleavage, using enzymes such as papain (to produce Fab fragments) or pepsin (to produce F(ab')$_2$ fragments).

An antibody is said to be "capable of binding" a molecule if it is capable of specifically reacting with the molecule to thereby bind the molecule to the antibody. The term "epitope" is meant to refer to that portion of any molecule capable of being bound by an antibody which can also be recognized by that antibody. Epitopes or "antigenic determinants" usually consist of chemically active surface groupings of molecules such as amino acids or sugar side chains and have specific three dimensional structural characteristics as well as specific charge characteristics.

An "antigen" is a molecule or a portion of a molecule capable of being bound by an antibody which is additionally capable of inducing an animal to produce antibody capable of binding to an epitope of that antigen. An antigen may have one, or more than one epitope. The specific reaction referred to above is meant to indicate that the antigen will react, in a highly selective manner, with its corresponding antibody and not with the multitude of other antibodies which may be evoked by other antigens.

The antibodies, or fragments of antibodies, useful in the present invention may be used to quantitatively or qualitatively detect the presence of cells which express the RPTP protein. This can be accomplished by immunofluorescence techniques employing a fluorescently labeled antibody (see below) coupled with light microscopic, flow cytometric, or fluorimetric detection.

The antibodies (of fragments thereof) useful in the present invention may be employed histologically, as in immunofluorescence or immunoelectron microscopy, for in situ detection of RPTP. In situ detection may be accomplished by removing a histological specimen from a patient, and providing the a labeled antibody of the present invention to such a specimen. The antibody (or fragment) is preferably provided by applying or by overlaying the labeled antibody (or fragment) to a biological sample. Through the use of such a procedure, it is possible to determine not only the presence of the RPTP but also its distribution on the examined tissue. Using the present invention, those of ordinary skill will readily perceive that any of a wide variety of histological methods (such as staining procedures) can be modified in order to achieve such in situ detection. Such assays for RPTP typically comprises incubating a biological sample, such as a biological fluid, a tissue extract, freshly harvested cells such as lymphocytes or leucocytes, or cells which have been incubated in tissue culture, in the presence of a detectably labeled antibody capable of identifying RPTP, and detecting the antibody by any of a number of techniques well-known in the art.

The biological sample may be treated with a solid phase support such as nitrocellulose, or other solid support which is capable of immobilizing cells, cell particles or soluble proteins. The support may then be washed with suitable buffers followed by treatment with the detectably labeled RPTP-specific antibody. The solid phase support may then be washed with the buffer a second time to remove unbound antibody. The amount of bound label on said solid support may then be detected by conventional means.

By "solid phase support" is intended any support capable of binding antigen or antibodies. Well-known supports, or carriers, include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

The binding activity of a given lot of anti-RPTP antibody may be determined according to well known methods. Those skilled in the art will be able to determine operative and optimal assay conditions for each determination by employing routine experimentation.

Other such steps as washing, stirring, shaking, filtering and the like may be added to the assays as is customary or necessary for the particular situation.

One of the ways in which the RPTP-specific antibody can be detectably labeled is by linking the same to an enzyme and use in an enzyme immunoassay (EIA). This enzyme, in turn, when later exposed to an appropriate substrate, will react with the substrate in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods which employ a chromogenic substrate for the enzyme. Detection may also be accomplished by visual comparison of the extent of enzymatic reaction of a substrate in comparison with similarly prepared standards.

Detection may be accomplished using any of a variety of other immunoassays. For example, by radioactively labeling the antibodies or antibody fragments, it is possible to detect an RPTP through the use of a radioimmunoassay (RIA) (see, for example, Work, T. S. et al., *Laboratory Techniques and Biochemistry in Molecular Biology*, North Holland Publishing Company, New York, 1978, which is incorporated by reference herein). The radioactive isotope can be detected by such means as the use of a gamma counter or a scintillation counter or by autoradiography.

It is also possible to label the antibody with a fluorescent compound. When the fluorescently labeled antibody is exposed to light of the proper wave length, its presence can then be detected due to fluorescence. Among the most commonly used fluorescent labelling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as $^{152}$Eu, or others of the lanthanide series. These metals can be attached to the antibody using such metal chelating groups as diethylenetriaminepentaacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

The antibody molecules of the present invention may be adapted for utilization in an immunometric assay, also known as a "two-site" or "sandwich" assay. In a typical immunometric assay, a quantity of unlabeled antibody (or fragment of antibody) is bound to a solid support and a quantity of detectably labeled soluble antibody is added to permit detection and/or quantitation of the ternary complex formed between solid-phase antibody, antigen, and labeled antibody.

Typical, and preferred, immunometric assays include "forward" assays in which the antibody bound to the solid phase is first contacted with the sample being tested to extract the antigen from the sample by formation of a binary solid phase antibody-antigen complex. After a suitable incubation period, the solid support is washed to remove the residue of the fluid sample, including unreacted antigen, if any, and then contacted with the solution containing an unknown quantity of labeled antibody (which functions as a "reporter molecule"). After a second incubation period to permit the labeled antibody to complex with the antigen bound to the solid support through the unlabeled antibody, the solid support is washed a second time to remove the unreacted labeled antibody.

In another type of "sandwich" assay, which may also be useful with the antigens of the present invention, the so-called "simultaneous" and "reverse" assays are used. A simultaneous assay involves a single incubation step as the antibody bound to the solid support and labeled antibody are both added to the sample being tested at the same time. After the incubation is completed, the solid support is washed to remove the residue of fluid sample and uncomplexed labeled antibody. The presence of labeled antibody associated with the solid support is then determined as it would be in a conventional "forward" sandwich assay.

In the "reverse" assay, stepwise addition first of a solution of labeled antibody to the fluid sample followed by the addition of unlabeled antibody bound to a solid support after a suitable incubation period is utilized. After a second incubation, the solid phase is washed in conventional fashion to free it of the residue of the sample being tested and the solution of unreacted labeled antibody. The determination of labeled antibody associated with a solid support is then determined as in the "simultaneous" and "forward" assays.

The presence of normally functioning RPTP in a subject can also be tested using direct enzymatic assays, for the tyrosine phosphatase activity. Such biochemical measurements can be performed in vitro, using purified enzymes, allowing precise measurements of enzyme activity, or with membrane preparations, or whole cells, where the net phosphotyrosine level is determined.

In additional embodiments of the present invention, a DNA sequence encoding a RPTP molecule and methods for expressing the DNA sequence are provided. One of ordinary skill in the art will know how to identify and clone additional RPTP molecules, of human or other mammalian species, which have sequence homology to the RPTP molecules described herein, using the genetic sequences and oligonucleotides of the present invention without undue experimentation. Furthermore, manipulation of the genetic constructs of the present invention allow the grafting of a particular ligand-binding receptor domain onto the transmembrane and catalytic portions of the RPTP resulting in chimeric molecules. Non-limiting examples of such chimeric molecules include the RPTP wherein the receptor is an epidermal growth factor receptor, a fibroblast growth factor receptor, and the like. Genetically engineered chimeric receptors are known in the art (see, for example, Riedel, H. et al., *Nature* 324:628–670 (1986)).

Genetic constructs encoding RPTPα, functional derivative thereof, and chimeric molecules such as those described above, can be used in gene therapy. An abnormal or dysfunctional RPTP, which results in disease, may be replaced by infusion of cells of the desired lineage (such as hemopoietic cells, for example) transfected with a normal RPTP. Alternatively, or additionally, cells carrying a chimeric RPTP having a receptor to a ligand of choice (e.g. EGF) can be used for such gene therapy.

The recombinant DNA molecules of the present invention can be produced through any of a variety of means, such as, for example, DNA or RNA synthesis, or more preferably, by application of recombinant DNA techniques. Techniques for synthesizing such molecules are disclosed by, for example, Wu, R., et al. (*Prog. Nucl. Acid. Res. Molec. Biol.* 21:101–141 (1978)). Procedures for constructing recombinant molecules in accordance with the above-described method are disclosed by Sambrook et al. (supra).

The 3' terminus of the recombinant molecule of this invention is preferably treated to render it unsuitable for polymerization. Such treatment may be accomplished by blocking the terminus by chemical means, or by modifying the terminal bases such that they sterically interfere with polymerase action. In a preferred embodiment, such treatment is accomplished by immobilizing the 3' terminus, such as by coupling it to a solid support (such as, for example, glass, plastic, latex, etc.). The support may be of any form (i.e. a sheet, rod, sphere, ovoid, etc. Procedures for such immobilization are well known to those of ordinary skill. In the most preferred embodiment, the 3' end of the recombinant molecule is covalently bound to the solid support. A spacer region may be used to extend the probe outward from the solid support as long as (1) it will not sterically hinder any function or characteristic of the recombinant molecule, and (2) the sequence of the spacer region does not participate in the hybridization or polymerization reactions of the assay. It is typically desirable to immobilize several, and preferably, a large number of such recombinant molecule to the support.

Oligonucleotides representing a portion of an RPTP are useful for screening for the presence of genes encoding such proteins and for the cloning of RPTP genes. Techniques for synthesizing such oligonucleotides are disclosed by, for example, Wu, R., et al., *Prog. Nucl. Acid. Res. Molec. Biol.* 21:101–141 (1978)).

Protein molecules are fragmented as with cyanogen bromide, or with proteases such as papain, chymotrypsin, trypsin, etc. (Oike, Y., et al., *J. Biol. Chem.* 257:9751–9758 (1982); Liu, C., et al., *Int. J. Pept. Protein Res.* 21:209–215 (1983)). Because the genetic code is degenerate, more than one codon may be used to encode a particular amino acid (Watson, J. D., In: *Molecular Biology of the Gene*, 4th Ed., Benjamin/Cummings Publishing Co., Inc., Menlo Park, Calif. (1987)). Using the genetic code, one or more different oligonucleotides can be identified, each of which would be capable of encoding the amino acid. The probability that a particular oligonucleotide will, in fact, constitute the actual XXX-encoding sequence can be estimated by considering abnormal base pairing relationships and the frequency with which a particular codon is actually used (to encode a particular amino acid) in eukaryotic cells. Such "codon usage rules" are disclosed by Lathe, R., et al., *J. Molec. Biol.* 183:1–12 (1985). Using the "codon usage rules" of Lathe, a single oligonucleotide, or a set of oligonucleotides, that contains a theoretical "most probable" nucleotide sequence capable of encoding the RPTP sequences is identified.

Although occasionally an amino acid sequences may be encoded by only a single oligonucleotide, frequently the amino acid sequence may be encoded by any of a set of similar oligonucleotides. Importantly, whereas all of the members of this set contain oligonucleotides which are capable of encoding the peptide fragment and, thus, potentially contain the same oligonucleotide sequence as the gene which encodes the peptide fragment, only one member of the set contains the nucleotide sequence that is identical to the nucleotide sequence of the gene. Because this member is present within the set, and is capable of hybridizing to DNA even in the presence of the other members of the set, it is possible to employ the unfractionated set of oligonucleotides in the same manner in which one would employ a single oligonucleotide to clone the gene that encodes the peptide.

The oligonucleotide, or set of oligonucleotides, containing the theoretical "most probable" sequence capable of encoding the RPTP fragment is used to identify the sequence of a complementary oligonucleotide or set of oligonucleotides which is capable of hybridizing to the "most probable" sequence, or set of sequences. An oligonucleotide containing such a complementary sequence can be employed as a probe to identify and isolate the RPTP gene (Sambrook et al., supra).

A suitable oligonucleotide, or set of oligonucleotides, which is capable of encoding a fragment of the RPTP gene (or which is complementary to such an oligonucleotide, or set of oligonucleotides) is identified (using the above-described procedure), synthesized, and hybridized by means well known in the art, against a DNA or, more preferably, a cDNA preparation derived from cells which are capable of expressing the RPTP gene. Single stranded oligonucleotide molecules complementary to the "most probable" RPTP peptide encoding sequences can be synthesized using procedures which are well known to those of ordinary skill in the art (Belagaje, R., et al., *J. Biol. Chem.* 254:5765–5780 (1979); Maniatis, T., et al., In: *Molecular Mechanisms in the Control of Gene Expression*, Nierlich, D. P., et al., Eds., Acad. Press, N.Y. (1976); Wu, R., et al., *Prog. Nucl. Acid Res. Molec. Biol.* 21:101–141 (1978); Khorana, R. G., *Science* 203:614–625 (1979)). Additionally, DNA synthesis may be achieved through the use of automated synthesizers. Techniques of nucleic acid hybridization are disclosed by Sambrook et al. (supra), and by Hames, B. D., et al. (In: *Nucleic Acid Hybridization, A Practical Approach*, IRL Press, Washington, D.C. (1985)), which references are herein incorporated by reference. Techniques such as, or similar to, those described above have successfully enabled the cloning of genes for human aldehyde dehydrogenases (Hsu, L. C., et al., *Proc. Natl. Acad. Sci. USA* 82:3771–3775 (1985)), fibronectin (Suzuki, S., et al., *EMBO J.* 4:2519–2524 (1985)), the human estrogen receptor gene (Walter, P., et al., *Proc. Natl. Acad. Sci. USA* 82:7889–7893 (1985)), tissue-type plasminogen activator (Pennica, D., et al., *Nature* 301:214–221 (1983)) and human term placental alkaline phosphatase complementary DNA (Kam, W., et al., *Proc. Natl. Acad. Sci. USA* 82:(715–8719 (1985)).

In a alternative way of cloning the RPTP gene, a library of expression vectors is prepared by cloning DNA or, more preferably, cDNA (from a cell capable of expressing RPTP) into an expression vector. The library is then screened for members capable of expressing a protein which binds to anti-RPTP antibody, and which has a nucleotide sequence that is capable of encoding polypeptides that have the same amino acid sequence as RPTP, or fragments thereof. In this embodiment, DNA, or more preferably cDNA, is extracted and purified from a cell which is capable of expressing RPTP protein. The purified cDNA is fragmented (by shearing, endonuclease digestion, etc.) to produce a pool of DNA or cDNA fragments. DNA or cDNA fragments from this pool are then cloned into an expression vector in order to produce a genomic library of expression vectors whose members each contain a unique cloned DNA or cDNA fragment.

An "expression vector" is a vector which (due to the presence of appropriate transcriptional and/or translational control sequences) is capable of expressing a DNA (or cDNA) molecule which has been cloned into the vector and of thereby producing a polypeptide or protein. Expression of the cloned sequences occurs when the expression vector is introduced into an appropriate host cell. If a prokaryotic expression vector is employed, then the appropriate host cell would be any prokaryotic cell capable of expressing the cloned sequences. Similarly, if a eukaryotic expression vector is employed, then the appropriate host cell would be any eukaryotic cell capable of expressing the cloned sequences. Importantly, since eukaryotic DNA may contain intervening sequences, and since such sequences cannot be correct ly processed in prokaryotic cells, it is preferable to employ cDNA from a cell which is capable of expressing RPTP in order to produce a prokaryotic genomic expression vector library. Procedures for preparing cDNA and for producing a genomic library are disclosed by Sambrook et al. (supra).

A DNA sequence encoding the RPTP of the present invention, or its functional derivatives, may be recombined with vector DNA in accordance with conventional techniques, including blunt-ended or staggered-ended termini for ligation, restriction enzyme digestion to provide appropriate termini, filling in of cohesive ends as appropriate, alkaline phosphatase treatment to avoid undesirable joining, and ligation with appropriate ligases. Techniques for such manipulations are disclosed by Sambrook et al., supra, and are well known in the art.

A nucleic acid molecule, such as DNA, is said to be "capable of expressing" a polypeptide if it contains nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene expression. The precise nature of the regulatory regions needed for gene expression may vary from organism to organism, but shall in general include a promoter region which, in prokaryotes, contains both the promoter (which directs the initiation of RNA transcription) as well as the DNA sequences which, when transcribed into RNA, will signal the initiation of protein synthesis. Such regions will normally include those 5'-non-coding sequences involved with initiation of transcription and translation, such as the TATA box, capping sequence, CAAT sequence, and the like.

If desired, the non-coding region 3' to the gene sequence coding for the protein may be obtained by the above-described methods. This region may be retained for its transcriptional termination regulatory sequences, such as termination and polyadenylation. Thus, by retaining the 3'-region naturally contiguous to the DNA sequence coding for the protein, the transcriptional termination signals may be provided. Where the transcriptional termination signals are not satisfactorily functional in the expression host cell, then a 3' region functional in the host cell may be substituted.

Two DNA sequences (such as a promoter region sequence and a RPTP-encoding sequence) are said to be operably linked if the nature of the linkage between the two DNA sequences does not (1) result in the introduction of a frame-shift mutation, (2) interfere with the ability of the promoter region sequence to direct the transcription of the RPTP gene sequence, or (3) interfere with the ability of the RPTP gene sequence to be transcribed by the promoter region sequence. A promoter region would be operably linked to a DNA sequence if the promoter were capable of effecting transcription of that DNA sequence. Thus, to express the protein, transcriptional and translational signals recognized by an appropriate host are necessary.

A promoter is a double-stranded DNA or RNA molecule which is capable of binding RNA polymerase and promoting the transcription of an "operably linked" nucleic acid sequence. As used herein, a "promoter sequence" is the sequence of the promoter which is found on that strand of the DNA or RNA which is transcribed by the RNA polymerase. A "promoter sequence complement" is a nucleic acid molecule whose sequence is the complement of a "promoter sequence." Hence, upon extension of a primer DNA or RNA adjacent to a single-stranded "promoter sequence complement" or, of a "promoter sequence," a double-stranded molecule is created which will contain a functional promoter, if that extension proceeds towards the "promoter sequence" or the "promoter sequence complement." This functional promoter will direct the transcription of a nucleic acid molecule which is operably linked to that strand of the double-stranded molecule which contains the "promoter sequence" (and not that strand of the molecule which contains the "promoter sequence complement").

Certain RNA polymerases exhibit a high specificity for such promoters. The RNA polymerases of the bacteriophages T7, T3, and SP-6 are especially well characterized, and exhibit high promoter specificity. The promoter sequences which are specific for each of these RNA polymerases also direct the polymerase to utilize (i.e. transcribe) only one strand of the two strands of a duplex DNA template. The selection of which strand is transcribed is determined by the orientation of the promoter sequence. This selection determines the direction of transcription since RNA is only polymerized enzymatically by the addition of a nucleotide 5' phosphate to a 3' hydroxyl terminus.

Two sequences of a nucleic acid molecule are said to be "operably linked" when they are linked to each other in a manner which either permits both sequences to be transcribed onto the same RNA transcript, or permits an RNA transcript, begun in one sequence to be extended into the second sequence. Thus, two sequences, such as a promoter sequence and any other "second" sequence of DNA or RNA are operably linked if transcription commencing in the promoter sequence will produce an RNA transcript of the operably linked second sequence. In order to be "operably linked" it is not necessary that two sequences be immediately adjacent to one another.

Thus, as indicated above, in order to function as a promoter, a promoter sequence must be present as a double-stranded molecule. For the purposes of the present invention, the two strands of a functional promoter sequence are referred to as a "transcript" strand and a "complementary" strand. The "transcript" strand is that strand of the duplex which will be transcribed by the RNA polymerase (i.e. which serves as the template for transcription). The "complementary" strand is the strand which has a sequence complementary to the "transcript" strand, and which must be present, and hybridized to the "transcript" strand, in order for transcription to occur. Thus, when the "transcript" strand of a promoter sequence is operably linked to a second sequence, hybridization of the "transcript" strand with the "complement" strand, will, in the presence of a polymerase, result in the transcription of the "transcript" strand, and will produce an RNA transcript using the sequence of the "transcript" strand as a template.

The promoter sequences of the present invention may be either prokaryotic, eukaryotic or viral. Suitable promoters are repressible, or, more preferably, constitutive. Examples of suitable prokaryotic promoters include promoters capable of recognizing the T4 (Malik, S. et al., *J. Biol. Chem.* 263:1174–1181 (1984); Rosenberg, A. H. et al., *Gene* 59:191–200 (1987); Shinedling, S. et al., *J. Molec. Biol.* 195:471–480 (1987); Hu, M. et al., *Gene* 42:21–30 (1986)), T3, Sp6, and T7 (Chamberlin, M. et al., *Nature* 228:227–231 (1970); Bailey, J. N. et al., *Proc. Natl. Acad. Sci. (U.S.A.)* 80:2814–2818 (1983); Davanloo, P. et al., *Proc. Natl. Acad. Sci. (U.S.A.)* 81:2035–2039 (1984)) polymerases; the $P_R$ and $P_L$ promoters of bacteriophage λ (*The Bacteriophage Lambda*, Hershey, A. D., Ed., Cold Spring Harbor Press, Cold Spring Harbor, N.Y. (1973); *Lambda II*, Hendrix, R. W., Ed., Cold Spring Harbor Press, Cold Spring Harbor, N.Y. (1980)); the trp, recA, heat shock, and lacZ promoters of *E. coli*; the α-amylase (Ulmanen, I., et al., *J. Bacteriol.* 162:176–182 (1985)) and the σ- 28-specific promoters of *B. subtilis* (Gilman, M. Z., et al., *Gene* 32:11–20 (1984)); the promoters of the bacteriophages of Bacillus (Gryczan, T. J., In: *The Molecular Biology of the Bacilli*, Academic Press, Inc., N.Y. (1982)); Streptomyces promoters (Ward, J. M., et al., *Mol. Gen. Genet.* 203:468–478 (1986)); the int promoter of bacteriophage λ; the bla promoter of the β-lactamase gene of pBR322, and the CAT promoter of the chloramphenicol acetyl transferase gene of pPR325, etc. Prokaryotic promoters are reviewed by Glick, B. R. (*J. Ind. Microbiol.* 1:277–282 (1987)); Cenatiempo, Y. (*Biochimie* 68:505–516 (1986)); Watson, J. D. et al. (In: *Molecular Biology of the Gene*, Fourth Edition, Benjamin Cummins, Menlo Park, Calif. (1987)); and Gottesman, S. (*Ann. Rev. Genet.* 18:415–442 (1984)). Preferred eukaryotic promoters include the promoter of the mouse metallothionein I gene (Hamer, D., et al., *J. Mol. Appl. Gen.* 1:273–288 (1982)); the TK promoter of Herpes virus (McKnight, S., *Cell* 31:355–365 (1982)); the SV40 early promoter (Benoist, C., et al., *Nature (London)* 290:304–310 (1981)); and the yeast gal4 gene promoter (Johnston, S. A., et al., *Proc. Natl. Acad. Sci. (USA)* 79:6971–6975 (1982); silver, P. A., et al., *Proc. Natl. Acad. Sci. (USA)* 81:5951–5955 (1984)). All of the above listed references are incorporated by reference herein.

Strong promoters are preferred. Examples of such preferred promoters are those which recognize the T3, SP6 and T7 polymerases, the $P_L$ promoter of bacteriophage λ, the recA promoter and the promoter of the mouse metallothionein I gene. A most preferred promoter for eukaryotic expression of RPTP is an SV40 promoter such as that driving transcription in the pLSV vector (Livneh, E., et al., (1986) *J. Biol. Chem.* 261, 12490–12497). The sequences of such polymerase recognition sites are disclosed by Watson, J. D. et al. (In: *Molecular Biology of the Gene*, Fourth Edition, Benjamin/Cummings Publishing Co., Inc., Menlo Park, Calif., (1987)).

Having now generally described the invention, the same will be more readily understood through reference to the following example which is provided by way of illustration, and is not intended to be limiting of the present invention, unless specified.

6. EXAMPLE: ISOLATION AND ANALYSIS OF MURINE RPTPα cDNA CLONES

6.1. LIBRARY SCREENING

A mouse BALB/C brain cDNA library in λgt11 (obtained from Dr. Y. Citri) was screened at relaxed stringency (6XSSC, 5XDenhardts, 0.1% SDS, 50 mM Tris pH 7.5, 1 mM EDTA, 0.1 mg/ml salmon sperm DNA, hybridization temperature 50° C.) using as a probe a 2400 bp BglII-AccI fragment representing the intracellular and trans-membrane domains of the human T200 glycoprotein (Ralph, S. J. et al., (1987) *EMBO J.* 6, 1251–1257), which had been $^{32}$P-labeled using the random-priming method. Washing was performed at 50° C. in 6XSSC, 0.1%SDS. Out of $10^6$ clones, 51 positives were picked, selected and characterized by restriction enzyme mapping. EcoRI fragments of 0.95, 1.6 and 0.3 Kb isolated from the phage clone containing the longest insert (λ-109) were subcloned into the Bluescript KS plus and minus vectors. A series of nested deletions were generated by taking use of restriction sites common to the cloned cDNA fragments and the polylinker region of the plasmid vector. The individual restriction sites used are indicated in FIG. 1E. Single stranded DNA was prepared from these constructs, and used as a template for sequence analysis using the dideoxynucleotide chain termination method (Sequenase, United States Biochemical). All regions were sequenced on both strands. The relative order and orientation of the EcoRI fragments in the recombinant phage was determined by restriction mapping. To ascertain that the different EcoRI fragments did not correspond to unrelated cDNA fragments ligated together during the process of library construction, restriction mapping was also performed on a different and independent isolate, λ- 113.

6.2. RESULTS

Brain tissue already has proven to be a rich source of many types of tyrosine kinases, and recent biochemical evidence has also indicated the existence of multiple forms of PTPase activity (Jones, S. W. et al., (1989) *J. Biol. Chem.* 264, 7747–7753). In order to search for new receptor-type PTPase, the present inventors screened at low stringency a mouse brain cDNA library, using as a hybridization probe the intracellular domain of human CD45 containing two tandem PTPase domains (Tonks, N. K. et al., supra; Charbonneau, H. et al., supra; Ralph, S. J. et al., supra). Positive clones were classified by cross-hybridization and restriction mapping into several categories, and the longest phage insert (λ-109) corresponding to the most abundantly represented class was chosen for subcloning and further analysis.

The result of the nucleotide sequence analysis is shown in FIGS. 1A–1D, which presents the nucleotide sequence (SEQ ID NO:4) and the amino acid sequence (SEQ ID NO:3) of murine RPTPα. Conceptual translation of the cDNA sequence reveals the existence of a major open reading frame of 794 amino acids, assuming that translation icnitiates at nucleotide 259 (an in-frame stop codon is present 60 nucleotides upstream). The putative initiation methionine codon is embedded in a relatively standard environment for initiation of translation (Kozak, M., (1987) *Nucl. Ac. Res.* 15, 8125–8148), and is followed by a characteristic hydrophobic stretch of amino acids which probably function as a signal peptide. According to the "-3,- 1" rule (von Heijne, G. (1986) *Nucl. Ac. Res.* 14, 4683–4690), residues 20 and 25 are both likely candidates to constitute the N-terminus of the mature protein. A second hydrophobic stretch is found between amino acids 143 and 166, and is followed by a series of highly charged residues, consistent with the stop-transfer signals found to be associated with many membrane-spanning domains. The predicted intracellular domain of the protein consists of two tandem repeats having 44% sequence identity between each other (residues 259–486 and 552–776). Each of these repeats display significant sequence identity with the intracellular catalytic domains of the previously described transmembrane PTPase CD45 (Ralph, S. J. et al., supra) and LAR (Streuli, M. et al., (1988), supra) (45% and 53% amino acid sequence identity, respectively).

In contrast, the EMBL and GENBANK databases contain no significant homology to known sequences of the putative extracellular domain of the encoded protein. Features of the extracellular domain include a uniquely high content of serine and threonine residues (>32%), the absence of cysteine residues, and the presence of 8 potential N-linked glycosylation sites.

It was concluded that the isolated cDNA encoded a new member of the transmembrane PTPase family having a novel type of extracellular domain. In view of its receptor-like structure and the likelihood that additional members of this family can be found based on the present experimental evidence, the name muRPTPα (murine receptor protein tyrosine phosphatase-α) was chosen to designate this protein.

7. EXAMPLE: CHROMOSOMAL LOCALIZATION OF THE MOUSE RPTPα GENE

STS/A, 020/A, CXS and OXA recombinant inbred (RI) mice, and CXB RI strains N, O, P, Q, and R were a gift from Dr. Jo Hilgers (The Netherlands Cancer Institute). All other inbred mice were purchased from the Jackson Laboratory (Bar Harbor, Me.). Backcross (BC) animals were bred at New York University with inbred progenitors obtained from the Jackson Laboratory. The female parent is named first in all crosses and F1 designations.

Spleen genomic DNA from the AKXD, AKXL, BXD, BXH and G, H, I SWXL RI strains, and from CXB, RI strains D, E, G, H, I, J, and K was purchased from the DNA Resource at the Jackson Laboratory. For all other mice, genomic DNA was prepared from crude liver nuclei by a standard sequence of protease digestion, phenol and chloroform extraction, and ethanol precipitation. Mouse genomic DNAs were subjected to Southern blotting analysis by slight modifications of standard procedures, exactly as described previously (Silver, J. (1985) *J. Hered.* 76, 436–440). A 1.8 kb EcoRI fragment corresponding to the intracellular phosphatase domains of RPTPα, and a 0.7 kb SacII-EcoRI fragment corresponding to its extracellular and transmembrane domains, were cloned into the Bluescript KS vector, yielding plasmids p109 and p923, respectively.

DNA restriction fragment length variants associated with the Il-1a locus (interleukin-1 alpha) were detected by Southern blotting as described previously (D'Eustachio, P. et al., (1987) *Immunogenetics* 26, 339–343). The significance of deviations from 1:1 segregation for pairs of markers was calculated by the Bayesian method of Silver and Buckler (Silver, J. et al., (1986) *Proc. Natl. Acad. Sci. USA* 83, 1423–1427); Blank, R. D. et al., (1988) *Genetics* 120, 1073–1083). Map distances were estimated from recombination fractions measure in RI strain sets according to B. A. Taylor (in: Morse, H. C. III, ed., *Origins of Inbred Mice*, Academic Press, New York, 1978, pp. 423–438), and their associated 95% binomial confidence limits were calculated according to Silver (1985, supra). Probabilities of alternative orders of trios of markers were calculated according to D.

Southern blotting analyses of genomic DNA from inbred strains of mice revealed two useful restriction length variants, one visualized with a probe corresponding to the intracellular domain of murine RPTPα (p109) and one visualized with an extracellular and transmembrane domains probe (p923). Together, these variants allowed definition of three allelic forms of muRPTPα among the 10 inbred strains of mice surveyed (Table I).

TABLE I

Restriction Fragment Length Variants Detected by muRPTPα Probes

| Allele | Probe p109 | p923 | Mouse Strains |
|---|---|---|---|
| a | 9.4 | 5.9 + 4.2 | BALB/cJ |
| b | 6.5 | 4.2 + 1.8 | C57BL/6J, C57L/J, DBA/2J |
| c | 6.5 | 5.9 + 4.2 | C3H/HeJ, 020/A, AKR/J, SWR/J, SJL/J, STS/A |

Liver genomic DNA digested with Taq1 restriction endonuclease was analyzed by Southern blotting. Fragment sizes in kilobases are shown.

Inheritance of these alleles in RI mice was scored. Comparison of the strain distribution patterns observed for murine RPTPα (Table II) with those previously observed for other markers of known chromosomal location in these mice indicated close linkage between the muRPTPα and Il-1a (Interleukin-1) loci on chromosome 2 (3 RI strains among 89 examined). This degree of concordance has a probability of less than 0.00001 of occurring as a chance event were the loci unlinked. The observed fraction of recombinant strains indicates a map distance of 0.9 cM between the loci (95% confidence limits 0.2–0.6 cM).

TABLE II

Inheritance of muRPTPα and Il-1a DNA sequence variants in RI strains of mice

AKXD strain:

| | 1 | 2 | 3 | 6 | 7 | 8 | 9 | 10 | 11 | 12 | 13 | 14 | 15 | 16 | 18 | 20 | 21 | 22 | 23 | 24 | 25 | 26 | 27 | 28 |
|---|---|---|---|---|---|---|---|---|---|---|---|---|---|---|---|---|---|---|---|---|---|---|---|---|
| Il-1a | D | D | D | A | D | A | A | D | D | A | D | A | D | A | D | A | D | A | D | A | A | A |
| R-PTP-α | D | D | D | A | D | A | A | D | A | A | D | A | D | A | D | A | D | A | D | A | A | A |

AKXL strain:

| | 5 | 6 | 7 | 8 | 9 | 12 | 13 | 14 | 16 | 17 | 19 | 21 | 24 | 25 | 28 | 29 | 37 | 38 |
|---|---|---|---|---|---|---|---|---|---|---|---|---|---|---|---|---|---|---|
| Il-1a | L | L | L | A | L | A | L | L | A | A | L | A | L | A | L | A | L | S |
| R-PTP-α | L | L | L | A | L | A | L | L | A | A | L | A | L | A | L | A | L | S |

SWXL strain:

| | 14 | 12 | 14 | 15 | 16 | 17 |
|---|---|---|---|---|---|---|
| Il-1a | L | S | L | L | S | L |
| R-PTP-α | L | S | L | L | S | L |

CXB strain:

| | D | E | G | H | I | J | K | N | O | P | Q | R |
|---|---|---|---|---|---|---|---|---|---|---|---|---|
| Il-1ha | C | B | B | C | B | B | B | C | C | C | C | B |
| R-PTP-α | C | B | B | C | B | B | B | C | B | C | C | B |

CXS strain:

| | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| Il-1ha | T | T | T | C | C | T | T | T | C | T | C | C | T | C |
| R-PTP-α | T | T | T | C | C | T | C | T | C | T | C | C | T | C |

BXH STRAIN:

| | 2 | 3 | 4 | 6 | 7 | 8 | 9 | 10 | 11 | 12 | 14 | 19 |
|---|---|---|---|---|---|---|---|---|---|---|---|---|
| Il-1a | B | B | H | H | B | H | B | H | B | H | H |  |
| R-PTP-α | B | B | H | H | B | H | B | H | B | H | H |  |

BXJ strain:

| | 1 | 2 |
|---|---|---|
| Il-1a | B | B |
| R-PTP-α | B | B |

RI strains were typed for alleles of muRPTPα and Il-1a by Southern blotting of TaqI-digested DNA (see Table I and D'Eustachio, P. et al., *Immunogenetics* 26, 339–343 (1987)). Il-1a alleles for AKXD, CXB strains D–K, and BXH mice were disclosed in D'Eustachio et al., supra). All RI strains are homozygous for one of the progenitor strain alleles at each locus; the allele is indicated by an uppercase letter corresponding to the parent strain as follows:
A, AKR/J; B, C57BL/6J; C, BALB/C; D, DBA/2J; H, C3H/HeJ; J, SJL/J; L, C57L/J; S, SWR/J; T, STS/A.

Bishop ((1985) *Genet. Epidemiol.* 2, 349–361, equation 1). Computations were carried out on a VAX6000-410 computer.

Following the inheritance of muRPTPα, Il-1a and a (nonagouti) among progeny of reciprocal backcross between the C57BL/6J and SWR/J strains confirmed the linkage of muRPTPα and Il-1a, and suggested an order for the two genes (Table III). Of 150 progeny, 14 were recombinant between muRPTPα and a, and one was recombinant between muRPTPα and Il-1a. If the locus order were: centromere —Il—1a—muRPTPα—a, these results would require the occurrence of no double crossovers; alternative orders require one or 14 such events, and, evaluated according to the method of Bishop (supra), are at least 9.5-fold less likely. The distance between Il-1a and muRPTPα, 0.6 cM (95% confidence limits: 0.1–2.4 cM), agrees within sampling fluctuation with the distance estimated from the RI strain data. Comparison of these results with results recently obtained for Bmp-2a (Bone morphogenic protein 2a, Dickinson, M. E. et al., (1990) *Genomics* 6, 505–520) suggests that the two genes may be closely linked, although there is no obvious structural homology between them.

TABLE III

Linkage Among Markers of
Chromosome 2 in Backcross BC Progeny

A. ALLELE COMBINATIONS FROM $F_1$ PARENT AND
THE ACTUAL NUMBERS OF C57BL/6J-DERIVED (b)
AND SWR/J-DERIVED (s) ALLELES FOUND

| LOCUS | POSSIBLE ALLELE COMBINATION | | | | | | | | $\Sigma$b | $\Sigma$s |
|---|---|---|---|---|---|---|---|---|---|---|
| Il-1a | b | s | b | s | b | s | b | s | 76 | 74 |
| R-PTP-α | b | s | b | s | s | b | s | b | 77 | 73 |
| a | b | s | s | b | s | b | b | s | 69 | 71 |

B. NUMBERS OF PROGENY FROM EACH BACKCROSS
THAT INHERITED EACH POSSIBLE
ALLELE COMBINATION.

| BACKCROSS | NUMBER OF PROGENY | | | | | | | |
|---|---|---|---|---|---|---|---|---|
| $F_1 \times B$ | 44 | 43 | 9 | 1 | 0 | 1 | 0 | 0 |
| $B \times F_1$ | 21 | 27 | 2 | 2 | 0 | 0 | 0 | 0 |
| | 135 | | 14 | | 1 | | 0 | |

150 progeny from BC between (C57BL/6J × SWR/J)$F_1$ (F1) and C57BL/6J (B) mice were typed visually for inheritance of the nonagouti (a) marker and, by Southern blotting, for alleles of the muRPTPα and Il-1a loci.

8. EXAMPLE: EXPRESSION OF MURINE RPTPα RNA

8.1. Northern Analysis

Poly A$^+$ RNA was prepared from adult mouse tissues and cell lines by oligo(dT) selection as described (Vennström, B. et al., (1982) *Cell* 28, 135–143), fractionated (5 μg per lane) on a formaldehyde-containing gel and transferred to nitrocellulose (Hybond C, Amersham) using standard procedures. A $^{32}$P-labelled probe was prepared by primer extension on a single-stranded template consisting of the entire λ-109 cDNA cloned into the EcoRI site of the Bluescript vector in the antisense orientation, using the Klenow fragment of DNA polymerase for elongation from an annealed T7 primer, in the presence of $^{32}$P-dATP. Hybridization was performed at 42° C. in 50% formamide, 5xSSC, 25 mM KPO$_4$, 5X Denhardt's, 10 μg/ml salmon sperm DNA, and 10% sulfate. Washing was done at 48° C. in 0.1X SSC, 0.1% SDS. Higher stringency washes (58° C.) of the filter did not noticeably affect the hybridization pattern.

8.2. EXPRESSION OF THE MURINE RPTPα PROTEIN.

The entire cDNA insert from phage λ-109 was released as one fragment from the phage using partial EcoRI digestion, and cloned into the Bluescript KS vector. A cDNA fragment lacking most of the untranslated leader sequence (starting from the Sac II site at position 226; see FIG. 1E) was subcloned into the SV40 promoter driven pLSV-vector (Livneh, E., et al., (1986) *J. Biol. Chem.* 261, 12490–12497), and the resulting plasmid DNA (pLSV-PTP-α) was transfected into COS cells using the DEAE-dextran method (Lopata, M. A. et al., (1984) *Nucl. Ac. Res.* 12, 5707–5717). The expression vector pLSVΔC encoding the N-terminally truncated muRPTPα protein was used as a control in the immunoprecipitation experiment.

8.3. Results

Poly A$^+$ RNA from various mouse tissues was prepared to study the expression of the muRPTPα gene. Northern analysis (FIG. 2) revealed a wide pattern of expression. A 3.0 kB mRNA was present in all tissues examined, except spleen, with brain and kidney showing the highest levels of expression. An mRNA of similar size could also be observed in the NIH-3T3 mouse fibroblast line, 2.2, and the prepro-B lymphoid cell line, BAF (FIG. 2). Shorter exposure of the Northern blot clearly showed that in addition a second mRNA species of very similar size (3.2 kb) is present in several tissues (e.g. brain) in lower amounts. The data also suggest that, although a poly A tail and a polyadenylation signal at the 3' end of the cDNA sequence were not observed, the isolated cDNA clone (2872 nucleotides) closely matches the full length of the mRNA.

9. EXAMPLE: TRANSIENT EXPRESSION OF THE MURINE RPTPα PROTEIN

9.1. ANTIBODY PREPARATION AND IMMUNOPRECIPITATION

Rabbits were injected with a synthetic peptide corresponding to the predicted C-terminus of the muRPTPα protein (residues 777–794) coupled to BSA using EDCI (1-ethyl-3-(dimethylaminopropyl)carbodiimide) as a coupling reagent. Antigen was injected intradermally and subcutaneously in an emulsion of 1 mg peptide and complete Freund's adjuvant. Three booster injections were given at 2–3 week intervals with 0.5 mg peptide and incomplete adjuvant. An antiserum obtained using this method was designated "2A." Metabolic [$^{35}$S]-methionine labelling, cell extract preparation (60 hours after transfection) and indirect immunoprecipitation using protein-A-Sepharose were performed using standard procedures (Yarden, Y. et al., (1987) *EMBO J.* 6, 3341–3351).

9.2. Results

In order to determine the size of the mature protein, we cloned the muRPTPα cDNA with the exception of most of the untranslated leader into the pLSV vector (Livneh, E., et al., (1986) *J. Biol. Chem.* 261, 12490–12497) under the control of the SV40 promoter, yielding the expression vector pLSV-PTP-α. The vector was transfected into COS cells, and 60 hours later [$^{35}$S]-methionine labelled total cell extracts were prepared for immunoprecipitation, using antiserum 2A.

As seen in FIG. 3, the antiserum recognized several bands, one of which, a diffuse band of 130 kDa (arrow), was only present in immunoprecipitates from transfected cells (lane 5), but not from mock-transfected cells (lane 3) (transfected with pLSV without the muRPTPα cDNA). Precipitation could be competed out by the peptide used for immunization (lane 6).

The difference between the predicted (88 kDa) and observed (130 kDa) molecular weights for the muRPTPα protein is ascribed to its extensive glycosylation.

As an additional control for the specificity of the antiserum, we also transfected COS cells with a N-truncated version of the muRPTPα cDNA (starting at amino acid 214, and thus lacking the transmembrane and extracellular domains) in the same vector. A new and abundant protein with an apparent molecular weight of 55 kDa appeared in immunoprecipitates from cells transfected with this vector, which was again competed out by the antigenic peptide (lanes 7 and 8). The higher abundance of the truncated protein as compared to the mature muRPTPα protein was a consistent observation over several independent transfection experiments.

9.3. GENERAL DISCUSSION FOR SECTIONS 6–9

The Examples presented above describe the identification of a novel receptor-like PTPase, RPTPα, having a broad pattern of expression. RPTPs are therefore expected to have widespread functions beyond the regulation of lymphoid cell activity, as was previously thought based on study of CD45.

Studies using monoclonal antibodies directed against the extracellular domain of CD45 proteins showed that cross-linking of RPTPs can have profound effects on various cellular activities, although a direct effect on PTPase enzymatic activity remains to be shown. However, since ligand-induced receptor clustering is a central event in transmembrane signalling by receptor tyrosine kinases (Ullrich, A. et al., supra), it is proposed by the inventors that putative extracellular ligands for RPTPs have the capacity to regulate the activity of RPTPs in vivo.

In a manner analogous to that proposed for receptor tyrosine kinases (PTKs), RPTPs are proposed to have arisen through several gene fusion events between an ancestral PTPase domain, and domains capable of binding extracellular ligands (Ullrich, A. et al., Hanks, S. K. et al., supra).

The variety of extracellular domains potentially joined to PTPase domains to form receptor-like proteins are expected to reflect the range of possible ligands able to act by similar mechanisms. The availability of cloned RPTPs, such as those disclosed herein, will be valuable in determining their substrate specificity and in understanding their function and manipulating their activity.

RPTPs might have a broad specificity directed towards major tyrosine kinase substrates, with their different extracellular domains mainly allowing for different regulatory mechanisms responsive to different signals in the extracellular environment. Based on this view, they are expected to modulate the responsiveness of a cell to those polypeptide growth factors which act through receptor protein tyrosine kinases. As with PTK's, ligand binding would lead to an activation of enzymatic activity. Viewed in this light, RPTPα and molecules like it, would be negative growth regulators and can be considered potential recessive oncogenes.

For instance, deletion of portions of murine chromosome 2, to which RPTPα maps, appears to be an early event in the development of radiation-induced myeloid leukemia in SJL/J mice (Tracktenbrot, L. et al., (1988) *Leukemia* 2, 545–550), consistent with the recessive oncogene notion. Furthermore, rearrangements involving human chromosome 20 (to which the human RPTPα gene maps) have been linked to human lymphoid leukemia (Mitelman, F. (ed.) *Catalog of Chromosome Aberrations in Human Cancer*, A. Liss, New York).

Alternatively, RPTPα may act in a manner analogous to that proposed for the interaction between CD45 and c-lck (Oostergaard, H. L. et al., (1989) *Proc. Natl. Acad. Sci. USA* 86, 8959–8963; Mustelin, T. et al., (1989) *Proc. Natl. Acad. Sci. USA* 86, 6302–6306). According to this view, RPTPα would dephosphorylate negative regulatory sites in membrane-associated PTKs which are not receptors, and which are more widely expressed than lck (such as, for example, the tyr$^{527}$ site in pp60$^{c-src}$). Acting in this manner, RPTPα would be implicated in positive growth control and differentiation.

Although the inventors do not intend to be bound by any particular theory, the high interspecies conservation of the catalytic domains of the various RPTPs indicate an important role for these receptors in cell growth control.

10. EXAMPLE: ISOLATION AND CHARACTERIZATION OF HUMAN RPTP CDNA (See, also, Kaplan, R. et al., *Proc. Natl. Acad. Sci. USA* 87:7000–7004 (1990))

10.1. Materials

Restriction endonucleases and modifying enzymes were purchases from Boehringer-Mannheim or New England Biolabs. Taq DNA polymerase was from Perkin-Elmer/Cetus. The λgt11 forward and reverse primers (24-mers) used in the polymerase chain reactions as well as all sequencing primers, were synthesized on an automated DNA synthesizer (Applied Biosystems, model 380A) using either methoxy or β-cyanoethyl phosphoramidites (House, C., et al., *J. Biol. Chem.*, 262:772–777 (1987)). The λgt11 human brainstem cDNA library was obtained form the American Type Culture Collection (no. 37432). The LCA (CD45) clone used as a probe for screening the library was received from E. H. Fischer (University of Washington, Seattle). All sequencing reactions were performed using the Sequenase kit (United States Biochemical).

10.2. Methods

Approximately 300,000 plaques from a 80 gt11 cDNA library of 1-day-old human infant brainstem were screened on duplicate nitrocellulose filters under conditions of reduced stringency with a nick-translated LCA probe that spanned both conserved phosphatase domains (Charbonneau, H. et al., 1989, supra).

Hybridization was carried out at 55° C. overnight in a solution of 5x SSPE (SSPE is 10 mM NaH$_2$PO$_4$, pH 7.4/0.18M NaCl/1 mM EDTA) containing 0.25% nonfat dry milk, 0.1% SDS, and $^{32}$P-labeled LCA probe at 10$^6$ cpm/ml. The filters were washed three times for 20 min at 55° C. in 2 x SSPE/0.2% SDS and then processed for autoradiography. This screen yielded 79 duplicate positives; 12 of these, showing varying degrees of hybridization to the LCA probe, were plaque-purified by repetition screening with the same probe. The polymerase chain reaction (Saiki, R. K., et al., *Science*, 230:1350–1354 (1985)) was then used to determine the sizes of the cDNA inserts. The DNA templates consisted of portions of the eluates from each pure plaque, heated at 75° C. for 15 min. to release the DNA. The templates were primed with the λgt11 forward and reverse primers. The reaction mixtures (0.1 ml) were prepared as described (Dionne, C. A. et al., *Biotechniques* 8:190–194 (1990)). Amplification was achieved by performing 30 cycles, each including 1.5 min of denaturation at 94° C., 2 min of annealing at 65° C., and 4 min of extension at 72° C., in an automated Perkin-Elmer/Cetus DNA thermal cycler. A portion of each sample (15 μl) was analyzed by electrophoresis through a 1% agarose gel containing ethidium bromide at 1 μg/ml (Sambrook et al., supra). DNA was prepared from the 4 largest clones by using LambdaSorb (Promega) and then digested with EcoRI. The fragments were subcloned separately into the EcoRI site of M13mp18 for sequencing. Nucleotide sequences were determined by the dideoxynucleotide chain-termination method (Sanger, F., et al., *Proc. Natl. Acad. Sci. USA*, 74:5463–5467 (1977)) using modified T7 polymerase (Tabor, S. et al., *Proc. Natl. Acad. Sci. USA* 84:4767–4771 (1987)).

All computer analyses of sequence data were performed on a Micro VAX II using programs written by IntelliGenetics. DNA sequences were analyzed and assembled using the GEL program. Hydrophobic analyses of proteins were based on the algorithm of Kyte and Doolittle (Kyte, J. et al., *J. Mol. Biol.* 157:105–132 (1982)), as implemented in the PEP program. Protein sequence alignments were done using the GENALIGN program (Sobel, E. et al., *Nucleic Acids Res.* 14:363–374 (1985); Karlin, S. et al., *Mol. Biol. Evol.* 1:357–370 (1984); Needleman, S. B. et al., *J. Mol. Biol.* 48:443–453 (1970)). Initial alignments were done using the Jimenez-Montano protein alphabet (Jimenez-Montano, M. et al., *Proc.* 7th Int'l. Biophysics Congress, 1981, Mexico City).

10.3. Results

In an effort to identify new members of the PTPase family, 300,000 plaques from a human infant brainstem cDNA library in λgt11 were screened under nonstringent conditions using a nick-translated LCA probe that spanned both conserved phosphatase domains. Four of the initial 79 duplicate positives were sequenced in the entirety. Two clones, 31-4 and 27-1, contained overlapping portions of the entire coding region of a human RPTP (huRPTP) that was designated RPTPα (FIGS. 4 and 8). The combined lengths of clones 31-4 and 27-1 equaled 3615 bp (FIG. 4A), encoding a protein of 802 amino acids (FIG. 4D) and containing an additional 695 bp and 510 bp, respectively, of 5' and 3' untranslated region. Two of the four clones contained portions of genes coding for two additional RPTPs which have been designated β and γ (FIGS. 5A–5B and 5C–5D). Like RPTPα, these two proteins contain typical hydrophobic transmembrane regions and distinct extracellular domains, indicating that they also represent separate RPTPs.

Thus, the nucleotide sequence of human RPTPα (SEQ ID NO:2) is shown in FIGS. 8A–8C. The deduced amino acid sequence of the human RPTPα protein (SEQ ID NO:1) is shown in FIGS. 4D and 8A–8C.

The murine homologue of human RPTPα is described in Sections 6–9, above. A comparison of the mouse and human protein sequences (FIG. 4D) indicates that, with the exception of the extracellular domain, where some variability exists, only 5 residues are found to differ between the two proteins.

An examination of the structure of human RPTPα reveals the following features: a relatively short extracellular domain consisting of 150 residues that includes a hydrophobic signal peptide containing the only cysteine in this region. There are eight potential N-glycosylation sites, as well as a number of potential O-glycosylation sites (since this domain is rich in serine and threonine). The extracellular domains of RPTPα and the LCA and LAR molecules described by others appear to be structurally unrelated. Human RPTPα has a hydrophobic transmembrane region anchored on both sides by charged residues. This is followed by the two tandemly repeated conserved phosphatase domains of about 235 residues each, which are separated by 57 amino acids, typical of RPTPs such as LCA, LAR and the two Drosophila PTPases, DLAR and DPTP.

FIGS. 5A–5B and 5C–5D show the alignments of the amino acids within the first and second conserved phosphatase domains, respectively (SEQ ID NO's: 5–9 and SEQ ID NO's: 10–14, respectively), of LCA and RPTPs α, β, and γ. It is readily apparent that among the four RPTPs, β and γ share the greatest sequence similarity. It was reported (Hunter, T. et al. supra) that among the sequences of the conserved phosphatase domains of PTPase 1B, LCA, LAR, DLAR and DPTP there are 29 invariant residues. While many of these residues are also present in both phosphatase domains of RPTPα, β, and γ, it is interesting that the second conserved phosphatase domains of both β and γ lack a number of these amino acids, including the two cysteines at positions 104 and 201 in phosphatase domain 2 of LCA (see FIGS. 5C–5D).

10.4. Discussion

The sequences of the conserved phosphatase domains of the three human RPTPs identified here (α, β, and γ) have been compared with one another as well as with those of LCA, LAR, and two soluble PTPases, placental phosphatase 1B and T-cell PTPase (Table IV). The two soluble enzymes have a sequence identity of 70%; however, when each is compared with the RPTPs (Phosphatase domains PD1 or PD2), this number drops to 29–42%. In all cases, the soluble PTPases showed a greater identity with PD1 than with PD2 of the RPTPs. RPTPα appears to be most related to LAR, since their PD1 sequences are 56% identical and their PD2 sequences are 52% identical. The conserved domains of RPTPβ and RPTPγ are most related to each other, even more so than are the two soluble PTPases, β and γ being 75% identical in both PD1 and PD2. It is interesting that, in general, the sequence relationship between PD1 and PD2 within any RPTP appears to be no closer than that seen between different members of the family, i.e., the identities between PD1 and PD2 range from a high of 47% for LAR to a low of 29% for RPTP γ.

While the cytoplasmic domains of RPTPα, β, and γ are highly conserved, the extracellular domains of these receptors are unrelated to one another as well as to those of LAR and LCA. This suggests that each of these receptors has its own distinct ligand. It is likely that the binding of such ligands to the RPTPs plays a crucial role, together with growth factor receptors exhibiting PTKase activity, in the regulation of the level of tyrosine phosphorylation of targets proteins involved in signal transduction. The diversity of the RPTPs described herein reveals the existence of a multigene family. Greater understanding of structure-function relationships among these membrane receptors will provide important insights into the mechanisms involved in cell growth, differentiation, and oncogenesis.

TABLE IV

| | PTPase 1B | T-cell PTPase | LCA PD1 | LCA PD2 | LAR PD1 | LAR PD2 | RPTPaseα PD1 | RPTPaseα PD2 | RPTPase-β PD1 | RPTPase-β PD2 | RPTPase-γ PD1 | RPTPase-γ PD2 |
|---|---|---|---|---|---|---|---|---|---|---|---|---|
| PrPase 1B | 100 | ... | ... | ... | ... | ... | ... | ... | ... | ... | ... | ... |
| T-cell PTPase | 70 | 100 | ... | ... | ... | ... | ... | ... | ... | ... | ... | ... |
| LCA PD1 | 37 | 36 | 100 | ... | ... | ... | ... | ... | ... | ... | ... | ... |
| LCA PD2 | 30 | 26 | 31 | 100 | ... | ... | ... | ... | ... | ... | ... | ... |
| LAR PD1 | 39 | 42 | 50 | 28 | 100 | ... | ... | ... | ... | ... | ... | ... |
| LAR PD2 | 29 | 33 | 42 | 34 | 45 | 100 | ... | ... | ... | ... | ... | ... |
| RVTPα PD1 | 36 | 39 | 50 | 32 | 56 | 45 | ... | ... | ... | ... | ... | ... |
| RPTPα PD2 | 33 | 34 | 40 | 32 | 41 | 52 | 43 | 100 | ... | ... | ... | ... |
| RPTPβ PD1 | 35 | 39 | 41 | 31 | 33 | 41 | 47 | 33 | 100 | ... | ... | ... |
| RPTPβ PD2 | 29 | 30 | 31 | 30 | 31 | 34 | 31 | 37 | 30 | 100 | ... | ... |
| RPTPγ PD1 | 35 | 34 | 32 | 29 | 39 | 36 | 34 | 32 | 75 | 27 | 100 | ... |
| RPTPγ PD2 | 29 | 29 | 30 | 28 | 32 | 36 | 31 | 34 | 33 | 75 | 29 | 100 |

Header spans: "Identities Between Conserved Phosphatase Domains (Percent)"

Alignments of the conserved phosphatase domains were carried out as described above. The regions compared are designated in FIG. 4C and FIGS. 5A–5B and 5C–5D. PD = phosphatase domain.

11. EXAMPLE: EXPRESSION OF HUMAN RPTPα BY NORTHERN BLOT ANALYSIS

Samples containing either 20 μg of total RNA or 2 μg of poly(A)$^+$ RNA were resolved in a formaldehyde/agarose gel and transferred to nitrocellulose. RPTPα and β-actin probes were labeled by random priming (Sambrook et al., supra). Hybridizations and washes were carried out at 65° C. as described (Church, G., et al., Proc. Natl. Acad. Sci. USA, 81:1991–1995 (1984)). Blots hybridized with the RPTPα probe were exposed to XAR-2-x-ray film (Kodak) with an intensifying screen for 72 hr at −80° C. Results were obtained from the actin-probe blots after 15 hr under the same conditions.

RPTPα expression was examined in various cell lines and tissues (FIG. 6). The results indicate the presence of two major RNA transcripts of approximately 4.3 and 6.3 kb, respectively. The larger of the two species appears to be more prevalent in fetal tissues and in particularly prominent in the poly(A)$^+$ fetal liver sample, where there is also the highest relative amount of the 4.3-kb transcript. It is possible that the different expression of the two transcripts is developmentally regulated and/or a result of alternative splicing mechanisms, a feature seen with LCA (Ralph, S. J. supra). The adult brain shows relatively less expression of RPTPα. The results suggest that RPTPα is expressed to some degree throughout many tissues. Murine RPTPα was also shown to be expressed in many tissues and cell lines and most abundantly in brain and kidney (Sap, J., et al., Proc. Natl. Acad. Sci. USA, 87:6112–6116, (1990); see also Sections 8 and 9, above).

12. EXAMPLE: CHROMOSOME LOCALIZATION OF THE HUMAN RPTPα GENE

Isolation, propagation, and characterization of parental and somatic cell hybrids using in this study have been described (Durst, M. et al., Proc Natl. Acad. Sci. USA 84:1070–1074 (1987); Ku, D-H. et al., Somatic Cell Mol. Genet. 15:297–307 (1989); Juan, C-C. et al., Proc. Natl. Acad. Sci. USA 85:8910–8913 (1988)). Presence of specific human chromosomes or regions of chromosomes has been confirmed by DNA hybridization using probes for genes assigned to specific chromosome regions. Hybrid DNAs were digested with an excess of restriction endonuclease HindIII or EcoRI, sized by electrophoresis in 0.8% agarose gels, transferred to nylon filters, and hybridized as described (Durst et al., supra). The RPTPα probe consisted of the 3'-most 0.8 kilobases (kb) of clone 31-4 (see FIG. 4B).

DNAs from 17 rodent-human somatic cell hybrids carrying overlapping subsets of human chromosome regions representing the entire human genome were tested for presence of the human RPTPα locus by Southern blot analysis. The results (FIG. 7) show that presence of the human RPTPα locus in hybrid cells correlates only with presence of a partial human chromosome 20. The data also allow a regional localization for the RPTPα locus, since hybrids PB5-1 and AB3 are each missing a part of the long arm of chromosome 20 and yet retain the RPTPα locus. Thus, the human RPTPα gene maps to 20pter-20q12.

Murine homologues of all human genes which have been mapped to human chromosome 20 map to mouse chromosome 2 (Lalley, P. A. et al., Cytogenet. Cell Genet. 51:503–532 (1989)). This appears to be true for RPTPα as well (see Section 7, above). The long arm of human chromosome 20 is involved in translocation and deletions in myeloid disorders and neoplasms (Trent, J. M., et al., Cytogenet. Cell Genet., 51:533–562, (1989)). The human RPTPα locus may be specifically involved in deletion on 20q; in this case, it would strengthen the possibility of it being a tumor-suppressor gene or anti-oncogene. Similarly in mice, in the SJL/J strain, deletion of chromosome 2 appears to be involved in the development of radiation-induced myeloid leukemia (Trakhtenbrot, L., et al., Leukemia, 2:545–550, (1988)).

The references cited above are all incorporated by reference herein, whether specifically incorporated or not.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

5,538,886

What is claimed is:

1. A recombinant nucleic acid molecule having a nucleotide sequence of SEQ ID NO:2 as depicted in FIGS. 8A–8C.

2. An isolated nucleic acid molecule comprising a nucleotide sequence that encodes (a) a polypeptide having the amino acid sequence SEQ ID No: 1 or SEQ ID No: 3; or (b) the complement of the nucleotide sequence of (a).

3. An isolated nucleic acid molecule comprising a nucleotide sequence that hybridizes under highly stringent conditions to the nucleic acid of claim 2 and encodes a naturally occurring receptor-type protein tyrosine phosphatase α.

4. A nucleic acid molecule comprising a nucleotide sequence that encodes (a) a receptor-type protein tyrosine phosphatase e having the amino acid sequence of SEQ ID No:1 and lacking one of the following segments of amino acid residues: 1–18, 19–175, 151–175, 176–264, 19–264, 265–500, 501–557, 558–790, 791–802, 1–150, 176–802 or 265–790; or (b) the complement of the nucleotide sequence of (a).

5. A nucleic acid molecule comprising a nucleotide sequence that encodes (a) a polypeptide having an amino acid sequence of SEQ ID No: 1 from amino acid residues 19–150, 19–175, 176–264, 265–500, 558–790, 1–150, 1–175, 176–802 or 265–790; or (b) the complement of the nucleotide sequence of (a).

6. The nucleic acid molecule of claims 2 or 3 which is a cDNA.

7. The nucleic acid molecule of claims 2 or 3 which is a genomic DNA.

8. A recombinant vector containing the nucleotide sequence of claims 2, 3, 4 or 5.

9. An expression vector containing the nucleotide sequence of claims 2, 3, 4 or 5 operatively associated with a regulatory nucleotide sequence containing transcriptional and translational regulatory information that controls expression of the nucleotide sequence in a host cell.

10. A genetically engineered host cell containing the nucleotide sequence of claims 2, 3, 4 or 5.

11. A genetically engineered host cell containing the nucleotide sequence of claims 2, 3, 4 or 5 operatively associated with a regulatory nucleotide sequence containing transcriptional and translational regulatory information that controls expression of the nucleotide sequence in a host cell.

12. The genetically engineered host cell of claim 11 in which the host cell is prokaryotic.

13. The genetically engineered host cell of claim 11 in which the host cell is eukaryotic.

\* \* \* \* \*